(12) United States Patent
Chun et al.

(10) Patent No.: US 12,280,063 B2
(45) Date of Patent: Apr. 22, 2025

(54) ANTI-RETROVIRAL THERAPIES AND REVERSE TRANSCRIPTASE INHIBITORS FOR TREATMENT OF ALZHEIMER'S DISEASE

(71) Applicant: Sanford Burnham Prebys Medical Discovery Institute, La Jolla, CA (US)

(72) Inventors: Jerold Chun, La Jolla, CA (US); William J. Romanow, La Jolla, CA (US); Ming-Hsiang Lee, La Jolla, CA (US); Victoria Blaho, La Jolla, CA (US)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 985 days.

(21) Appl. No.: 17/253,781

(22) PCT Filed: Jun. 20, 2019

(86) PCT No.: PCT/US2019/038284
§ 371 (c)(1),
(2) Date: Dec. 18, 2020

(87) PCT Pub. No.: WO2019/246422
PCT Pub. Date: Dec. 26, 2019

(65) Prior Publication Data
US 2021/0267995 A1 Sep. 2, 2021

Related U.S. Application Data

(60) Provisional application No. 62/687,428, filed on Jun. 20, 2018.

(51) Int. Cl.
| | | |
|---|---|---|
| A61K 31/551 | (2006.01) | |
| A61K 31/13 | (2006.01) | |
| A61K 31/27 | (2006.01) | |
| A61K 31/445 | (2006.01) | |
| A61K 31/496 | (2006.01) | |
| A61K 31/505 | (2006.01) | |
| A61K 31/513 | (2006.01) | |
| A61K 31/538 | (2006.01) | |
| A61K 31/55 | (2006.01) | |
| A61K 31/7072 | (2006.01) | |
| A61K 45/06 | (2006.01) | |
| A61P 25/28 | (2006.01) | |
| C12Q 1/6883 | (2018.01) | |
| G01N 33/68 | (2006.01) | |

(52) U.S. Cl.
CPC .......... *A61K 31/551* (2013.01); *A61K 31/13* (2013.01); *A61K 31/27* (2013.01); *A61K 31/445* (2013.01); *A61K 31/496* (2013.01); *A61K 31/505* (2013.01); *A61K 31/513* (2013.01); *A61K 31/538* (2013.01); *A61K 31/55* (2013.01); *A61K 31/7072* (2013.01); *A61K 45/06* (2013.01); *A61P 25/28* (2018.01); *C12Q 1/6883* (2013.01); *G01N 33/6896* (2013.01); *G01N 2800/2821* (2013.01)

(58) Field of Classification Search
None
See application file for complete search history.

(56) References Cited

U.S. PATENT DOCUMENTS

2017/0335320 A1    11/2017    Prochiantz et al.

FOREIGN PATENT DOCUMENTS

| WO | WO-0142266 A1 | 6/2001 |
| WO | WO-2016005327 A1 | 1/2016 |
| WO | WO-2018204408 A1 | 11/2018 |
| WO | WO-2019246422 A1 | 12/2019 |

OTHER PUBLICATIONS

Cihlar, T., & Ray, A. S. (2010). Nucleoside and nucleotide HIV reverse transcriptase inhibitors: 25 years after zidovudine. Antiviral research, 85(1), 39-58. (Year: 2010).*
Peter, A. I., & Udoh, K. P. (2015). Histomorphological Effects of Co-Administration of Efavirenz and Vitamin E on the Hippocampus of Wistar Rats. International journal of antimicrobial agents, 5, 192-198. (Year: 2015).*
PCT/US2019/038284 International Search Report and Written Opinion dated Oct. 2, 2019.
Schulte et al. Rare variants in β-Amyloid precursor protein (APP) and Parkinson's disease. Eur. J. Hum. Genet. 23(10):1328-33 (2015).
De Jonghe et al. Pathogenic APP mutations near the [gamma]-secretase cleavage site differentially affect A[beta] secretion and APP C-terminal fragment stability. Hum Mol Genet 10(16):1665-1671 (2001).
Lee et al. Somatic APP gene recombination in Alzheimer's disease and normal neurons. Nature 563(7733):639-645 (2018).
Rosen et al. OC 25: Tolerability and preliminary pharmacodynamics after single doses of MED11814, a Beta-Amyloid 42 (AB42)-specific antibody, in mild-moderate Alzheimer's Disease. Alzheimer's & Dementia: The Journal of the Alzheimer's Association 2(4):1121-1122 (2015).

(Continued)

*Primary Examiner* — Dale R Miller
(74) *Attorney, Agent, or Firm* — WILSON SONSINI GOODRICH & ROSATI

(57) ABSTRACT

Described herein are methods for inhibiting generation of one or more non-classical variant(s) of amyloid precursor protein (APP) gene. Provided herein are methods for diagnosing an individual having or suspected of having Alzheimer's-disease following identification of an expression profile or an activity profile of the one or more non-classical variant(s) and treating the individual using a reverse transcriptase inhibitor or salt thereof.

17 Claims, 54 Drawing Sheets
Specification includes a Sequence Listing.

(56) References Cited

OTHER PUBLICATIONS

Atripla® (efavirenz, emtricitabine, and tenofovir disoproxil fumarate). Prescribing Information Sheet Revised 51 pgs. (Oct. 2019).

Varatharajan, Lavanya. The transport of anti-HIV drugs across blood-CNS interfaces: summary of current knowledge and recommendations for further research. Antiviral Res. 82(2):A99-109 (2009).

* cited by examiner

| NAME | STRUCTURE | RT-PCR | DNA PCR |
|---|---|---|---|
| APP-R3/16 |  1 249 2008 2313 | ✓ | ✓ |
| APP-R2/18 |  1 210 2266 2313 | ✓ | ✓ |
| APP-R6/18 |  1 735 2233 2313 | ✓ | |
| APP-R3/14 |  1 267 1897 2313 | ✓ | ✓ |
| APP-R3/17 |  1 312 2127 2313 | ✓ | ✓ |
| APP-R1/11 |  1 24 1439 2313 | ✓ | ✓ |
| APP-R1/11-2 |  1 42 1458 2313 | ✓ | |
| APP-R1/14 |  1 41 1814 2313 | ✓ | ✓ |
| APP-R2/16 |  1 216 2014 2313 | ✓ | |
| APP-R2/17 |  1 63 2102 2313 | ✓ | ✓ |
| APP-R6/17 |  1 672 2098 2313 | ✓ | |
| APP-R2/14 |  1 198 1755 2313 | ✓ | |
| APP-D2/18-2 |  1 120 2286 2313 | | ✓ |

| Name | R1/11.1 | R1/11.2 | R1/14 | R2/17 | D2/18 | R2/14 | R2/18 | R2/16 | R3/16 | R3/14 | R3/17 | R6/17 | R6/18 |
|---|---|---|---|---|---|---|---|---|---|---|---|---|---|
| RNA | ✓ | ✓ | ✓ | ✓ |  | ✓ | ✓ | ✓ | ✓ | ✓ | ✓ | ✓ | ✓ |
| DNA | ✓ |  | ✓ | ✓ | ✓ |  | ✓ |  | ✓ | ✓ | ✓ |  |  |

ANTI-RETROVIRAL THERAPIES AND REVERSE TRANSCRIPTASE INHIBITORS FOR TREATMENT OF ALZHEIMER'S DISEASE

CROSS-REFERENCE

This application is the U.S. National Stage application of International Application No. PCT/US2019/038284, filed Jun. 20, 2019, and claims the benefit of U.S. Provisional Application No. 62/687,428, filed Jun. 20, 2018, all of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jul. 24, 2019, is named 42256-731_601) SL.txt and is 33,107 bytes in size.

BACKGROUND OF THE DISCLOSURE

Alzheimer's disease (AD) is a chronic neurodegenerative disease resulting in deterioration of cognitive function. AD is a common form of dementia and estimated to be the cause in 60-70% of the ~48 million dementia patients worldwide. AD can be classified as familial Alzheimer's disease (FAD), which is strongly associated with one or more genetic components, and sporadic AD (SAD) which can arise from both genetic factors and non-genetic factors. Further, AD can be classified based on age of onset. Individuals having AD before the age of 65 are considered having early onset AD, and those individual having AD after the age of 65 are considered having late onset AD.

AD neuropathology is characterized by elevated expression and accumulation in the central nervous system (CNS) of amyloid beta proteins and neurofibrillary tangles of hyper-phosphorylated Tau aggregates. Amyloid beta proteins comprise a peptide of 36-43 amino acids generated by cleavage of amyloid precursor protein (APP) by β- and γ-secretases. Such generated amyloid beta proteins often form misfolded oligomers that are accumulated between the nerve cells in the brain as a plaque, which is toxic to the nerve cells, consequently leading to synaptic loss and neuronal death in the brain.

Several attempts have been made to treat AD patients by eliminating abnormal accumulation of amyloid beta proteins. For example, treatment of AD patients with antibody-based therapies using secretase inhibitors or amyloid binders in several clinical trials could achieve some improvement in prohibiting the progress of AD including reduced accumulation of amyloid beta proteins in the nervous system. However, such approaches have not resulted in functional or cognitive improvement in the AD patients, suggesting that some molecular and/or cellular pathways other than cleavage of APP are substantially and maybe causally related to the development of amyloid beta protein plaques. Further, several significant side effects that were identified from the treated patients, including amyloid-related imaging abnormalities, rendered such approaches less desirable in the clinical trials.

More recently, genetic abnormalities in the gene encoding APP have been suggested as an etiology for the onset or development of AD. For example, increased APP gene copy number has been observed in AD brains and implicated in AD pathogenesis. In addition, studies have shown that increased copy number of the APP gene in Down syndrome patients is associated with neuropathology similar to AD. Further, several variants of APP gene have been reported to be associated with other types of neurodegenerative diseases (e.g., Parkinson's disease, see Schulte et al., *Rare variants in β-Amyloid precursor protein (APP) and Parkinson's disease*, Eur. J. Hum. Genet. 2015 October; 23(10):1328-33). Yet, it is not well known in the art how those APP variants are associated with AD pathogenesis, prognosis, and underlying mechanisms of the generation of the APP variants.

All publications, patents, and patent applications mentioned in this specification and exhibits are herein incorporated by reference to the same extent as if each individual publication, patent, or patent application was specifically and individually indicated to be incorporated by reference.

SUMMARY

The present invention includes methods relating to inhibiting AD progress by inhibiting generation of non-classical variant(s) of an amyloid precursor protein (APP) gene in an individual. Thus, one inventive subject matter includes a method of inhibiting generation of one or more non-classical variant(s) of an APP gene in an individual in need thereof by administering to the individual a reverse transcriptase inhibitor or salt thereof. In some embodiments, the individual does not have HIV or Hepatitis-B, and/or the individual has Alzheimer's disease. In some embodiments, the Alzheimer's disease is familial Alzheimer's disease or sporadic Alzheimer's disease.

In some embodiments, the one or more non-classical variant(s) comprises a portion or all of exon 1, 2, 3, 4, 5, 6, 7, 8, 9, 10, 11, 12, 13, 14, 15, 16, 17, 18, or combinations thereof. In some embodiments, the one or more non-classical variant(s) does not comprise exon 8. In some embodiments, the one or more non-classical variant(s) does not comprise exon 7 and exon 8. In some embodiments, one or more exon(s) in the one or more non-classical variant(s) is rearranged as compared to a control. In some embodiments, the one or more non-classical variant(s) comprises one or more single nucleotide variations (SNV) in APP. In some embodiments, the SNV in APP translates to amino acid positions in APP selected from the group consisting of P620L, A673V, D678N, T714I, V715M, V715A, I716V, V717I, V717F, T719P, and L723P. In some embodiments, the SNV in APP translates to amino acid positions in APP selected from the group consisting of A673V, A713T, T714I, V715M, V715A, I716M, V717I, V717F, T719P, and L723P. In some embodiments, the one or more non-classical variant(s) comprises a sequence as set forth in SEQ ID NO: 1, 2, 3, 4, 5, 6, 7, 8, 9, 10, 11, 12, 13, 14, 15, or 16. Preferably, the one or more non-classical variant(s) are generated by a reverse transcriptase.

It is contemplated that the reverse transcriptase inhibitor comprises a nucleoside reverse transcriptase inhibitor, which may be selected from the group consisting of azidothymidine, didanosine, stavudine, lamivudine, abacavir, tenofovir, lamivudine/zidovudine, lamivudine/zidovudine/abacavir, emtricitabine, emtricitabine/tenofovir, and abacavir/lamivudine. Alternatively and/or additionally, the reverse transcriptase inhibitor comprises a non-nucleoside reverse transcriptase inhibitor, which may be selected from the group consisting of nevirapine, delavirdine, efavirenz, etravirine, and rilpivirine. In some embodiments, the reverse transcriptase inhibitor comprises a combination of a nucleoside reverse transcriptase inhibitor and a non-nucleoside reverse transcriptase inhibitor. In some embodiments, the reverse transcriptase inhibitor is an antibody, an antigen binding fragment, a RNA interfering agent (RNAi), a small interfering RNA (siRNA), a short hairpin RNA (shRNA), a microRNA (miRNA), an antisense oligonucleotide, a peptide, a peptidomimetic, a small molecule, or an aptamer.

In some embodiments, the method further comprises administering a cholinesterase inhibitor, an N-methyl-D-aspartate (NMDA) receptor antagonist, an anti-amyloid beta antibody, or a gamma secretase inhibitor or modulator. The cholinesterase inhibitor can be selected from the group consisting of donepezil, galantamine, and rivastigmine. The NMDA receptor antagonist may include memantine. In some embodiments, the anti-amyloid beta antibody is selected from the group consisting of bapineuzumab, solanezumab, gantenerumab, crenezumab, BAN2401, ponezumab, and aducanumab. In some embodiments, the gamma secretase inhibitor or modulator is selected from the group consisting of LY450139, LY-411575, begacestat, BMS-708163, ELN-475516, MRK-003, and RO4929097. In some embodiments, the methods disclosed herein further comprise administering a beta secretase inhibitor. In some embodiments, the beta secretase inhibitor is selected from the group consisting of atabecestat, BI 1181181, donanemab, elenbecestat, gantenerumab, LY2886721, LY3202626, lanabecestat, PF-06751979, RG7129, umibecestat, and verubecestat. In some embodiments, the methods disclosed herein further comprise administering a compound selected from the group consisting of bapineuzumab, solanezumab, gammagaard, MABT5102A, AN-1792, ACC-001, Affitope AD02, CAD-106, MK-8931, HPP854, RG7129, E2609, and LY2886721. In some embodiments, methods further comprise administering donepezil, galantamine, memantine, rivastigmine, and donepezil and memantine.

Another inventive subject matter includes a method of treating or preventing Alzheimer's disease in an individual in need thereof by administering to the individual a reverse transcriptase inhibitor or salt thereof. In some embodiments, the individual does not have HIV or Hepatitis-B, and/or the individual has Alzheimer's disease. In some embodiments, the Alzheimer's disease is familial Alzheimer's disease or sporadic Alzheimer's disease.

In some embodiments, the one or more non-classical variant(s) comprises a portion or all of exon 1, 2, 3, 4, 5, 6, 7, 8, 9, 10, 11, 12, 13, 14, 15, 16, 17, 18, or combinations thereof. In some embodiments, the one or more non-classical variant(s) does not comprise exon 8. In some embodiments, the one or more non-classical variant(s) does not comprise exon 7 and exon 8. In some embodiments, one or more exon(s) in the one or more non-classical variant(s) is rearranged as compared to wild-type. In some embodiments, the one or more non-classical variant(s) comprises one or more single nucleotide variation (SNV) in APP. In some embodiments, the SNV in APP translates to amino acid positions in APP selected from the group consisting of P620L, A673V, D678N, T714I, V715M, V715A, I716V, V717I, V717F, T719P, and L723P. In some embodiments, the SNV in APP translates to amino acid positions in APP selected from the group consisting of A673V, A713T, T714I, V715M, V715A, I716M, V717I, V717F, T719P, and L723P. In some embodiments, the one or more non-classical variant(s) comprises a sequence as set forth in SEQ ID NO: 1, 2, 3, 4, 5, 6, 7, 8, 9, 10, 11, 12, 13, 14, 15, or 16. Preferably, the one or more non-classical variant(s) are generated by a reverse transcriptase.

It is contemplated that the reverse transcriptase inhibitor comprises a nucleoside reverse transcriptase inhibitor, which may be selected from the group consisting of azidothymidine, didanosine, stavudine, lamivudine, abacavir, tenofovir, lamivudine/zidovudine, lamivudine/zidovudine/abacavir, emtricitabine, emtricitabine/tenofovir, and abacavir/lamivudine. Alternatively and/or additionally, the reverse transcriptase inhibitor comprises a non-nucleoside reverse transcriptase inhibitor, which may be selected from the group consisting of nevirapine, delavirdine, efavirenz, etravirine, and rilpivirine. In some embodiments, the reverse transcriptase inhibitor comprises the combination of a nucleoside reverse transcriptase inhibitor and a non-nucleoside reverse transcriptase inhibitor. In some embodiments, the reverse transcriptase inhibitor is an antibody, an antigen binding fragment, a RNA interfering agent (RNAi), a small interfering RNA (siRNA), a short hairpin RNA (shRNA), a microRNA (miRNA), an antisense oligonucleotide, a peptide, a peptidomimetic, a small molecule, or an aptamer.

In some embodiments, the method further comprises administering a cholinesterase inhibitor, an N-methyl-D-aspartate (NMDA) receptor antagonist, an anti-amyloid beta antibody, a gamma secretase inhibitor or modulator, or a beta secretase inhibitor. The cholinesterase inhibitor can be selected from the group consisting of donepezil, galantamine, and rivastigmine. The NMDA receptor antagonist may include memantine. In some embodiments, the anti-amyloid beta antibody is selected from the group consisting of bapineuzumab, solanezumab, gantenerumab, crenezumab, BAN2401, ponezumab, and aducanumab. In some embodiments, the gamma secretase inhibitor or modulator is selected from the group consisting of LY450139, LY-411575, begacestat, BMS-708163, ELN-475516, MRK-003, and RO4929097. In some embodiments, methods further comprise administering donepezil, galantamine, memantine, rivastigmine, and donepezil and memantine.

In some embodiments, the Alzheimer's disease is characterized by amyloid beta protein plaque depositions which comprises a portion of or all amyloid beta protein, or accumulation of soluble amyloid beta proteins. In some embodiments, the amyloid beta protein plaque depositions result from increased APP gene expression and/or amyloid beta protein aggregates associated with the one or more non-classical variant(s) of APP gene.

In some embodiments, described herein is a method of diagnosing and treating a disease or disorder in an individual characterized by accumulation of amyloid beta protein in an individual in need thereof. In some embodiments, the method comprises the step of: (a) identifying the individual as having the disease or disorder characterized by accumulation of amyloid beta protein by comparing an expression profile or an activity profile of one or more non-classical variant(s) of an APP gene to a reference expression profile of the one or more non-classical variant(s) derived from a cohort of control individuals, wherein the expression profile or the activity profile of the one or more non-classical variant(s) is measured by a method including long-read sequencing of a biological sample from the individual or binding of one or more probe(s) to the biological sample from the individual. Preferably, the expression profile or the activity profile of the one or more non-classical variant(s) is associated with the neurological disease or disorder. In some embodiments, the methods described herein further comprise the step of: (b) administering to the individual having an expression profile or an activity profile of the one or more non-classical variant(s) a reverse transcriptase inhibitor or salt thereof.

In some embodiments, the individual does not have HIV or Hepatitis-B, and/or the individual has Alzheimer's disease. In some embodiments, the Alzheimer's disease is familial Alzheimer's disease or sporadic Alzheimer's disease.

In some embodiments, the one or more non-classical variant(s) comprises a portion or all of exon 1, 2, 3, 4, 5, 6, 7, 8, 9, 10, 11, 12, 13, 14, 15, 16, 17, 18, or combinations thereof. In some embodiments, the one or more non-classical variant(s) does not comprise exon 8. In some embodiments, the one or more non-classical variant(s) does not comprise exon 7 and exon 8. In some embodiments, one or more exon(s) in the one or more non-classical variant(s) is rearranged as compared to a control. In some embodiments, the one or more non-classical variant(s) comprises one or more single nucleotide variations (SNV) in APP. In some embodiments, the SNV in APP translates to amino acid positions in APP selected from the group consisting of P620L, A673V, D678N, T714I, V715M, V715A, I716V, V717I, V717F, T719P, and L723P. In some embodiments, the SNV in APP translates to amino acid positions in APP selected from the group consisting of A673V, A713T, T714I, V715M, V715A, I716M, V717I, V717F, T719P, and L723P. In some embodiments, the one or more non-classical variant(s) comprises a sequence as set forth in SEQ ID NO: 1, 2, 3, 4, 5, 6, 7, 8, 9, 10, 11, 12, 13, 14, 15, or 16. Preferably, the one or more non-classical variant(s) are generated by a reverse transcriptase.

It is contemplated that the reverse transcriptase inhibitor comprises a nucleoside reverse transcriptase inhibitor, which may be selected from the group consisting of azidothymidine, didanosine, stavudine, lamivudine, abacavir, tenofovir, lamivudine/zidovudine, lamivudine/zidovudine/abacavir, emtricitabine, emtricitabine/tenofovir, and abacavir/lamivudine. Alternatively and/or additionally, the reverse transcriptase inhibitor comprises a non-nucleoside reverse transcriptase inhibitor, which may be selected from the group consisting of nevirapine, delavirdine, efavirenz, etravirine, and rilpivirine. In some embodiments, the reverse transcriptase inhibitor comprises the combination of a nucleoside reverse transcriptase inhibitor and a non-nucleoside reverse transcriptase inhibitor. In some embodiments, the reverse transcriptase inhibitor is an antibody, an antigen binding fragment, a RNA interfering agent (RNAi), a small interfering RNA (siRNA), a short hairpin RNA (shRNA), a microRNA (miRNA), an antisense oligonucleotide, a peptide, a peptidomimetic, a small molecule, or an aptamer.

In some embodiments, the method further comprises administering a cholinesterase inhibitor, an N-methyl-D-aspartate (NMDA) receptor antagonist, an anti-amyloid beta antibody, a gamma secretase inhibitor or modulator, and/or a beta secretase inhibitor. The cholinesterase inhibitor can be selected from the group consisting of donepezil, galantamine, and rivastigmine. The NMDA receptor antagonist may include memantine. In some embodiments, the anti-amyloid beta antibody is selected from the group consisting of bapineuzumab, solanezumab, gantenerumab, crenezumab, BAN2401, ponezumab, and aducanumab. In some embodiments, the gamma secretase inhibitor or modulator is selected from the group consisting of LY450139, LY-411575, begacestat, BMS-708163, ELN-475516, MRK-003, and RO4929097. In some embodiments, the beta secretase inhibitor is selected from the group consisting of atabecestat, BI 1181181, donanemab, elenbecestat, gantenerumab, LY2886721, LY3202626, lanabecestat, PF-06751979, RG7129, umibecestat, and verubecestat. In some embodiments, the methods disclosed herein further comprise administering a compound selected from the group consisting of bapineuzumab, solanezumab, gammagaard, MABT5102A, AN-1792, ACC-001, Affitope AD02, CAD-106, MK-8931, HPP854, RG7129, E2609, and LY2886721. In some embodiments, methods further comprise administering donepezil, galantamine, memantine, rivastigmine, and donepezil and memantine.

In some embodiments, the Alzheimer's disease is characterized by amyloid beta protein plaque depositions which comprises a portion of or all amyloid beta protein, or accumulation of soluble amyloid beta proteins. In some embodiments, the amyloid beta protein plaque depositions result from increased APP gene expression and/or amyloid beta protein aggregates associated with the one or more non-classical variant(s) of APP gene.

In some embodiments, the expression profile is expression level(s) of the one or more non-classical variant(s). In some embodiments, the expression profile is expression level(s) of a set of different non-classical variants. In some embodiments, the long-read sequencing is RNA sequencing (RNA-seq). Alternatively and/or additionally, the long-read sequencing is DNA sequencing.

In some embodiments, the methods further comprises quantifying the expression level of the one or more non-classical variant(s) by counting a number of reads that map to a sequence of the one or more non-classical variant(s). In some embodiments, the method may further comprise isolating and purifying RNA or DNA from the biological sample prior to the long-read sequencing. In some embodiments, the method may further comprise reverse transcribing RNA to cDNA prior to the long-read sequencing. In some embodiments, the method may further comprise quantifying the expression level by quantitative polymerase chain reaction (qPCR).

In some embodiments, the method further comprises capturing the one or more non-classical variant(s) from the biological sample on a solid support prior to contacting the one or more non-classical variant(s) with the one or more probe(s). In some embodiments, the one or more non-classical variant(s) is detected by in situ hybridization or immunological hybridization. In some embodiments, the in situ hybridization is chromogenic in situ hybridization or fluorescence in situ hybridization. In some embodiments, binding of the one or more probe(s) to the one or more non-classical variant(s) further comprises a pull-down assay. In some embodiments, the one or more probe(s) for the pull-down assay are designed to hybridize to a portion or all of exon 1, 2, 3, 4, 5, 6, 7, 8, 9, 10, 11, 12, 13, 14, 15, 16, 17, 18, or combinations thereof. In some embodiments, a probe in the one or more probe(s) is labeled using an affinity tag. In some embodiments, the affinity tag is biotin, desthiobiotin, histidine, polyhistidine, myc, hemagglutinin (HA), FLAG, glutathione S transferase (GST), or derivatives thereof. In some embodiments, the affinity tag is recognized by avidin, streptavidin, nickel, or glutathione. In some embodiments, the one or more probe(s) are selected from polynucleotides or polypeptides. In some embodiments, the one or more probe(s) hybridize to RNA or DNA within the biological sample. In some embodiments, the one or more probe(s) hybridize to a range of about 35 to about 50 nucleotides of the RNA or DNA. In some embodiments, the one or more probe(s) bind to one or more protein(s) encoded by the one or more non-classical variant(s). In some embodiments, the one or more probe(s) comprise an antibody or fragment thereof. In some embodiments, a probe in the one or more probe(s) is labeled using a fluorochrome or a radioactive isotope.

In still another inventive subject matter, the inventors contemplate use of a reverse transcriptase inhibitor for treating a subject developing or suspected to develop Alzheimer's disease, for inhibiting generation of one or more non-classical variant(s) of an amyloid precursor protein (APP) gene in an individual in need thereof, or for manufacturing a pharmaceutical composition for treating a subject developing or suspected to develop Alzheimer's disease.

It is contemplated that the reverse transcriptase inhibitor comprises a nucleoside reverse transcriptase inhibitor, which may be selected from the group consisting of azidothymidine, didanosine, stavudine, lamivudine, abacavir, tenofovir, lamivudine/zidovudine, lamivudine/zidovudine/abacavir, emtricitabine, emtricitabine/tenofovir, and abacavir/lamivudine. Alternatively and/or additionally, the reverse transcriptase inhibitor comprises a non-nucleoside reverse transcriptase inhibitor, which may be selected from the group consisting of nevirapine, delavirdine, efavirenz, etravirine, and rilpivirine. In some embodiments, the reverse transcriptase inhibitor comprises the combination of a nucleoside reverse transcriptase inhibitor and a non-nucleoside reverse transcriptase inhibitor. In some embodiments, the reverse transcriptase inhibitor is an antibody, an antigen binding fragment, a RNA interfering agent (RNAi), a small interfering RNA (siRNA), a short hairpin RNA (shRNA), a microRNA (miRNA), an antisense oligonucleotide, a peptide, a peptidomimetic, a small molecule, or an aptamer.

In some embodiments, the one or more non-classical variant(s) comprises a portion or all of exon 1, 2, 3, 4, 5, 6, 7, 8, 9, 10, 11, 12, 13, 14, 15, 16, 17, 18, or combinations thereof. In some embodiments, the one or more non-classical variant(s) does not comprise exon 8. In some embodiments, the one or more non-classical variant(s) does not comprise exon 7 and exon 8. In some embodiments, one or more exon(s) in the one or more non-classical variant(s) is rearranged as compared to a control. In some embodiments, the one or more non-classical variant(s) comprises one or more single nucleotide variations (SNV) in APP. In some embodiments, the SNV in APP translates to amino acid positions in APP selected from the group consisting of P620L, A673V, D678N, T714I, V715M, V715A, I716V, V717I, V717F, T719P, and L723P. In some embodiments, the SNV in APP translates to amino acid positions in APP selected from the group consisting of A673V, A713T, T714I, V715M, V715A, I716M, V717I, V717F, T719P, and L723P. In some embodiments, the one or more non-classical variant(s) comprises a sequence as set forth in SEQ ID NO: 1, 2, 3, 4, 5, 6, 7, 8, 9, 10, 11, 12, 13, 14, 15, or 16. Preferably, the one or more non-classical variant(s) are generated by a reverse transcriptase.

In some embodiments, the pharmaceutical composition further comprises a cholinesterase inhibitor (e.g., selected from the group consisting of donepezil, galantamine, and rivastigmine), an N-methyl-D-aspartate (NMDA) receptor antagonist (e.g., memantine, etc.), an anti-amyloid beta antibody, a gamma secretase inhibitor or modulator (e.g., selected from the group consisting of LY450139, LY-411575, begacestat, BMS-708163, ELN-475516, MRK-003, and RO4929097, etc.), and/or a beta secretase inhibitor (e.g., selected from the group consisting of atabecestat, BI 1181181, donanemab, elenbecestat, gantenerumab, LY2886721, LY3202626, lanabecestat, PF-06751979, RG7129, umibecestat, and verubecestat).

BRIEF DESCRIPTION OF THE DRAWINGS

FIG. 15G discloses the sequences in the left column as SEQ ID NOS 47, 43 and 48, the sequences in the middle column as SEQ ID NOS 49 and 50 the sequences in the right column as SEQ ID NOS 51-55, 41 and 56, all respectively, in order of appearance.

FIG. 15K discloses SEQ ID NOS 57 and 58, in order of appearance.

FIG. 17H and FIG. 17J illustrate data relative to samples without restriction enzyme and statistical significance was determined using a two-way ANOVA (p<0.0001) with multiple comparisons and Sidak correction.

FIG. 19C illustrates representative images of neuronal and non-neuronal nuclei from 177, 566, 728, and 829 days old mice. FIG. 19D illustrates a graph of relative 16/17 foci area (y-axis) versus age (days) on the x-axis. +, mean; line, median; box, 75/25 percentiles; whiskers, 90/10 percentiles (by Ordinary One-way ANOVA with multiple comparisons and Sidak correction, $*p<0.05$, $p<0.01$, $*p<0.001$, $****p<0.0001$. n.s., not significant). Brackets depict significance between matched neurons and non-neurons. Significance over error bars=compared to same cell type, one age older.

FIG. 20A discloses SEQ ID NO: 33.

FIGS. 20E-20H illustrate graphs of relative reverse transcriptase activity from SSII, CHO lysate, and brain lysate. Triplicate samples were run with three replicates, and experiments were repeated 3 times (total N=27 replicates per sample). Statistical significance was determined using a two-way ANOVA comparing column means with Tukey corrections. $*p<0.05$, $p<0.01$, $*p<0.001$, $****p<0.0001$. n.s., not significant. Error bars are ±SEM.

DETAILED DESCRIPTION

Definitions

Figure 1:
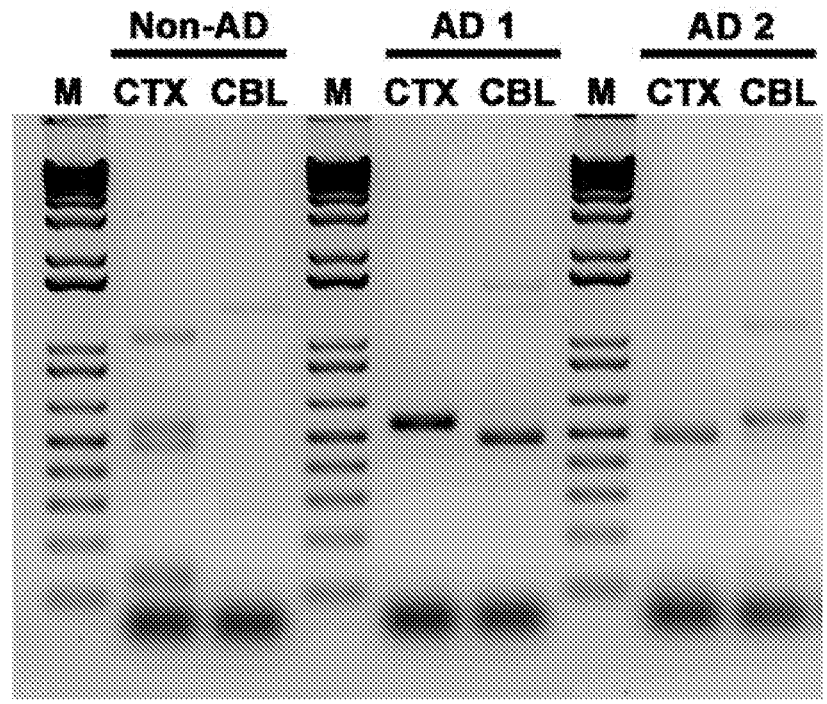
FIG. 1 illustrates a gel electrophoresis of RT-PCR from neurons isolated from cortices (CTX) and cerebellums (CBL) from non-diseased (Non-AD) postmortem brains and Alzheimer's disease (AD) brains. M represents DNA ladder marker.

As used in the specification and appended claims, unless specified to the contrary, the following terms have the meaning indicated below.

As used herein, the term "comprise" or variations thereof such as "comprises" or "comprising" are to be read to indicate the inclusion of any recited feature but not the exclusion of any other features. Thus, as used herein, the term "comprising" is inclusive and does not exclude additional, unrecited features. In some embodiments of any of the compositions and methods provided herein, "comprising" may be replaced with "consisting essentially of" or "consisting of." The phrase "consisting essentially of" is used herein to require the specified feature(s) as well as those which do not materially affect the character or function of the claimed disclosure. As used herein, the term "consisting" is used to indicate the presence of the recited feature alone.

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well of any dividual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well of any dividual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers+/−10% thereof, or 10% below the lower listed limit and 10% above the higher listed limit for the values listed for a range.

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

As used herein, "treatment of" or "treating," 'applying", or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease or condition, or to a patient reporting one or more of the physiological symptoms of a disease, even though a diagnosis of this disease has not been made.

The terms "subject," "individual," or "patient" are often used interchangeably herein. A "subject" can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. The subject may be diagnosed or suspected of being at high risk for a disease. In some cases, the subject is not necessarily diagnosed or suspected of being at high risk for the disease.

The section headings used herein are for organizational purposes only and are not to be construed as limiting the subject matter described.

The term "non-classical variant" as used herein refers to RNA or DNA molecules comprising intraexonic junctions between exons and/or conventional spliced exon-exon junctions, and RNA or DNA molecules lacking introns between exons.

The term "genomic cDNA" or "gencDNA" as used herein refers to a genomic variant lacking introns. In some embodiments, the gencDNA comprises intraexonic junctions between exons. In some embodiments, the gencDNA comprises inverted exons. In some embodiments, the gencDNA is generated by reverse transcription of a non-classical RNA variant. In some embodiments, the gencDNA is incorporated into genomic DNA. In some embodiments, the gencDNA comprises single nucleotide variations (SNVs). In some embodiments, the gencDNA comprises a point mutation.

The term "expression" as used herein refers to a transcriptional or translational product of a gene.

The term "activity" as used herein refers to protein biological or chemical function.

The term "RNA" as used herein refers to a molecule comprising at least one ribonucleotide residue. By "ribonucleotide" is meant a nucleotide with a hydroxyl group at the 2' position of a beta-D-ribo-furanose moiety. The term RNA includes, but not limited to, mRNA, ribosomal RNA, tRNA, non-protein-coding RNA (npcRNA), non-messenger RNA, functional RNA (fRNA), long non-coding RNA (lncRNA), pre-mRNAs, and primary miRNAs (pri-miRNAs). The term RNA includes, for example, double-stranded (ds) RNAs; single-stranded RNAs; and isolated RNAs such as partially purified RNA, essentially pure RNA, synthetic RNA, recombinantly produced RNA, as well as altered RNA that differ from naturally-occurring RNA by the addition, deletion, substitution and/or alteration of one or more nucleotides. Such alterations can include addition of non-nucleotide material, such as to the end(s) of the siRNA or internally, for example at one or more nucleotides of the RNA. Nucleotides in the RNA molecules described herein can also comprise non-standard nucleotides, such as non-naturally occurring nucleotides or chemically synthesized nucleotides or deoxynucleotides. These altered RNAs can be referred to as analogs or analogs of naturally-occurring RNA.

The term "RNAi" as used herein refers to an RNA molecule that induces RNA interference (RNAi). In some embodiments, the RNAi molecule is a dsRNA molecule that will generate a siRNA molecule or miRNA molecule following contact with Dicer (i.e., an RNAi molecule precursor). In some embodiments, the RNAi molecule is a siRNA duplex, a siRNA sense molecule, a siRNA anti-sense molecule, a miRNA duplex, a miRNA sense molecule, a miRNA anti-sense molecule, and analogues thereof.

The terms "binding fragment," "antibody fragment," or "antigen binding fragment" are used herein, for purposes of the specification and claims, to mean a portion or fragment of an intact antibody molecule, preferably wherein the fragment retains antigen-binding function. Examples of antibody fragments include Fab, Fab', F(ab')2, Fd, Fd' and Fv fragments, diabodies, linear antibodies, single-chain antibody molecules, single-chain binding polypeptides, scFv, bivalent scFv, tetravalent scFv, and bispecific or multispecific antibodies formed from antibody fragments. In some embodiments, an antibody fragment is a single-domain antibody. In some embodiments, an antibody is a nanobody, a synthetic nanobody, or a derivative of a nanobody.

"Fab" fragments are typically produced by papain digestion of antibodies resulting in the production of two identical antigen-binding fragments, each with a single antigen-binding site and a residual "Fc" fragment. Pepsin treatment yields a F(ab')2 fragment that has two antigen-combining sites capable of cross-linking antigen. An "Fv" is the minimum antibody fragment that contains a complete antigen recognition and binding site. In a two-chain Fv species, this region consists of a dimer of one heavy- and one light-chain variable domain in tight, non-covalent association. In a single-chain Fv (scFv) species, one heavy- and one light-chain variable domain are covalently linked by a flexible peptide linker such that the light and heavy chains associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although usually at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy-chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments that have hinge cysteines between them. Other chemical couplings of antibody fragments are also suitable.

The term "monoclonal antibody" refers to an antibody obtained from a population of substantially homogeneous antibodies, i.e., the individual antibodies comprising the population are identical except for possible naturally occurring mutations that are present in minor amounts. In some embodiments, monoclonal antibodies are made, for example, by the hybridoma method. In some embodiments, monoclonal antibodies are isolated from phage antibody libraries.

The antibodies herein include monoclonal, polyclonal, recombinant, chimeric, humanized, bi-specific, grafted, human, and fragments thereof including antibodies altered by any means to be less immunogenic in humans. Thus, for example, the monoclonal antibodies and fragments herein include "chimeric" antibodies and "humanized" antibodies. In general, chimeric antibodies include a portion of the heavy and/or light chain that is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, so long as they exhibit the desired biological activity. For example in some embodiments, a chimeric antibody contains variable regions derived from a mouse and constant regions derived from human in which the constant region contains sequences homologous to both human IgG2 and human IgG4. Numerous methods for preparing "chimeric" antibodies are known in the art. "Humanized" forms of non-human (e.g., murine) antibodies or fragments are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include, grafted antibodies or CDR grafted antibodies wherein part or all of the amino acid sequence of one or more complementarity determining regions (CDRs) derived from a non-human animal antibody is grafted to an appropriate position of a human antibody while maintaining the desired binding specificity and/or affinity of the original non-human antibody. In some embodiments, corresponding non-human residues replace Fv framework residues of the human immunoglobulin. In some embodiments, humanized antibodies comprise residues that are found neither in the recipient antibody nor in the imported CDR or framework sequences. These modifications are made to further refine and optimize antibody performance. In some embodiments, the humanized antibody comprises substantially all of at least one, and typically two, variable domains, in which all or substantially all of the CDR regions correspond to those of a non-human immunoglobulin and all or substantially all of the FR regions are those of a human immunoglobulin consensus sequence.

The term "reverse transcriptase" refers to an enzyme having reverse transcriptase activity. In some embodiments, the reverse transcriptase has both an RNA-dependent DNA polymerase activity and a DNA-dependent DNA polymerase activity. In general, such enzymes include, but are not limited to, retroviral reverse transcriptase, retrotransposon reverse transcriptase, retroplasmid reverse transcriptase, retron reverse transcriptase, bacterial reverse transcriptase, group II intron-derived reverse transcriptase, and mutants, variants or derivatives thereof. Non-retroviral reverse transcriptases include non-long terminal repeat (LTR) retrotransposon reverse transcriptase, retroplasmid reverse transcriptase, retron reverse transcriptase, and group II intron reverse transcriptase. In some embodiments, the reverse transcriptase is a telomerase reverse transcriptase (TERT), human endogenous retrovirus type K (HERV-K), LINE-1 retrotransposable element ORF2, or human immunodeficiency virus type 1 reverse transcriptase. In some embodiments, the reverse transcriptase is a DNA polymerase activity that uses RNA as a template.

Various abnormalities in APP gene, including mutations such as copy number variants, have been reported to be associated with early onset or progress of AD. Yet, mechanisms how such mutations contribute to the beta amyloid plaque have been remained elusive. The inventors discovered that genomic recombination of APP gene, which occurs mosaically to generate thousands of variant 'genomic cDNAs' (gencDNAs) results in various mutations such as intra-exonic junctions, insertions, deletions, and/or single nucleotide variations. Further, the inventors found that such genomic recombination occurs via neuronal 'retro-insertion' of RNA that involves transcription, DNA breaks, and reverse transcriptase activity. Moreover, the inventors found that such recombination by 'retro-insertion' of RNA frequently occurs in the neurons in the sporadic AD patients' brain.

Viewed from different perspective, the inventors found that inhibition of genomic recombination of APP gene by reducing or inhibiting activity of reverse transcriptase in the AD patients' brain can prevents accumulation of beta amyloid protein and generation of beta amyloid plaque in the brain. Thus, the inventors contemplate a method of inhibiting generation of one or more non-classical variant(s) of an amyloid precursor protein (APP) gene in an individual in need thereof, a method of treating or preventing Alzheimer's disease, or a method of diagnosing and treating a disease or disorder in an individual characterized by accumulation of amyloid beta protein, by administering to the individual a reverse transcriptase inhibitor or salt thereof. Conversely, the inventors contemplate use of a reverse transcriptase inhibitor for treating a subject developing or suspected to develop Alzheimer's disease, for inhibiting generation of one or more non-classical variant(s) of an amyloid precursor protein (APP) gene in an individual in need thereof, or for manufacturing a pharmaceutical composition for treating a subject developing or suspected to develop Alzheimer's disease.

Non-Classical Variants of APP Gene.

Various forms of non-classical variants are contemplated. For example, non-classical variants may include intra-exonic rearrangements. In another example, the non-classical variants may lack introns to so form genomic cDNAs (gencDNAs). In such example, the gencDNAs may range from full-length cDNA copies of expressed, brain-specific RNA splice variants to smaller (less than full-length) forms. In some embodiments, the non-classical variants may comprise a portion of a first exon of APP and a portion of a second exon of APP. In still another example, the non-classical variants comprise intraexonic junctions and lack introns.

In still another example, the non-classical variants comprise inverted exons. In some embodiments, the non-classical variants comprise one or more mutations, insertions, deletions, single nucleotide variations (SNVs), copy number variation (CNV), L1 repeat elements, or combinations thereof. The SNVs can be somatic SNVs or germline SNVs.

The inventors contemplate that non-classical variants of APP, especially those expressed in the neurons in the AD brain, are generated via retro-insertion of RNA into genomic DNA. Such mechanism begins with transcription of genomic DNA, then proceed with DNA breaks, generating a piece of genomic cDNA via reverse transcription of RNA transcript, and insertion of such generated genomic cDNA into the genome. In some embodiments, the reverse transcription in this mechanism is cell-type specific. For example, the non-classical variants are generated by neuron-specific RNA reverse transcription. In other examples, the non-classical variants are generated by microglia-specific reverse transcription, astrocyte-specific reverse transcription, or oligodendrocyte-specific reverse transcription.

In some embodiments, the non-classical variants are coding DNA or RNA. In some embodiments, the non-classical variants are non-coding DNA or RNA.

In some embodiments, the non-classical variants comprise a portion or all of an exon of APP. In some embodiments, the non-classical variants comprise a portion or all of exon 1, 2, 3, 4, 5, 6, 7, 8, 9, 10, 11, 12, 13, 14, 15, 16, 17, 18, or combinations thereof of APP. In some embodiments, the non-classical variants comprise a portion or all of exon 1, 2, 3, 4, 5, 6, 7, 9, 10, 11, 12, 13, 14, 15, 16, 17, 18, or combinations thereof of APP. In some embodiments, the non-classical variants do not comprise exon 8. In some embodiments, the non-classical variants do not comprise exon 7. In some embodiments, the non-classical variants do not comprise exon 7 and exon 8. In some embodiments, the non-classical variants of APP comprise a portion or all of exon 1, 2, 3, 4, 5, 6, 7, 8, 9, 10, 11, 12, 13, 14, 15, 16, 17, or 18 of APP, wherein the portion or all of the exon 1, 2, 3, 4, 5, 6, 7, 8, 9, 10, 11, 12, 13, 14, 15, 16, 17, or 18 of APP is inverted. In some embodiments, non-classical variants of APP comprise at least or about 10 nucleotides (nt), 15 nt, 20 nt, 25 nt, 30 nt, 40 nt, 50 nt, 75 nt, 100 nt, 150 nt, 200 nt, or more than 200 nt of exon 1, 2, 3, 4, 5, 6, 7, 8, 9, 10, 11, 12, 13, 14, 15, 16, 17, 18, or combinations thereof.

Non-classical transcript variants may comprise portions of at least 2 exons. In some embodiments, the non-classical variants comprise a portion of exon 1 and a portion of exon 11. In some embodiments, the non-classical variants comprise a portion of exon 1 and a portion of exon 12. In some embodiments, the non-classical variants comprise a portion of exon 1 and a portion of exon 14. In some embodiments, the non-classical variants comprise a portion of exon 1 and a portion of exon 17. In some embodiments, the non-classical variants comprise a portion of exon 2 and a portion of exon 14. In some embodiments, the non-classical variants comprise a portion of exon 2 and a portion of exon 16. In some embodiments, the non-classical variants comprise a portion of exon 2 and a portion of exon 17. In some embodiments, the non-classical variants comprise a portion of exon 2 and a portion of exon 18. In some embodiments, the non-classical variants comprise a portion of exon 3 and a portion of exon 9. In some embodiments, the non-classical variants comprise a portion of exon 3 and a portion of exon 14. In some embodiments, the non-classical variants comprise a portion of exon 3 and a portion of exon 16. In some embodiments, the non-classical variants comprise a portion of exon 3 and a portion of exon 17. In some embodiments, the non-classical variants comprise a portion of exon 3 and a portion of exon 18. In some embodiments, the non-classical variants comprise a portion of exon 5 and a portion of exon 16. In some embodiments, the non-classical variants comprise a portion of exon comprise exon 6 and a portion of exon 12. In some embodiments, the non-classical variants comprise a portion of exon 6 and a portion of exon 16. In some embodiments, the non-classical variants comprise a portion of exon 6 and a portion of exon 17. In some embodiments, the non-classical variants comprise a portion of exon 6 and a portion of exon 18. In some embodiments, the non-classical variants comprise a portion of exon 16 and a portion exon 18.

In some embodiments, the non-classical variants of APP may comprise portions of at least two exons, in which the at least two exons are linked by intraexonic junctions. In some embodiments, the intraexonic junction is between exon 1 and exon 2, 3, 4, 5, 6, 7, 8, 9, 10, 11, 12, 13, 14, 15, 16, 17, 18, or combinations thereof. In some embodiments, the intraexonic junction is between exon 2 and exon 1, 3, 4, 5, 6, 7, 8, 9, 10, 11, 12, 13, 14, 15, 16, 17, 18, or combinations thereof. In some embodiments, the intraexonic junction is between exon 3 and exon 1, 2, 4, 5, 6, 7, 8, 9, 10, 11, 12, 13, 14, 15, 16, 17, 18, or combinations thereof. In some embodiments, the intraexonic junction is between exon 4 and exon 1, 2, 3, 5, 6, 7, 8, 9, 10, 11, 12, 13, 14, 15, 16, 17, 18, or combinations thereof. In some embodiments, the intraexonic junction is between exon 5 and exon 1, 2, 3, 4, 6, 7, 8, 9, 10, 11, 12, 13, 14, 15, 16, 17, 18, or combinations thereof. In some embodiments, the intraexonic junction is between exon 6 and exon 1, 2, 3, 4, 5, 7, 8, 9, 10, 11, 12, 13, 14, 15, 16, 17, 18, or combinations thereof. In some embodiments, the intraexonic junction is between exon 7 and exon 1, 2, 3, 4, 5, 6, 8, 9, 10, 11, 12, 13, 14, 15, 16, 17, 18, or combinations thereof. In some embodiments, the intraexonic junction is between exon 8 and exon 1, 2, 3, 4, 5, 6, 7, 9, 10, 11, 12, 13, 14, 15, 16, 17, 18, or combinations thereof. In some embodiments, the intraexonic junction is between exon 9 and exon 1, 2, 3, 4, 5, 6, 7, 8, 10, 11, 12, 13, 14, 15, 16, 17, 18, or combinations thereof. In some embodiments, the intraexonic junction is between exon 10 and exon 1, 2, 3, 4, 5, 6, 7, 8, 9, 11, 12, 13, 14, 15, 16, 17, 18, or combinations thereof. In some embodiments, the intraexonic junction is between exon 11 and exon 1, 2, 3, 4, 5, 6, 7, 8, 9, 10, 12, 13, 14, 15, 16, 17, 18, or combinations thereof. In some embodiments, the intraexonic junction is between exon 12 and exon 1, 2, 3, 4, 5, 6, 7, 8, 9, 10, 11, 13, 14, 15, 16, 17, 18, or combinations thereof. In some embodiments, the intraexonic junction is between exon 13 and exon 1, 2, 3, 4, 5, 6, 7, 8, 9, 10, 11, 12, 14, 15, 16, 17, 18, or combinations thereof. In some embodiments, the intraexonic junction is between exon 14 and exon 1, 2, 3, 4, 5, 6, 7, 8, 9, 10, 11, 12, 13, 15, 16, 17, 18, or combinations thereof. In some embodiments, the intraexonic junction is between exon 15 and exon 1, 2, 3, 4, 5, 6, 7, 8, 9, 10, 11, 12, 13, 14, 16, 17, 18, or combinations thereof. In some embodiments, the intraexonic junction is between exon 16 and exon 1, 2, 3, 4, 5, 6, 7, 8, 9, 10, 11, 12, 13, 14, 15, 17, 18, or combinations thereof. In some embodiments, the intraexonic junction is between exon 17 and exon 1, 2, 3, 4, 5, 6, 7, 8, 9, 10, 11, 12, 13, 14, 15, 16, 18, or combinations thereof. In some embodiments, the intraexonic junction is between exon 18 and exon 1, 2, 3, 4, 5, 6, 7, 8, 9, 10, 11, 12, 13, 14, 15, 16, 17, or combinations thereof.

In some embodiments, sequence complementarity exists in non-classical variants of APP in the intraexonic junctions. In some embodiments, the sequence complementarity is at least or about 2, 4, 6, 8, 10, 12, 14, 16, 18, 20, 22, 24, 26, 28, 30, 32, 34, 36, 38, 40, 50, 60, 70, 80, 90, 100, or more than 100 nucleotides. In some embodiments, the sequence complementarity is in a range of about 2 nucleotides to 20 nucleotides. In some embodiments, the sequence complementarity is in a range of about 2 nucleotides to about 200 nucleotides, about 4 nucleotides to about 180 nucleotides, about 6 nucleotides to about 160 nucleotides, about 8 nucleotides to about 140 nucleotides, about 10 nucleotides to about 120 nucleotides, about 12 nucleotides to about 100 nucleotides, about 14 nucleotides to about 80 nucleotides, about 16 nucleotides to about 60 nucleotides, or about 20 nucleotides to about 40 nucleotides.

Non-classical variants of APP as described herein, in certain embodiments, comprise number of variable sequences. In some embodiments, a number of variable sequences is at least or about 2, 10, 20, 30, 40, 50, 60, 70, 80, 90, 100, 200, 300, 400, 500, 600, 700, 800, 900, 1000, or more than 1000 sequences. In some embodiments, a number of variable sequences in in a range of about 2 sequences to about 1000 sequences, about 4 sequences to about 900 sequences, about 6 sequences to about 800 sequences, about 8 sequences to about 700 sequences, about 10 sequences to about 600 sequences, about 20 sequences to about 500 sequences, about 30 sequences to about 400 sequences, about 40 sequences to about 300 sequences, about 50 sequences to about 200 sequences, and about 60 sequences to about 100 sequences.

In some embodiments, non-classical variants of APP comprising portions of at least 2 exons further comprise a deletion of at least one exon or a portion of at least one exon of APP. For example, the non-classical transcript variants comprise a deletion of exon 8 or a portion of exon 8 of APP. In some embodiments, the non-classical transcript variants comprise a deletion of exon 7 or a portion of exon 7 of APP. In some embodiments, the non-classical transcript variants comprise a deletion of exon or a portion of exon 1, 2, 3, 4, 5, 6, 7, 8, 9, 10, 11, 12, 13, 14, 15, 16, 17, 18, or combinations thereof of APP. In some embodiments, the non-classical transcript variants comprise a deletion of exon or a portion of exon 2, 3, 4, 5, 6, 7, 8, 9, 10, 11, 12, 13, 14, 15, 16, 17, or combinations thereof.

The APP mRNA sequence is set forth at NCBI Reference Sequence: NM_000484.3. Exemplary non-classical variants are illustrated in Table 1.

TABLE 1

| SEQ ID NO | Name* | Sequence** |
|---|---|---|
| 1 | cAPP-R3/16 | ATGCTGCCCGGTTTGGCACTGCTCCTGCTGGCCGCCTGGACGGCTC GGGCGCTGGAGGTACCCACTGATGGTAATGCTGGCCTGCTGGCTG AACCCCAGATTGCCATGTTCTGTGGCAGACTGAACATGCACATGA ATGTCCAGAATGGGAAGTGGGATTCAGATCCATCAGGGACCAAAA CCTGCATTGATACCAAGGAAGGCATCCTGCAGTATTGCCAAGAAG TCTACCCTGAACTGCAGATCACC:AAGATGGATGCAGAATTCCGAC ATGACTCAGGATATGAAGTTCATCATCAAAAATTGGTGTTCTTTGC AGAAGATGTGGGTTCAAACAAAGGTGCAATCATTGGACTCATGGT GGGCGGTGTTGTCATAGCGACAGTGATCGTCATCACCTTGGTGATG CTGAAGAAGAAACAGTACACATCCATTCATCATGGTGTGGTGGAG GTTGACGCCGCTGTCACCCCAGAGGAGCGCCACCTGTCCAAGATG CAGCAGAACGGCTACGAAAATCCAACCTACAAGTTCTTTGAGCAG ATGCAGAACTAG |

TABLE 1-continued

| SEQ ID NO | Name* | Sequence** |
|---|---|---|
| 2 | cAPP-R3/16-2 | ATGCTGCCCGGTTTGGCACTGCTCCTGCTGGCCGCCTGGACGGCTC<br>GGGCGCTGGAGGTACCCACTGATGGTAATGCTGGCCTGCTGGCTG<br>AACCCCAGATTGCCATGTTCTGTGGCAGACTGAACATGCACATGA<br>ATGTCCAGAATGGGAAGTGGGATTCAGATCCATCAGGGACCAAAA<br>CCTGCATTGATACCAAGGAAGGCATCCTGCAGTATTGCCAAGAAG<br>TCTACCCTGAACTGCAGATCACC:AAGATGGATGCAGAATTCCGAC<br>ATGACTCAGGATATGAAGTTCA<u>T</u>CATCAAAAATTGGTGTTCTTTGC<br>AGAAGATGTGGGTTCAAACAAAGGTGCAATCATTGGACTCATAGT<br>GGGCGGTGTTGTCATAGCGACAGTGATCGTCATCACCTTGGTGATG<br>CTGAAGAAGAAACAGTACACATCCATTCATCATGGTGTGGTGGAG<br>GTTGACGCCGCTGTCACCCCAGAGGAGCGCCACCTGTCCAAGATG<br>CAGCAGAACGGCTACGAAAATCCAACCTACAAGTTCTTTGAGCAG<br>ATGCAGAACTAG |
| 3 | cAPP-R2/18 | ATGCTGCCCGGTTTGGCACTGCTCCTGCTGGCCGCCTGGACGGCTC<br>GGGCGCTGGAGGTACCCACTGATGGTAATGCTGGCCTGCTGGCTG<br>AACCCCAGATTGCCATGTTCTGTGGCAGACTGAACATGCACATGA<br>ATGTCCAGAATGGGAAGTGGGATTCAGATCCATCAGGGACCAAAA<br>CCTGCATTGATACCAAGGAAGGCATCCTG:CGCTACGAAAATCCAA<br>CCTACAAGTTCTTTGAGCAGATGCAGAAC<u>T</u>AG |
| 4 | cAPP-R6/18 | ATGCTGCCCGGTTTGGCACTGCTCCTGCTGGCCGCCTGGACGGCTC<br>GGGCGCTGGAGGTACCCACTGATGGTAATGCTGGCCTGCTGGCTG<br>AACCCCAGATTGCCATGTTCTGTGGCAGACTGAACATGCACATGA<br>ATGTCCAGAATGGGAAGTGGGATTCAGATCCATCAGGGACCAAAA<br>CCTGCATTGATACCAAGGAAGGCATCCTGCAGTATTGCCAAGAAG<br>TCTACCCTGAACTGCAGATCACCAATGTGGTAGAAGCCAACCAAC<br>CAGTGACCATCCAGAACTGGTGCAAGCGGGGCCGCAAGCAGTGCA<br>AGACCCATCCCCACTTTGTGATTCCCTACCGCTGCTTAGTTGGTGA<br>GTTTGTAAGTGATGCCCTTCTCGTTCCTGACAAGTGCAAATTCTTA<br>CACCAGGAGGATGGATGTTTGCGAAACTCATCTTCACTGGCAC<br>ACCGTCGCCAAAGAGACATGCAGTGAGAAGAGTACCAACTTGCAT<br>GACTACGGCATGTTGCTGCCCTGCGGAATTGACAAGTTCCGAGGG<br>GTAGAGTTTGTGTGTTGCCCACTGGCTGAAGAAAGTGACAATGTG<br>GATTCTGCTGATGCGGAGGAGGATGACTCGGATGTCTGGTGGGGC<br>GGAGCAGACACAGACTATGCAGATGGGAGTGAAGACAAAGTAGT<br>AGAAGTAGCAGAGGAGGAAGAAGTGGCTGAGGTGGAAGAAGAAG<br>AAGCCGATGATGACC:GAGGAGCGCCACCTGTCCAAGATGCAGCAG<br>AGCGGCTACGAA<u>A</u>ATCCAACCTACAAGTTCTTTGAGCAGATGCAG<br>AACTAG |
| 5 | cAPP-R3/14 | ATGCTGCCCGGTTTGGCACTGCTCCTGCTGGCCGCCTGGACGGCTC<br>GGGCGCTGGAGGTACCCACTGATGGTAATGCTGGCCTGCTGGCTG<br>AACCCCAGATTGCCATGTTCTGTGGCAGACTGAACATGCACATGA<br>ATGTCCAGAATGGGAAGTGGGATTCAGATCCATCAGGGACCAAAA<br>CCTGCATTGATACCAAGGAAGGCATCCTGCAGTATTGCCAAGAAG<br>TCTACCCTGAACTGCAGATCACCAATGTGGTAGAAGCCAAC:ACAG<br>AAAACGAAGTTGAGCCTGTTGATGCCCGCCCTGCTGCCGA<u>C</u>CGAG<br>GACTGACCACTCGACCAGGTTCTGGGTTGACAAATATCAAGACGG<br>AGGAGATCTCTGAAGTGAAGATGGATGCAGAATTCCGACATGACT<br>CAGGATATGAAGTTCATCATCAAAAATTGGTGTTCTTTACAGAAGA<br>TGTGGGTTCAAACAAAGGTGCAATCATTGGACTCATGGTGGGCGG<br>TGTTGTCATAGCGACAGTGATCGTCATCACCTTGGTGATGCTGAAG<br>AAGAAACAGTACACATCCATTCATCATGGTGTGGTGGAGGTTGAC<br>GCCGCTGTCACCCCAGAGGAGCGCCACCTGTCCAAGATGCAGCAG<br>AACGGCTACGAAAATCCAACCTACAAGTTCTTTGAGCAGATGCAG<br>AACTAG |
| 6 | ncAPP-R3/17 | ATGCTGCCCGGTTTGGCACTGCTCCTGCTGGCCGCCTGGACGGCTC<br>GGGCGCTGGAGATACCCACTGATGGTAATGCTGGCCTGCTGGCTG<br>AACCCCAGATTGCCATGTTCTGTGGCAGACTGAACATGCACATGA<br>ATGTCCAGAATGGGAAGTGGGACTCAGATCCATCAGGGACCAAAA<br>CCTGCATTGATACCAAGGAAGGCATCCTGCAGTATTGCCAAGAAG<br>TCTACCCTGAACTGCAGATCACCAATGTGGTAGAAGCCAACCAAC<br>CAGTGACCATCCAGAACTGGTGCAAGCGGGGCCGCAAGCAGG:TGT<br>TGTCATAGCGACAGTGATCGTCATCACCTTGGTGATGCTG<u>A</u>AGAA<br>GAAACAGTACACATCCATTCATCATGGTGTGGTGGAGGTTGACGC<br>CGCTGTCACCCCAGAGGAGCGCCACCTGTCCAAGATGCAGCAGAA<br>CGGCTACGAAAATCCAACCTACAAGTTCTTTGAGCAGATGCAGAA<br>CTAG |
| 7 | cAPP-R1/11 | ATGCTGCCCGGTTTGGCACTGCTCCTGCTGGCCGCCTGGACG:GCC<br>TCGTCACGTGTTCAATATGCTAAAGAAGTATGTCCGCGCAG<u>A</u>ACA<br>GAAGGACAGACAGCACACCCTAAAGCATTTCGAGCATGTGCGCAT<br>GGTGGATCCCAAGAAAGCCGCTCAGATCCGGTCCCAGGTTATGAC |

TABLE 1-continued

| SEQ ID NO | Name* | Sequence** |
|---|---|---|
| | | ACACCTCCGTGTGATTTATGAGCGCATGAATCAGTCTCTCTCCCTG
CTCTACAACGTGCCTGCAGTGGCCGAGGAGATTCAGGATGAAGTT
GATGAGCTGCTTCAGAAAGAGCAAAACTATTCAGATGACGTCTTG
GCCAACATGATTAGTGAACCAAGGATCAGTTACGGAAACGATGCT
CTCATGCCATCTTTGACCGAAACGAAAACCACCGTGGAGCTCCTTC
CCGTGAATGGAGAGTTCAGCCTGGACGATCTCCAGCCGTGGCATT
CTTTTGGGGCTGACTCTGTGCCAGCCAACACAGAAAACGAAGTTG
AGCCTGTTGATGCCCGCCCTGCTGCCGACCGAGGACTGACCACTCG
ACCAGGTTCTGGGTTGACAAATATCAAGACGGAGGAGATCTCTGA
AGTGAAGATGGATGCAGAATTCCGACATGACTCAGGATATGAAGT
TCATCATCAAAAATTGGTGTTCTTTGCAGAAGATGTGGGTTCAAAC
AAAGGTGCAATCATTGGACTCATGGTGGGTGGTGTTGTCATAGCG
ACAGTGATCGTCATCACCTTGGTGATGCTGAAGAAGAAACAGTAC
ACATCCATTCATCATGGTGTGGTGGAGGTTGACGCCGCTGTCACCC
CAGAGGAGCGCCACCTGTCCAAGATGCAGCAGAACGGCTACGAAA
ATCCAACCTACAAGTTCTTTGAGCAGATGCAGAACTAG |
| 8 | ncAPP-R1/13 | ATGCTGCCCGGTTTGGCACTGCTCCTGCAGTGG:GAGGAGATTCAG
GATGAAGTTGATGAACTGCTTCAGAAAGAGCAAAACTATTCAGAT
GACGTCTTGGCCAACATGATTAGTGAACCAAGGATCAGTTACGGA
AACGATGCTCTCATGCCATCTTTGACCGAAACGAAAACCACCGTG
GAGCTCCTTCCCGTGAATGGAGAGTTCAGCCTGGACGATCTCCAGC
CGTGGCATTCTTTTGGGGCTGACTCTGTGCCAGCCAACACAGAAAA
CGAAGTTGAGCCTGTTGATGCCCGCCCTGCTGCCGACCGAGGACT
GACCACTCGACCAGGTTCTGGGTTGACAAATATCAAGACGGAGGA
GATCTCTGAAGTGAAGATGGATGCAGAATTCCGACATGACTCAGG
ATATGAAGTTCATCATCAAAAATTGGTGTTCTTTGCAGAAGATGTG
GGTTCAAACAAAGGTGCAATCATTGGACTCATGGTGGCGGTGTTG
TCATAGCGACAGTGATCGTCATCACCTTGGTGATGCTGAAGAAGA
AACAGTACACATCCATTCATCATGGTGTGGTGGAGGTTGACGCCG
CTGTCACCCCAGAGGAGCGCCACCTGTCCAAGATGTGGCAGAACG
GCTACGAAAATCCAACCTACAAGTTCTTTGAGCAGATGCAGAACT
AG |
| 9 | ncAPP-R1/11-2 | ATGCTGCCCGGTTTGGCACTGCTC:TGCAGGCTGTTCCTCCTCGGCC
TCGTCACGTGTTCAATATGCTAAAGAAGTATGTCCGCGCAGAACA
GAAGGACAGACAGCACACCCTAAAGCATTTCGAGCATGTGCGCAT
GGTGGATCCCAAGAAAGCCGCTCAGATCCGGTCCCAGGTTATGAC
ACACCTCCGTGTGATTTATGAGCGCATGAATCAGTCTCTCTCCCTG
CTCTACAACGTGCCTGCAGTGGCCGAGGAGATTCAGGATGAAGTT
GATGAGCTGCTTCAGAAAGAGCAAAACTATTCAGATGACGTCTTG
GCCAACATGATTAGTGAACCAAGGATCAGTTACGGAAACGATGCT
CTCATGCCATCTTTGACCGAAACGAAAACCACCGTGGAGCTCCTTC
CCGTGAATGGAGAGTTCAGCCTGGACGATCTCCAGCCGTGGCATT
CTTTTGGGGCTGACTCTGTGCCAGCCAACACAGAAAACGAAGTTG
AGCCTGTTGATGCCCGCCCTGCTGCCGACCGAGGACTGACCACTCG
ACCAGGTTCTGGGTTGACAAATATCAAGACGGAGGAGATCTCTGA
AGTGAAGATGGATGCAGAATTCCGACATGACTCAGGATATGAAGT
TCATCATCAAAAATTGGTGTTCTTTGCAGAAGATGTGGGTTCAAAC
AAAGGTGCAATCATTGGACTCATGGTGGGCGGTGTTGTCATAGCG
ACAGTGATCGTCATCACCTTGGTGATGCTGAAGAAGAAACAGTAC
ACATCCATTCATCATGGTGTGGTGGAGGTTGACGCCGCTGTCACCC
CAGAGGAGCGCCACCTGTCCAAGATGCAGCAGAACGGCTACGAAA
ATCCAACCTACAAGTTCTTTGAGCAGATGCAGAACTAG |
| 10 | ncAPP-R1/14 | ATGCTGCCCGGTTTGGCACTGCTCCTGCTGGCCGCCTGGACAGCT:CCTTCCCGTGAATGGAGAGTTCAGCCTGGACGATCTCCAGCCGTG
GCATTCTTTTGGGGCTGACTCTGTGCCAGCCAACACAGAAAACGA
AGTTGAGCCTGTTGATGCCCGCCCTGCTGCCGACCGAGGACTGACC
ACTCGACCAGGTTCTGGGTTGACAAATATCAAGACGGAGGAGATC
TCTGAAGTGAAGATGGATGCAGAATTCCGACATGACTCAGGATAT
GAAGTTCATCATCAAAAATTGGTGTTCTTTGCAGAAGATGTGGGTT
CAAACAAAGGTGCAATCATTGGACTCATGGTGGGCGGTGTTGTCA
TAGCGACAGTGATCGTCATCACCTTGGTGATGCTGAAGAAGAAAC
AGTACACATCCATTCATCATGGTGTGGTGGAGGTTGACGCCGCTGT
CACCCCAGAGGAGCGCCACCTGTCCAAGATGCAGCAGAACGGCTA
CGAAAATCCAACCTACAAGTTCTTTGAGCAGATGCAGAACTAG |
| 11 | ncAPP-R2/17 | ATGCTGCCCGGTTTGGCACTGCTCCTGCTGGCCGCCTGGACGGCTC
GGGCGCTGGAGGTACCC:AATCATTGGACTCATGGTGGCGGTGTT
GTCATAGCGACAGTGATCGTCATCACCTTGGTGATGCTGAAGAAG
AAACAGTACACATCCATTCATCATGGTGTGGTGGAGGTTGACGCC
GCTGTCACCCCAGAGGAGCGCCACCTGTCCAAGATGCAGCAGAAC
GGCTACGAAAATCCAACCTACAAGTTCTTTGAGCAGATGCAGAAC
TAG |

TABLE 1-continued

| SEQ ID NO | Name* | Sequence** |
|---|---|---|
| 12 | cAPP-R2/16 | ATGCTGCCCGGTTTGGCACTGCTCCTGCTGGCCGCCTGGACGGCTC GGGCGCTGGAGGTACCCACTGATGGTAATGCTGGCCTGCTGGCTG AACCCCAGATTGCCATGTTCTGTGGCAGACTGAACATGCACATGA ATGTCCAGAATGGGAAGTGGGATTCAGATCCATCAGGGACCAAAA CCTGCATTGATACCAAGGAAGGCATCCTGCAGTAT:ATGCAGAATT CCGACATGACTCAGGATATGAAGTTCATCATCAAAAATTGGTGTTC TTTGCAGAAGATGTGGGTTCAAACAAAGGTGCAATCATTGGACTC ATGGTGGGCGGTGTTGTCATAGCGACAGTGATCGTCATCACCTTGG TGATGCTGAAGAAGAAACAGTACACATCCATTCATCATGGTGTGG TGGAGGTTGACGCCGCTGTCACCCCAGAGGAGCGCCACCTGTCCA AGATGCAGCAGAACGGCTACGAAAATCCAACCTACAAGTTCTTTG AGCAGATGCAGAACTAG |
| 13 | cAPP-R6/17 | ATGCTGCCCGGTTTGGCACTGCTCCTGCTGGCCGCCTGGACGGCTC GGGCGCTGGAGGTACCCACTGATGGTAATGCTGGCCTGCTGGCTG AACCCCAGATTGCCATGTTCTGTGGCAGACTGAACATGCACATGA ATGTCCAGAATGGGAAGTGGGATTCAGATCCATCAGGGACCAAAA CCTGCATTGATACCAAGGAAGGCATCCTGCAGTATTGCCAAGAAG TCTACCCTGAACTGCAGATCACCAATGTGGTAGAAGCCAACCAAC CAGTGACCATCCAGAACTGGTGCAAGCGGGGCCGCAAGCAGTGCA AGACCCATCCCCACTTTGTGATTCCCTACCGCTGCTTAGTTGGTGA GTTTGTAAGTGATGCCCTTCTCGTTCCTGACAAGTGCAAATTCTTA CACCAGGAGAGGATGGATGTTTGCGAAACTCATCTTCACTGGCAC ACCGTCGCAAAGAGACATGCAGTGAGAAGAGTACCAACTTGCAT GACTACGGCATGTTGCTGCCCTGCGGAATTGACAAGTTCCGAGGG GTAGAGTTTGTGTGTTGCCCACTGGCTGAAGAAAGTGACAATGTG GATTCTGCTGATGCGGAGGAGGATGACTCGGATGTCTGGTGGGGC GGAGCAGACACAGACTATGCAGATGGGAGTGAAGACAAA:GGTGC AATCATTGGACTCATGGTGGGCGGTGTTGTCATAGCGACAGTGATC GTCATCACCTTGGTGATGCTGAAGAAGAAACAGTACACATCCATT CATCATGGTGTGGTGGAGGTTGACGCCGCTGTCACCCCAGAGGAG CGCCACCTGTCCAAGATGCAGCAGAACGGCTACGAAAATCCAACC TACAAGTTCTTTGAGCAGATGCAGAACTAG |
| 14 | ncAPP-R2/14 | ATGCTGCCCGGTTTGGCACTGCTCCTGCTGGCCGCCTGGACGGCTC GGGCGCTGGAGGTACCCACTGATGGTAATGCTGGCCTGCTGGCTG AACCCCAGATTGCCATGTTCTGTGGCAGACTGAACATGCACATGA ATGTCCAGAATGGGAAGTGGGATTCAGATCCATCAGGGACCAAAA CCTGCATTGATACCAAG:GATCAGTTACGGAAACGATGCTCTCATG CCATCTTTGACCGAAACGAAAACCACCGTGGAGCTCCTTCCCGTGA ATGGAGAGTTCAGCCTGGACGATCTCCAGCCGTGGCATTCTTTTGG GGCTGACTCTGTGCCAGCCAACACAGAAAACGAAGTTGAGCCTGT TGATGCCCGCCCTGCTGCCGACCGAGGACTGACCACTCGACCAGG TTCTGGGTTGACAAATATCAAGACGGAGGAGATCTCTGAAGTGAA GATGGATGCAGAATTCCGACATGACTCAGGATATGAAGTTCATCA TCAAAAATTGGTGTTCTTTGCAGAAGATGTGGGTTCAAACAAAGG TGCAATCATTGGACTCATGGTGGGCGGTGTTGTCATAGCGACAGTG ATCGTCATCACCTTGGTGATGCTGAAGAAGAAACAGTACACATCC ATTCATCATGGTGTGGTGGAGGTTGACGCCGCTGTCACCCCAGAG GAGCGCCACCTGTCCAAGATGCAGCAGAACGGCTACGAAAATCCA ACCTACAAGTTCTTTGAGCAGATGCAGAACTAG |
| 15 | ncAPP-R14/17-d8 | ATGCTGCCCGGTTTGGCACTGCTCCTGCTGGCCGCCTGGACGGCTC GGGCGCTGGAGGTACCCACTGATGGTAATGCTGGCCTGCTGGCTG AACCCCAGATTGCCATGTTCTGTGGCAGACTGAACATGCACATGA ATGTCCAGAATGGGAAGTGGGATTCAGATCCATCAGGGACCAAAA CCTGCATTGATACCAAGGAAGGCATCCTGCAGTATTGCCAAGAAG TCTACCCTGAACTGCAGATCACCAATGTGGTAGAAGCCAACCAAC CAGTGACCATCCAGAACTGGTGCAAGCGGGGCCGCAAGCAGTGCA AGACCCATCCCCACTTTGTGATTCCCTACCGCTGCTTAGTTGGTGA GTTTGTAAGTGATGCCCTTCTCGTTCCTGACAAGTGCAAATTCTTA CACCAGGAGAGGATGGATGTTTGCGAAACTCATCTTCACTGGCAC ACCGTCGCAAAGAGACATGCAGTGAGAAGAGTACCAACTTGCAT GACTACGCATGTTGCTGCCCTGCGAATTGACAAGTTCCGAGGG GTAGAGTTTGTGTGTTGCCCACTGGCTGAAGAAAGTGACAATGTG GATTCTGCTGATGCGGAGGAGGATGACTCGGATGTCTGGTGGGGC GGAGCAGACACAGACTATGCAGATGGGAGTGAAGACAAAGTAGT AGAAGTAGCAGAGGAGGAAGAAGTGGCTGAGGTGGAAGAAGAAG AAGCCGATGATGACGAGGACGATGAGGATGGTGATGAGGTAGAG GAAGAGGCTGAGGAACCCTACGAAGAAGCCACAGAGAGAACCAC CAGCATTGCCACCACCACCACCACCACCACCACCACCACAGAGTCTGTGGAAGA GGTGGTTCGAGAGGTGTGCTCTGAACAAGCCGAGCGGGGCCGTG CCGAGCAATGATCTCCCGCTGGTACTTTGATGTGACTGAAGGGAA GTGTGCCCCATTCTTTTACGCGCGGATGTGGCGGCAACCGGAACAA CTTTGACACAGAAGAGTACTGCATGGCCGTGTGTGGCAGCGCCAT TCCTACAACAGCAGCCAGTACCCCTGATGCCGTTGACAAGTATCTC |

TABLE 1-continued

| SEQ ID NO | Name* | Sequence** |
|---|---|---|
| | | GAGACACCTGGGGATGAGAATGAACATGCCCATTTCCAGAAAGCC<br>AAAGAGAGGCTTGAGGCCAAGCACCGAGAGAGAATGTCCCAGGT<br>CATGAGAGAATGGGAAGAGGCAGAACGTCAAGCAAAGAACTTGC<br>CTAAAGCTGATAAGAAGGCAGTTATCCAGCATTTCCAGGAGAAAG<br>TGGAATCTTTGGAACAGGAAGCAGCCAACGAGAGACAGCAGCTGG<br>TGGAGACACACATGGCCAGAGTGGAAGCCATGCTCAATGACCGCC<br>GCCGCCTGGCCCTGGAGAACTACATCACCGCTCTGCAGGCTGTTCC<br>TCCTCGGCCTCGTCACGTGTTCAATATGCTAAAGAAGTATGTACGC<br>GCAGAACAGAAGGACAGACAGCACACCCTAAAGCATTTCGAGCAT<br>GTGCGCATGGTGGATCCCAAGAAAGCCGCTCAGATCCGGTCCCAG<br>GTTATGACACTCCTCCGTGTGATTTATGAGCGCATGAATCAGTCTC<br>TCTCCCTGCTCTACAACGTGCCTGCAGTGGCCGAGGAGATTCAGGA<br>TGAAGTTGGT:GTTCTTTGCAGAAGATGTGGGTTCAAACAAAGGTG<br>CAATCATTGGACTCATGGTGGGCGGTGTTGTCATAGCGACAGTGAT<br>CGTCATCACCTTGGTGATGCTGAAGAAGAAACAGTACACATCCAT<br>TCATCATGGTGTGGTGGAGGTTGACGCCGCTGTCACCCCAGAGGA<br>GCGCCACCTGTCCAAGATGCAGCAGAACGGCTACGAAAATCCAAC<br>CTACAAGTTCTTTGAGCAGATGCAGAACTAG |
| 16 | cAPP-<br>D2/18-3 | ATGCTGCCCGGTTTGGCACTGCTCCTGCTGGCCGCCTGGACGGCTC<br>GGGCGCTGGAGGTACCCACTGATGGTAATGCTGGCCTGCTGGCTG<br>AACCCCAGATTGCCATGTTCTGTGGCAGA:AAGTTCTTTGAGCAGA<br>TGCAGAAC |

*Nomenclature: c, coding; nc, non-coding; R, RNA; D, DNA; X/Y, junction between exon X/Y; -X, number of variants.
**X:Y indicate intraexonic junctions In certain embodiments, the non-classical variants of APP comprise one or more single nucleotide variation (SNV). In some embodiments, the SNV is known to be associated with familial mutations that arise somatically. In some embodiments, the SNV is known to be associated with pathogenic Alzheimer's disease. Exemplary familial mutations associated with pathogenic Alzheimer's disease which translate to amino acid positions in APP protein include, but are not limited to, K670, M671, A673, D678, E682, K687, A692, E693, D694, A713, T714, V715, I716, V717, T719, M722, L723, and K724, wherein the amino acids correspond to positions 670, 671, 673, 678, 682, 687, 692, 693, 694, 713, 714, 715, 716, 717, 719, 722, 723, and 724 of SEQ ID NO: 17. In some embodiments, the mutation which translates to amino acid positions in APP protein include, but are not limited to, A201, A235, D243, E246, E296, P299, R468H, A479, K496, A500, Y538, V562, E599, T600, P620, T663, E665, K670, M671, A673, H677, D678, E682, K687, A692, E693, D694, G709, A713, T714, V715, I716, V717, T719, M722, L723, K724, and H733 wherein the amino acids correspond to positions 201, 235, 243, 246, 296, 299, 468, 479, 496, 500, 538, 562, 599, 600, 620, 663, 665, 670, 671, 673, 677, 678, 682, 687, 692, 693, 694, 709, 713, 714, 715, 716, 717, 719, 722, 723, 724, and 733 of SEQ ID NO: 17. In some embodiments, the SNV in APP, which translate to amino acid positions in APP protein include, but are not limited to, K670N, M671L, A673V, D678H, D678N, E682K, K687N, A692G, E693G, D694N, A713T, T714A, T714I, V715A, V715M, I716F, I716M, I716T, I716V, V717F, V717G, V717I, V717L, T719P, M722K, L723P, and K724N. In some embodiments, the SNV in APP, which translate to amino acid positions in APP protein include, but are not limited to, A201V, A235V, D243N, E246K, E296K, P299L, R468H, A479S , K496Q, A500T, Y538H, V562I, E599K, T600M, P620A, P620L, T663M, E665D, K670N, M671L, A673T, A673V, H677R, D678H, D678N, E682K, K687N, A692G, E693G, D694N, G709S, A713T, A713V, T714A, T714I, V715A, V715M, I716F, I716M, I716T, I716V, V717F, V717G, V717I, V717L, T719P, M722K, L723P, K724N, and H733P.

In some embodiments, the non-classical variants comprise a SNV in one or more exon of APP. In some embodiments, the non-classical variants comprise the SNV in exon 1, 2, 3, 4, 5, 6, 7, 8, 9, 10, 11, 12, 13, 14, 15, 16, 17, 18,or combinations thereof of APP. In some embodiments, the non-classical variants comprise the SNV in exon 17. In some embodiments, the non-classical variants comprise the SNV in the amyloid beta region of APP. In some embodiments, the SNV in APP, which translates to amino acid positions in APP protein includes, but are not limited to, K670, M671, A673, D678, E682, K687, A692, E693, D694, A713, T714, V715, I716, V717, T719, M722, L723, and K724, wherein the amino acids correspond to positions 670, 671, 673, 678, 682, 687, 692, 693, 694, 713, 714, 715, 716, 717, 719, 722, 723, and 724 of SEQ ID NO: 17. In some embodiments, the SNV in APP, which translates to amino acid positions in APP includes, but are not limited to, A673, A713, T714, V715, I716, V717, T719, and L723, wherein the amino acids correspond to positions 673, 713, 714, 715, 716, 717, 719, and 723 of SEQ ID NO: 17. In some embodiments, the SNV in APP, which translates to amino acid positions in APP includes, but are not limited to, K670N, M671L, A673V, D678H, D678N, E682K, K687N, A692G, E693G, D694N, A713T, T714A, T714I, V715A, V715M, I716F, I716M, I716T, I716V, V717F, V717G, V717I, V717L, T719P, M722K, L723P, and K724N. In some embodiments, the SNV in APP, which translates to amino acid positions in APP includes, but are not limited to, A673V, A713T, T714I, V715M, V715A, I716M, V717I, V717F, T719P, and L723P. In some embodiments, the SNV in APP, which translates to amino acid positions in APP includes, but are not limited to, A201, A235, D243, E246, E296, P299, R468H, A479, K496, A500, Y538, V562, E599, T600, P620, T663, E665, K670, M671, A673, H677, D678, E682, K687, A692, E693, D694, G709, A713, T714, V715, I716, V717, T719, M722, L723, K724, and H733 wherein the amino acids correspond to positions 201, 235, 243, 246, 296, 299, 468, 479, 496, 500, 538, 562, 599, 600, 620, 663, 665, 670, 671, 673, 677, 678, 682, 687, 692, 693, 694, 709, 713, 714, 715, 716, 717, 719, 722, 723, 724, and 733 of SEQ ID NO: 17. In some embodiments, the SNV in APP, which translates to amino acid positions in APP includes, but are not limited to, A201V, A235V, D243N, E246K, E296K, P299L, R468H, A479S, K496Q, A500T, Y538H, V562I, E599K, T600M, P620A, P620L, T663M, E665D, K670N, M671L, A673T, A673V, H677R, D678H, D678N, E682K, K687N, A692G, E693G, D694N, G709S, A713T, A713V, T714A, T714I, V715A, V715M, I716F, I716M, I716T, I716V, V717F, V717G, V717I, V717L, T719P, M722K, L723P, K724N, and H733P.

TABLE 2

Amino Acid Sequence of APP

| SEQ ID NO | Accession No. | Amino Acid Sequence |
|---|---|---|
| 17 | P05067.3 | MLPGLALLLLAAWTARALEVPTDGNAGLLAEPQIAMFCGRLN MHMNVQNGKWDSDPSGTKTCIDTKEGILQYCQEVYPELQITN VVEANQPVTIQNWCKRGRKQCKTHPHFVIPYRCLVGEFVSDAL LVPDKCKFLHQERMDVCETHLHWHTVAKETCSEKSTNLHDYG MLLPCGIDKFRGVEFVCCPLAEESDNVDSADAEEDDSDVWWG GADTDYADGSEDKVVEVAEEEEVAEVEEEEADDDEDDEDGDE VEEEAEEPYEEATERTTSIATTTTTTTESVEEVVREVCSEQAETG PCRAMISRWYFDVTEGKCAPFFYGGCGGNRNNFDTEEYCMAV CGSAMSQSLLKTTQEPLARDPVKLPTTAASTPDAVDKYLETPG DENEHAHFQKAKERLEAKHRERMSQVMREWEEAERQAKNLP KADKKAVIQHFQEKVESLEQEAANERQQLVETHMARVEAMLN DRRRLALENYITALQAVPPRPRHVFNMLKKYVRAEQKDRQHT LKHFEHVRMVDPKKAAQIRSQVMTHLRVIYERMNQSLSLLYN VPAVAEEIQDEVDELLQKEQNYSDDVLANMISEPRISYGNDAL MPSLTETKTTVELLPVNGEFSLDDLQPWHSFGADSVPANTENE VEPVDARPAADRGLTTRPGSGLTNIKTEEISEVKMDAEFRHDSG YEVHHQKLVFFAEDVGSNKGAIIGLMVGGVVIATVIVITLVML KKKQYTSIHHGVVEVDAAVTPEERHLSKMQQNGYENPTYKFF EQMQN |

In some embodiments, the non-classical variant of APP comprises a sequence as set forth in SEQ ID NO: 1, 2, 3, 4, 5, 6, 7, 8, 9, 10, 11, 12, 13, 14, 15, or 16. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 1. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 2. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 3. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 4. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 5. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 6. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 7. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 8. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 9. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 10. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 11. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 12. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 13. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 14. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 15. In some embodiments, the non-classical variant of APP comprises at least or about 70%, 80%, 85%, 90%, 91%, 92%, 93%, 94%, 95%, 96%, 97%, 98%, 99%, or 100% sequence identity to SEQ ID NO: 16.

Reverse Transcriptase Inhibitors and Method of Treatment Using the Reverse Transcriptase Inhibitors The inventors contemplate that at least some non-classical variants of APP are generated by an enzyme having a reverse transcriptase activity. In some embodiments, the enzyme having a reverse transcriptase activity can be a DNA polymerase, an RNA-dependent DNA polymerase, or a DNA-dependent DNA polymerase. Additionally and/or alternatively, the enzyme having a reverse transcriptase activity or the reverse transcriptase activity can be brain-specific, sub-region-specific (e.g., cortex, etc.), cell type-specific (e.g., neuron-specific), and/or neuron type-specific (e.g., hippocampal neuron-specific, cortical neuron-specific, etc.).

Consequently, the inventors contemplate that generation of one or more non-classical variant(s) of an amyloid precursor protein (APP) gene in a subject (e.g., an individual having or suspected to have AD, an individual having or suspected to beta amyloid plaque or accumulation of beta amyloid aggregates in the brain, etc.) can be inhibited, suppressed, or reduced by providing (or treating) a reverse transcriptase inhibitor inhibiting the reverse transcriptase activity of an enzyme (e.g., DNA polymerase, RNA-dependent DNA polymerase, DNA-dependent DNA polymerase, etc.) to the subject.

In some embodiments, the reverse transcriptase inhibitor inhibits activity of a reverse transcriptase. In some embodiments, the reverse transcriptase inhibitor inhibits expression of a reverse transcriptase. In some embodiments, the reverse transcriptase inhibitor inhibits formation of complementary DNA from a template RNA by a reverse transcriptase. For example, the reverse transcriptase inhibitor inhibits reverse transcriptase activity by suicide, competitive inhibition, non-competitive inhibition, and allosteric inhibition, binding to a non-nucleoside pocket, depletion of nucleosides for DNA synthesis, or induction or contribution to conformational changes.

In some embodiments, the reverse transcriptase inhibitor inhibits activity of a brain-specific reverse transcriptase. In some embodiments, the reverse transcriptase inhibitor inhibits activity of a cell-type specific reverse transcriptase. In some embodiments, the cell-type specific reverse transcriptase is specific to a cell-type in the brain including, but not limited to, neurons, astrocytes, microglia, or oligodendrocytes. In some embodiments, the reverse transcriptase inhibitor is capable of penetrating the blood-brain barrier.

In some embodiments, the reverse transcriptase is a retroviral reverse transcriptase. In some embodiments, the reverse transcriptase is a non-retroviral reverse transcriptase. Exemplary reverse transcriptases include, but are not limited to, retroviral reverse transcriptase, retrotransposon reverse transcriptase, retroplasmid reverse transcriptase, retron reverse transcriptase, bacterial reverse transcriptase, group II intron-derived reverse transcriptase, non-long terminal repeat (LTR) retrotransposon reverse transcriptase, retroplasmid reverse transcriptase, retron reverse transcriptase, group II intron reverse transcriptase, variants or derivatives thereof. In some embodiments, the reverse transcriptase is telomerase reverse transcriptase (TERT), human endogenous retrovirus type K (HERV-K), LINE-1 retrotransposable element ORF2, or human immunodeficiency virus type 1 reverse transcriptase.

Any suitable types of reverse transcriptase inhibitor that can effectively inhibit the reverse transcriptase are contemplated. For example, the reverse transcriptase inhibitor can be an antibody, an antigen binding fragment, a RNA interfering agent (RNAi), a small interfering RNA (siRNA), a short hairpin RNA (shRNA), a microRNA (miRNA), an antisense oligonucleotide, a peptide, a peptidomimetic, a small molecule, or an aptamer. Exemplary antibodies include, but are not limited to, a monoclonal antibody, a polyclonal antibody, a bi-specific antibody, a multispecific antibody, a grafted antibody, a human antibody, a humanized antibody, a synthetic antibody, a chimeric antibody, a camelized antibody, a single-chain Fvs (scFv), a single chain antibody, a Fab fragment, a F(ab') fragment, disulfide-linked Fvs (sdFv), an intrabody, an anti-idiotypic (anti-Id) antibody, or ab antigen-binding fragments thereof. In some embodiments, the antibody comprises immunoglobulin molecules and immunologically active fragments of immunoglobulin molecules, e.g., molecules that contain an antigen binding site. Immunoglobulin molecules are of any type, class (e.g., IgG, IgE, IgM, IgD, IgA and IgY), or subclass (e.g., IgG1, IgG2, IgG3, IgG4, IgA1 and IgA2). In some embodiments, the reverse transcriptase inhibitor is a single-domain antibody. In some embodiments, the reverse transcriptase inhibitor is a nanobody. In some embodiments, the reverse transcriptase inhibitor is a synthetic nanobody, a derivative of a nanobody, or a combination thereof. In some embodiments, the reverse transcriptase inhibitor is a synthetically evolved nanobody (SEN).

In some embodiments, the antibody selectively binds to a reverse transcriptase. "Selectively binds" refers to the preference of an antibody to interact with one molecule as compared to another. In some embodiments, the antibody specifically binds to reverse transcriptase. The phrase "specifically binds" when referring to the interaction between an antibody or other binding molecule and a protein or polypeptide or epitope, typically refers to an antibody or other binding molecule that recognizes and detectably binds with high affinity to the target of interest. Preferably, under designated or physiological conditions, the specified antibodies or binding molecules bind to a particular polypeptide, protein or epitope yet does not bind in a significant or undesirable amount to other molecules present in a biological sample. For example, the specified antibody or binding molecule does not undesirably cross-react with non-target antigens and/or epitopes.

In some embodiments, the reverse transcriptase inhibitor decreases reverse transcriptase protein stability. In some embodiments, the reverse transcriptase inhibitor is a small molecule. In some embodiments, the small molecule is an antagonist of the reverse transcriptase. In some embodiments, the small molecule inhibits expression of the reverse transcriptase. In some embodiments, the small molecule inhibits activity of the reverse transcriptase.

In some embodiments, the reverse transcriptase inhibitor is a nucleoside-type reverse transcriptase inhibitor. In some embodiments, the reverse transcriptase inhibitor may comprise one or more: azidothymidine (also known as, zidovudine), didanosine, stavudine, lamivudine, abacavir, tenofovir, lamivudine/zidovudine, lamivudine/zidovudine/abacavir, lamivudine/tenofovir disoproxil fumarate, emtricitabine, emtricitabine/tenofovir alafenamide, emtricitabine/tenofovir disoproxil fumarate, tenofovir disoproixl fumarate, abacavir/lamivudine, and/or any combinations thereof. In some embodiments, the reverse transcriptase inhibitor is a derivative of azidothymidine, didanosine, stavudine, lamivudine, abacavir, tenofovir, or emtricitabine. In some embodiments, the reverse transcriptase inhibitor is a non-nucleoside reverse transcriptase inhibitor. In some embodiments, the reverse transcriptase inhibitor is selected from: nevirapine, delavirdine, efavirenz, etravirine, and rilpivirine. In some embodiments, the reverse transcriptase inhibitor is a derivative of nevirapine, delavirdine, efavirenz, etravirine, or rilpivirine.

In some embodiments, the reverse transcriptase inhibitor comprises an antisense RNA that hybridizes to a target RNA and inhibits the activity. In some embodiments, the antisense RNA stringently hybridizes to the target RNA and inhibits the activity. In some embodiments, the target RNA is RNA of the reverse transcriptase gene. Exemplary antisense RNA molecules include, but are not limited to, RNAi, siRNA, shRNA, or miRNA. In some embodiments, the antisense RNA is double stranded or single stranded. In some embodiments, the antisense RNA comprises about 1 to about 50 nucleotides. In some embodiments, the antisense RNA comprises about 5 to about, about 5 to about 30, about 10 to about 30, about 15 to about 25, or about 20 to about 25 nucleotides. In some embodiments, the antisense RNA is at least or about 70%, 75%, 80%, 85%, 90%, 95%, 98%, 99%, or 100% complementary to the target RNA.

In some embodiments, the antisense RNA inhibits activity of the reverse transcriptase gene. For example, the antisense RNA is a double-stranded antisense RNA molecule (e.g., siRNA, miRNA, shRNA) that down-regulates expression of the reverse transcriptase gene, wherein one of the strands of the double-stranded antisense RNA molecule comprises a nucleotide sequence that is complementary to a nucleotide sequence of the reverse transcriptase RNA encoded by the reverse transcriptase or a portion thereof, and wherein the second strand of the double-stranded antisense RNA molecule comprises a nucleotide sequence substantially similar to the nucleotide sequence of reverse transcriptase or RNA encoded by the reverse transcriptase or a portion thereof. In some embodiments, the antisense RNA is a double-stranded antisense RNA molecule that down-regulates expression of the reverse transcriptase gene, wherein each strand of the antisense RNA molecule comprises about 15 to 25, 18 to 24, or 19 to about 23 nucleotides, and wherein each strand comprises at least about 14, 17, or 19 nucleotides that are complementary to the nucleotides of the other strand. In some embodiments, the antisense RNA is a double-stranded antisense RNA molecule that down-regulates expression of the reverse transcriptase gene, wherein each strand of the antisense RNA molecule comprises about 19 to about 23 nucleotides, and wherein each strand comprises at least about 19 nucleotides that are complementary to the nucleotides of the other strand. In some embodiments, the RNA interfering activity occurs within a cell. In other embodiments, the RNA interfering activity occurs in a reconstituted in vitro system.

In some embodiments, the antisense RNA is a single-stranded antisense RNA molecule that down-regulates expression of the reverse transcriptase gene, wherein the single-stranded antisense RNA molecule comprises a nucleotide sequence that is complementary to a nucleotide sequence of reverse transcriptase or RNA encoded by the reverse transcriptase gene or a portion thereof. In some embodiments, antisense RNA is a single-stranded antisense RNA molecule that down-regulates expression of the reverse transcriptase gene, wherein the antisense RNA molecule comprises about 15 to 25, 18 to 24, or 19 to about 23 nucleotides. In some embodiments, antisense RNA molecule is a single-stranded antisense RNA molecule that down-regulates expression of the reverse transcriptase, wherein the antisense RNA molecule comprises about 19 to about 23 nucleotides. In some embodiments, the RNA interfering activity occurs within a cell. In other embodiments, the RNA interfering activity occurs in a reconstituted in vitro system.

In some embodiments, the antisense RNA molecule is a double-stranded polynucleotide molecule comprising self-complementary sense and antisense regions, wherein the antisense region comprises a nucleotide sequence that is complementary to a nucleotide sequence in a target nucleic acid molecule or a portion thereof and the sense region has a nucleotide sequence corresponding to the target nucleic acid sequence or a portion thereof. In some embodiments, the antisense RNA molecule is assembled from two separate polynucleotides, where one strand is the sense strand and the other is the antisense strand, wherein the antisense and sense strands are self-complementary (e.g., each strand comprises a nucleotide sequence that is complementary to the nucleotide sequence in the other strand; such as where the antisense strand and sense strand form a duplex or double-stranded structure, for example wherein the double-stranded region is about 19, 20, 21, 22, 23, or more base pairs); the antisense strand comprises a nucleotide sequence that is complementary to a nucleotide sequence in a target nucleic acid molecule or a portion thereof and the sense strand comprises a nucleotide sequence corresponding to the target nucleic acid sequence or a portion thereof. In some embodiments, the antisense RNA molecule is assembled from a single oligonucleotide, where the self-complementary sense and antisense regions of the antisense RNA molecule are linked by means of a nucleic acid based or non-nucleic acid-based linker(s).

In some embodiments, the antisense RNA molecule is a polynucleotide with a duplex, asymmetric duplex, hairpin, or asymmetric hairpin secondary structure, having self-complementary sense and antisense regions, wherein the antisense region comprises a nucleotide sequence that is complementary to a nucleotide sequence in a separate target nucleic acid molecule or a portion thereof and the sense region has a nucleotide sequence corresponding to the target nucleic acid sequence or a portion thereof. In other embodiments, the antisense RNA molecule is a circular single-stranded polynucleotide having two or more loop structures and a stem comprising self-complementary sense and antisense regions, wherein the antisense region comprises a nucleotide sequence that is complementary to a nucleotide sequence in a target nucleic acid molecule or a portion thereof and the sense region has a nucleotide sequence corresponding to the target nucleic acid sequence or a portion thereof, and wherein the circular polynucleotide is processed either in vivo or in vitro to generate an active antisense RNA molecule capable of mediating RNA interfering activity. In additional embodiments, the antisense RNA molecule also comprises a single-stranded polynucleotide having a nucleotide sequence complementary to a nucleotide sequence in a target nucleic acid molecule or a portion thereof, wherein the single stranded polynucleotide further comprises a terminal phosphate group, such as a 5'-phosphate, or 5',3'-diphosphate.

In some embodiments, an asymmetric duplex is a linear antisense RNA molecule comprising an antisense region, a loop portion that comprises nucleotides or non-nucleotides, and a sense region that comprises fewer nucleotides than the antisense region to the extent that the sense region has enough complementary nucleotides to base pair with the antisense region and form a duplex with loop. For example, an asymmetric hairpin antisense RNA molecule comprises an antisense region having length sufficient to mediate RNA interfering activity in a cell or in vitro system (e.g., about 19 to about 22 nucleotides) and a loop region comprising about 4 to about 8 nucleotides, and a sense region having about 3 to about 18 nucleotides that are complementary to the antisense region. In some embodiments, the asymmetric hairpin the antisense RNA molecule also comprises a 5'-terminal phosphate group that is chemically modified. In additional embodiments, the loop portion of the asymmetric hairpin antisense RNA molecule comprises nucleotides, non-nucleotides, linker molecules, or conjugate molecules.

In some embodiments, an asymmetric duplex is an antisense RNA molecule having two separate strands comprising a sense region and an antisense region, wherein the sense region comprises fewer nucleotides than the antisense region to the extent that the sense region has enough complimentary nucleotides to base pair with the antisense region and form a duplex. For example, an asymmetric duplex antisense RNA molecule comprises an antisense region having length sufficient to mediate RNA interfering activity in a cell or in vitro system (e.g., about 19 to about 22 nucleotides) and a sense region having about 3 to about 18 nucleotides that are complementary to the antisense region.

In some embodiments, an antisense RNA inhibits activity of a target RNA in a cleavage-dependent process. For example, the cleavage-dependent process involves the RNA-induced silencing complex (RISC). In some embodiments, the antisense RNA (e.g., siRNA) comprises a passenger strand and guide strand. The guide strand pairs with a complementary sequence in a mRNA molecule and induces cleavage by an RNase H endonuclease of the RISC complex. In some embodiments, the RNase H endonuclease is Argonaute. In some embodiments, an antisense RNA inhibits activity in a cleavage-independent process. For example, the antisense RNA (e.g., miRNA) comprises nucleotide mismatches with their targets and effect gene silencing through translational repression of the target gene.

In some embodiments, an antisense RNA inhibits the reverse transcriptase gene, pre-mRNA, or mature mRNA. In some embodiments, the antisense RNA alters various functions of the target RNA. In some embodiments, the antisense RNA alters splicing of the RNA to yield one or more mRNA species. In some embodiments, the antisense RNA alters translation of protein from RNA. In some embodiments, the antisense RNA alters translocation of the RNA to the site of protein translation. In some embodiments, the antisense RNA alters a catalytic activity of the RNA or which is facilitated by the RNA. Alternatively or in combination, the antisense RNA reduces an amount of pre-mRNA.

In some embodiments, the reverse transcriptase inhibitor is a sense RNA molecule. In some embodiments, the sense RNA is double stranded or single stranded. In some embodiments, the sense RNA comprises about 1 to about 50 nucleotides. In some embodiments, the sense RNA comprises about 5 to about, about 5 to about 30, about 10 to about 30, about 15 to about 25, or about 20 to about 25 nucleotides. In some embodiments, the sense RNA is at least or about 70%, 75%, 80%, 85%, 90%, 95%, 98%, 99%, or 100% complementary to the target RNA.

In some embodiments, the agent is an antisense oligonucleotide (AON). In some embodiments, the AON comprises antisense oligonucleotide strands. In some embodiments, the AON comprises sense oligonucleotide strands. In some embodiments, the AON comprises antisense oligonucleotide strands and sense oligonucleotide strands. In some embodiments, the AON targets RNA of the reverse transcriptase gene. In some embodiments, the RNA is pre-mRNA. In some embodiments, the RNA is mRNA. In some embodiments, the AON targets DNA of the reverse transcriptase gene.

Antisense oligonucleotides (AONs), in some embodiments, inhibit the expression of the reverse transcriptase gene. In some embodiments, the AONs inhibit the activity of the reverse transcriptase gene. In some embodiments, the AONs inhibit the expression or activity of the reverse transcriptase gene by targeting RNA of the reverse transcriptase gene for degradation. In some embodiments, the AONs inhibit the reverse transcriptase and subsequently inhibit reverse transcription of APP and incorporation of the one or more non-classical variants of APP into the genome. In some embodiments, the reverse transcriptase has RNA-dependent DNA polymerase activity or DNA-dependent DNA polymerase activity. In some embodiments, the AONs inhibit the RNA-dependent DNA polymerase activity or DNA-dependent DNA polymerase activity.

In some embodiments, the antisense oligonucleotide (AON) comprises a nucleobase that is unmodified such as adenine, guanine, cytosine, thymine, and uracil or any synthetic or modified nucleobase. Examples of modified nucleobases include, without limitation, hypoxanthine, xanthine, 7-methylguanine, 5,6-dihydrouracil, 5-methylcytosine, and 5-hydroxymethoylcytosine.

In some embodiments, the antisense oligonucleotide (AON) comprises a backbone that connects components of the AON. In some embodiments, the backbone comprises a 3'-5' phosphodiester linkage connecting sugar moieties of the AON. Examples of a backbone structure or linkages of the AON, include, but are not limited to, phosphorothioate, phosphorodithioate, phosphoroselenoate, phosphorodiselenoate, phosphoroanilothioate, phosphoraniladate, and phosphoramidate. In some embodiments, the backbone structure of the AON does not comprise phosphorous but comprises peptide bonds, for example in a peptide nucleic acid (PNA), or linking groups including carbamate, amides, and linear and cyclic hydrocarbon groups. In some embodiments, the backbone modification is a phosphorothioate linkage. In some embodiments, the backbone modification is a phosphoramidate linkage.

In some In some embodiments, the antisense oligonucleotide (AON) comprises an unmodified sugar moiety such as ribose or deoxyribose or a modified sugar moiety or sugar analog, including a morpholino ring. Non-limiting examples of modified sugar moieties include 2' substitutions such as 2'-O-methyl (2'-O-Me), 2'-O-methoxyethyl (2'MOE), 2'-O-aminoethyl, 2'F; N3'→P5' phosphoramidate, 2'dimethylaminooxyethoxy, 2' dimethylaminoethoxyethoxy, 2'-guanidinidium, 2'-O-guanidinium ethyl, carbamate modified sugars, and bicyclic modified sugars. In some embodiments, the sugar moiety modification is an extra bridge bond, such as any of a locked nucleic acid (LNA). In some embodiments the sugar analog contains a morpholino ring, such as phosphorodiamidate morpholino (PMO). In some embodiments, the sugar moiety comprises a ribofuransyl or 2'deoxyribofuransyl modification. In some embodiments, the sugar moiety comprises 2'4'-constrained 2'O-methyloxyethyl (cMOE) modifications. In some embodiments, the sugar moiety comprises cEt 2', 4' constrained 2'-O ethyl BNA modifications. In some embodiments, the sugar moiety comprises tricycloDNA (tcDNA) modifications. In some embodiments, the sugar moiety comprises ethylene nucleic acid (ENA) modifications. In some embodiments, the sugar moiety comprises MCE modifications. In some embodiments, the antisense oligonucleotide (AON) comprises an artificial nucleotide analogue. Exemplary artificial nucleotide analogues include 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or combinations thereof. In some embodiments, the modified nucleotide analogue is a constrained ethyl (cEt) nucleotide.

In some embodiments, the antisense oligonucleotide (AON) comprises a number of nucleobases. In some embodiments, the number of nucleobases comprises a range of about 8 to 50, 8 to 40, 8 to 35, 8 to 30, 8 to 25, 8 to 20, 8 to 15, 9 to 50, 9 to 40, 9 to 35, 9 to 30, 9 to 25, 9 to 20, 9 to 15, 10 to 50, 10 to 40, 10 to 35, 10 to 30, 10 to 25, 10 to 20, 10 to 15, 11 to 50, 11 to 40, 11 to 35, 11 to 30, 11 to 25, 11 to 20, 11 to 15, 12 to 50, 12 to 40, 12 to 35, 12 to 30, 12 to 25, 12 to 20, 12 to 15, 13 to 50, 13 to 40, 13 to 35, 13 to 30, 13 to 25, 13 to 20, 14 to 50, 14 to 40, 14 to 35, 14 to 30, 14 to 25, 14 to 20, 15 to 50, 15 to 40, 15 to 35, 15 to 30, 15 to 25, 15 to 20, 20 to 50, 20 to 40, 20 to 35, 20 to 30, 20 to 25, 25 to 50, 25 to 40, 25 to 35, or 25 to 30 nucleobases.

In some embodiments, the sequence of the antisense oligonucleotide (AON) is at least or about 40%, 50%, 55%, 60%, 65%, 70%, 75%, 80%, 85%, 90%, 95%, 98%, 99%, or 99.5% complementary to a target sequence. In some embodiments, the target sequence is a sequence of the reverse transcriptase gene. In some embodiments, the target sequence is a RNA sequence. In some embodiments, the target sequence is a sequence as set forth in SEQ ID NO: 1, 2, 3, 4, 5, 6, 7, 8, 9, 10, 11, 12, 13, 14, 15, or 16. In some embodiments, the target sequence is a DNA sequence.

In some embodiments, the antisense oligonucleotide (AON) comprises a nucleotide sequence complementary to a target sequence. In some embodiments, the AON comprises a nucleotide sequence non-complementary to a target sequence. In some embodiments, AONs comprising a nucleotide sequence complementary to a target sequence is used in conjunction with AONs comprising a nucleotide sequence non-complementary to a target sequence.

In some embodiments, the reverse transcriptase inhibitor or salt thereof is capable of penetrating the blood-brain barrier, or is coupled with a molecular carrier that facilitates or allows the reverse transcriptase inhibitor penetrating the blood-brain barrier. For example, the reverse transcriptase inhibitor may be an antibody having a modified amino acid in one of the constant domain of the heavy chain that increases the penetration rate of the antibody. Alternatively and/or additionally, the reverse transcriptase inhibitor may be coupled with a molecular carrier or transporter (e.g., synthetic peptide K16ApoE, etc.) to increase its permeability through the blood brain barrier.

In some embodiments, the reverse transcriptase inhibitor or salt thereof inhibits generation of non-classical variant(s) of APP by at least or about 10%, 15%, 20%, 25%, 30%, 35%, 40%, 45%, 50%, 55%, 60%, 65%, 70%, 75%, 80%, 85%, 90%, 95%, 99%, or more than 99%. In some embodiments, the reverse transcriptase inhibitor or salt thereof inhibits generation of non-classical variant(s) of APP in a range of about 5% to about 100%, about 10% to about 90%, about 15% to about 85%, about 20% to about 80%, about 25% to about 75%, about 30% to about 70%, about 35% to about 65%, or about 40% to about 60%.

In some embodiments, efficacy of the reverse transcriptase inhibitor or salt thereof is determined. In some embodiments, the efficacy of the reverse transcriptase inhibitor or salt thereof is determined by measuring reverse transcriptase activity. In some embodiments, the reverse transcriptase activity is measured in a biological sample, including but not limited to, blood, platelets, and cerebrospinal fluid. In some embodiments, the reverse transcriptase inhibitor or salt thereof inhibits activity of the reverse transcriptase by at least or about 10%, 15%, 20%, 25%, 30%, 35%, 40%, 45%, 50%, 55%, 60%, 65%, 70%, 75%, 80%, 85%, 90%, 95%, 99%, or more than 99%. In some embodiments, the reverse transcriptase inhibitor or salt thereof inhibits activity of the reverse transcriptase in a range of about 5% to about 100%, about 10% to about 90%, about 15% to about 85%, about 20% to about 80%, about 25% to about 75%, about 30% to about 70%, about 35% to about 65%, or about 40% to about 60%.

Administration or Use of Reverse Transcriptase Inhibitors

The inventors further contemplate that generation of the one or more non-classical variant(s) of the APP gene in the subject (e.g., an individual having or suspected to have Alzheimer's disease (e.g., familial Alzheimer's disease, sporadic Alzheimer's disease, early onset Alzheimer's disease, etc.), preferably the individual does not have HIV or Hepatitis-B) can be inhibited by administering one or more reverse transcriptase inhibitors.

Any suitable methods of administering the reverse transcriptase inhibitors to an individual are contemplated. For example, the reverse transcriptase inhibitors can be administered to the individual orally, sublingually, bucally, by intravenous, intramuscular, subcutaneous, intra-arterial, parenteral injections, by administering by ocular route and/or by otic route, nasally, through inhalation (transmucosal), cutaneously, topically, rectally, intraperitoneally or transdermally. Thus, based on the type of administration, the form, dose and schedule of administration of reverse transcriptase inhibitors may vary. For example, the reverse transcriptase inhibitors can be formulated as a liquid, gel, semi-liquid, semi-solid, or solid form (e.g., a tablet, a capsule, a cachet, a liquid, or an aerosol spray, etc.)

With respect to the dose and schedule of administration, the dose and schedule can be determined based on the expected effect of the reverse transcriptase inhibitor in the subject or the individual. For example, the dose and schedule may be determined such that the reverse transcriptase inhibitor or salt thereof reduces amyloid beta accumulation by at least or about 5%, 10%, 15%, 20%, 25%, 30%, 35%, 40%, 45%, 50%, 55%, 60%, 65%, 70%, 75%, 80%, 85%, 90%, 95%, or greater than 95% in at least a portion of the brain of the subject or the individual. In another example, the dose and schedule may be determined such that the reverse transcriptase inhibitor or salt thereof reduces amyloid beta accumulation in a range of about 5% to about 100%, about 10% to about 90%, about 15% to about 85%, about 20% to about 80%, about 25% to about 75%, about 30% to about 70%, about 35% to about 65%, or about 40% to about 60% in at least a portion of the brain of the subject or the individual. In still another example, the dose and schedule may be determined such that the reverse transcriptase inhibitor or salt thereof reduces amyloid beta plaque formation by at least or about 5%, 10%, 15%, 20%, 25%, 30%, 35%, 40%, 45%, 50%, 55%, 60%, 65%, 70%, 75%, 80%, 85%, 90%, 95%, or greater than 95% in at least a portion of the brain of the subject or the individual. In still another example, the dose and schedule may be determined such that the reverse transcriptase inhibitor or salt thereof reduces amyloid beta plaque formation in a range of about 5% to about 100%, about 10% to about 90%, about 15% to about 85%, about 20% to about 80%, about 25% to about 75%, about 30% to about 70%, about 35% to about 65%, or about 40% to about 60% in at least a portion of the brain of the subject or the individual.

In some embodiments, the dose and schedule may be determined sufficient enough for the reverse transcriptase inhibitor or salt thereof to inhibit symptoms associated with Alzheimer's disease. For example, the dose and schedule may be determined such that the reverse transcriptase inhibitor or salt thereof inhibits cognitive decline including, but not limited to, mental decline, difficulty thinking and understanding, confusion, delusion, disorientation, forgetfulness, making things up, mental confusion, difficulty concentrating, inability to create new memories, inability to do simple math, or inability to recognize common things. In some embodiments, the reverse transcriptase inhibitor or salt thereof inhibits symptoms associated with Alzheimer's disease by at least or about 5%, 10%, 15%, 20%, 25%, 30%, 35%, 40%, 45%, 50%, 55%, 60%, 65%, 70%, 75%, 80%, 85%, 90%, 95%, or greater than 95%. In some embodiments, the dose and schedule may be determined such that the reverse transcriptase inhibitor or salt thereof inhibits symptoms associated with Alzheimer's disease in a range of about 5% to about 100%, about 10% to about 90%, about 15% to about 85%, about 20% to about 80%, about 25% to about 75%, about 30% to about 70%, about 35% to about 65%, or about 40% to about 60%.

In some embodiments, therapeutic efficacy of treating Alzheimer's disease following administration of a reverse transcriptase inhibitor or salt thereof is determined. In some embodiments, therapeutic efficacy is determined using one or more measurements. Exemplary measurements include, but are not limited to, Alzheimer's Disease Assessment Scale-Cognitive 14 Item Subscore (ADAS-Cog14), Alzheimer's Disease Cooperative Study-Instrumental Activities of Daily Living (ADCS-iADL), Alzheimer's Disease Assessment Scale-Cognitive 11 Item Subscore (ADAS-Cog11), Mini-Mental State Examination (MMSE), Alzheimer's Disease Cooperative Study Activities of Daily Living Inventory (ADCS-ADL), Functional Activities Questionnaire (FAQ), Clinical Dementia Rating-Sum of Boxes (CDR-SB), Neuropsychiatric Inventory (NPI), Resource Utilization in Dementia-Lite (RUD-Lite), Quality of Life in Alzheimer's Disease (QoL-AD), Alzheimer's Disease Rating Scale (iADRS), plasma Amyloid-Beta (Aβ), Volumetric Magnetic Resonance Imaging (vMRI), Florbetapir Positron Emission Tomography (PET) Scan, and Baseline in Cerebrospinal Fluid (CSF) Aβ Levels.

Additionally, administration of reverse transcriptase inhibitors may be accompanied with administering one or more known agent(s) for treating Alzheimer's disease, dementia, other neurodegenerative diseases, or other cognitive dysfunction. In some embodiments, the agent is a cholinesterase inhibitor, N-methyl-D-aspartate (NMDA) receptor antagonist, an anti-amyloid beta antibody, or a gamma secretase inhibitor or modulator. In some embodiments, the agent inhibits accumulation of amyloid beta in the subject's brain. In some embodiments, the cholinesterase inhibitor is selected from the group consisting of donepezil, galantamine, and rivastigmine. In some embodiments, the NMDA receptor antagonist is memantine. In some embodiments, the anti-amyloid beta antibody is selected from the group consisting of bapineuzumab, solanezumab, gantenerumab, crenezumab, BAN2401, ponezumab, and aducanumab. In some embodiments, the gamma secretase inhibitor or modulator is selected from the group consisting of LY450139, LY-411575, begacestat, BMS-708163, ELN-475516, MRK-003, and RO4929097. In some embodiments, the agent is donepezil, galantamine, memantine, rivastigmine, or donepezil and memantine.

In some embodiments, the cholinesterase inhibitor, N-methyl-D-aspartate (NMDA) receptor antagonist, the anti-amyloid beta antibody, or the gamma secretase inhibitor or modulator is administered prior to administration of the reverse transcriptase inhibitor. In some embodiments, the cholinesterase inhibitor, N-methyl-D-aspartate (NMDA) receptor antagonist, anti-amyloid beta antibody, or gamma secretase inhibitor or modulator is administered up to 1 day, up to 2 days, up to 3 days, up to 5 days, or more than 5 days prior to administration of the reverse transcriptase inhibitor. In some embodiments, the cholinesterase inhibitor, N-methyl-D-aspartate (NMDA) receptor antagonist, anti-amyloid beta antibody, or gamma secretase inhibitor or modulator is administered singly, or over a time course, such as daily, multiple times weekly, weekly, biweekly, monthly or less frequently prior to administration of the reverse transcriptase inhibitor.

In some embodiments, the cholinesterase inhibitor, N-methyl-D-aspartate (NMDA) receptor antagonist, anti-amyloid beta antibody, or gamma secretase inhibitor or modulator is administered following administration of the reverse transcriptase inhibitor. In some embodiments, the cholinesterase inhibitor, N-methyl-D-aspartate (NMDA) receptor antagonist, anti-amyloid beta antibody, or gamma secretase inhibitor or modulator is administered up to 1 day, up to 2 days, up to 3 days, up to 5 days, or more than 5 days following administration of the reverse transcriptase inhibitor. In some embodiments, the cholinesterase inhibitor, N-methyl-D-aspartate (NMDA) receptor antagonist, anti-amyloid beta antibody, or gamma secretase inhibitor or modulator is administered singly, or over a time course, such as daily, multiple times weekly, weekly, biweekly, monthly or less frequently following administration of the reverse transcriptase inhibitor.

Alternatively and/or additionally, the inventors also contemplate that a pharmaceutical composition can be formulated using one or more reverse transcriptase inhibitors and/or one or more known agent(s) for treating Alzheimer's disease such that the known agent for treating Alzheimer's disease and the reverse transcriptase inhibitors can be administered concurrently. In such embodiment, it is preferred that the compositions and dosages of each agent or reverse transcriptase inhibitor are formulated and determined to antagonism of two drugs (e.g., one reduces the effect of another during formulation, etc.) and/or physiological burden of the individual treated by the composition (e.g., drug-induced liver injury, etc.).

Diagnosis: Identification of an Individual Having Accumulated Amyloid Beta Proteins In some embodiments, disclosed herein are methods for detecting non-classical variant(s) of APP via an antibody. Exemplary antibodies include, but are not limited to, a monoclonal antibody, a polyclonal antibody, a bi-specific antibody, a multi-specific antibody, a grafted antibody, a human antibody, a humanized antibody, a synthetic antibody, a chimeric antibody, a camelized antibody, a single-chain Fvs (scFv) (including fragments in which the VL and VH are joined using recombinant methods by a synthetic or natural linker that enables them to be made as a single protein chain in which the VL and VH regions pair to form monovalent molecules, including single chain Fab and scFab), a single chain antibody, a Fab fragment (including monovalent fragments comprising the VL, VH, CL, and CH1 domains), a F(ab')2 fragment (including bivalent fragments comprising two Fab fragments linked by a disulfide bridge at the hinge region), a Fd fragment (including fragments comprising the VH and CH1 fragment), a Fv fragment (including fragments comprising the VL and VH domains of a single arm of an antibody), a single-domain antibody (a nanobody or dAb or sdAb) (including fragments comprising a VH domain), an isolated complementarity determining region (CDR), a diabody (including fragments comprising bivalent dimers such as two VL and VH domains bound to each other and recognizing two different antigens), a fragment comprised of only a single monomeric variable domain, disulfide-linked Fvs (sdFv), an intrabody, an anti-idiotypic (anti-Id) antibody, or ab antigen-binding fragments thereof. Additionally, the inventors contemplate that an individual characterized by or having accumulation of amyloid beta protein in the central nervous system can be identified by comparing an expression profile or an activity profile of one or more non-classical variant(s) of an APP gene to a reference expression profile of the one or more non-classical variant(s) derived from a cohort of control individuals. Preferably, the expression profile or an activity profile of one or more non-classical variant(s) of an APP gene is associated with the neurological disease or disorder.

In some embodiments, the expression profile is expression level of the one or more non-classical variant(s) of APP. In some embodiments, the expression profile is a set of expression levels of different non-classical variant of APP. In some embodiments, the activity profile is activity level of the one or more non-classical variant(s) of APP. In some embodiments, the activity profile is activity of a set of activity levels of different non-classical variant of APP. Alternatively and/or additionally, the expression profile or the activity profile of an individual at risk of developing a disease or disorder characterized by abnormal or excessive accumulation of amyloid beta protein is compared to a reference expression profile or activity profile from a cohort of control individuals (e.g., healthy, age-matched individuals, etc.).

In some embodiments, a presence or absence of one or more non-classical variant(s) of APP is compared to the reference expression profile or activity from the cohort of control individuals. In some embodiments, the expression profile is expression of a set of different non-classical variant(s) of APP. In some embodiments, the activity profile is activity of a set of different non-classical variant(s) of APP. In some embodiments, the non-classical variant of APP comprises a portion or all of an exon of the APP gene. In some embodiments, the non-classical variant of APP comprises a portion or all of exon 1, 2, 3, 4, 5, 6, 7, 8, 9, 10, 11, 12, 13, 14, 15, 16, 17, 18, or combinations thereof of the APP gene. In some embodiments, the one or more non-classical variant(s) of APP comprise a portion or all of exon 1, 2, 3, 4, 5, 6, 7, 9, 10, 11, 12, 13, 14, 15, 16, 17, 18, or combinations thereof. In some embodiments, the one or more non-classical variant(s) of APP does not comprise exon 8. In some embodiments, the non-classical variant of APP comprises a single nucleotide variation (SNV). In some embodiments, the non-classical variant of APP comprises one or more SNVs. In some embodiments, the SNV in APP, which translate to amino acid positions in APP include, but are not limited to, K670, M671, A673, D678, E682, K687, A692, E693, D694, A713, T714, V715, I716, V717, T719, M722, L723, and K724, wherein the amino acids correspond to positions 670, 671, 673, 678, 682, 687, 692, 693, 694, 713, 714, 715, 716, 717, 719, 722, 723, and 724 of SEQ ID NO: 17. In some embodiments, the SNV in APP, which translate to amino acid positions in APP include, but are not limited to, A673, A713, T714, V715, I716, V717, T719, and L723, wherein the amino acids correspond to positions 673, 713, 714, 715, 716, 717, 719, and 723 of SEQ ID NO: 17. In some embodiments, the SNV in APP, which translate to amino acid positions in APP include, but are not limited to, K670N, M671L, A673V, D678H, D678N, E682K, K687N, A692G, E693G, D694N, A713T, T714A, T714I, V715A, V715M, I716F, I716M, I716T, I716V, V717F, V717G, V717I, V717L, T719P, M722K, L723P, and K724N. In some embodiments, the SNV in APP, which translate to amino acid positions in APP include, but are not limited to, A673V, A713T, T714I, V715M, V715A, I716M, V717I, V717F, T719P, and L723P. In some embodiments, the SNV in APP, which translates to amino acid positions in APP includes, but are not limited to, A201, A235, D243, E246, E296, P299, R468H, A479, K496, A500, Y538, V562, E599, T600, P620, T663, E665, K670, M671, A673, H677, D678, E682, K687, A692, E693, D694, G709, A713, T714, V715, I716, V717, T719, M722, L723, K724, and H733 wherein the amino acids correspond to positions 201, 235, 243, 246, 296, 299, 468, 479, 496, 500, 538, 562, 599, 600, 620, 663, 665, 670, 671, 673, 677, 678, 682, 687, 692, 693, 694, 709, 713, 714, 715, 716, 717, 719, 722, 723, 724, and 733 of SEQ ID NO: 17. In some embodiments, the SNV in APP, which translates to amino acid positions in APP includes, but are not limited to, A201V, A235V, D243N, E246K, E296K, P299L, R468H, A479S, K496Q, A500T, Y538H, V562I, E599K, T600M, P620A, P620L, T663M, E665D, K670N, M671L, A673T, A673V, H677R, D678H, D678N, E682K, K687N, A692G, E693G, D694N, G709S, A713T, A713V, T714A, T714I, V715A, V715M, I716F, I716M, I716T, I716V, V717F, V717G, V717I, V717L, T719P, M722K, L723P, K724N, and H733P. In some embodiments, the one or more exon(s) in the one or more non-classical variant(s) of APP is rearranged as compared to control. In some embodiments, the non-classical variant of APP does not comprise exon 8 of the APP gene. In some embodiments, the non-classical variant of APP comprises a sequence as set forth in SEQ ID NO: 1, 2, 3, 4, 5, 6, 7, 8, 9, 10, 11, 12, 13, 14, 15, or 16.

In some embodiments, the expression profile is expression level. In some embodiments, the expression level of the one or more non-classical variants is at least or about 50%, 100%, 200%, 300%, 400%, 500%, 600%, 700%, or more than 700% increased or elevated as compared to the expression level from the cohort of control individuals. In some embodiments, the activity profile is activity level. In some embodiments, the activity level of the one or more non-classical variants is at least or about 50%, 100%, 200%, 300%, 400%, 500%, 600%, 700%, or more than 700% increased or elevated as compared to the activity level from the cohort of control individuals. In some embodiments, the expression profile or activity profile is used to detect the presence of one or more non-classical variant(s) of APP.

In some embodiments, the expression profile or the activity profile is used to diagnose an individual prior to administration of a reverse transcriptase inhibitor or salt thereof. In some embodiments, the individual is diagnosed with Alzheimer's disease by measuring the expression profile or the activity profile of the one or more non-classical variant(s) of APP. In some embodiments, the individual is diagnosed with Alzheimer's disease by measuring the expression profile or the activity profile of the one or more non-classical variant(s) of APP and comparing the expression profile or the activity profile to a reference expression profile or activity profile from a cohort of control individuals. In some embodiments, the individual is diagnosed with Alzheimer's disease when one or more exon(s) in the one or more non-classical variant(s) of APP is rearranged as compared to a control. In some embodiments, the expression profile is expression level. In some embodiments, the individual is diagnosed with Alzheimer's disease when the expression level exceeds a predetermined threshold (e.g., at least or about 50%, 100%, 200%, 300%, 400%, 500%, 600%, 700%, or more than 700% increased or elevated as compared to the expression level from the cohort of control individuals). In some embodiments, the activity profile is activity level. In some embodiments, the individual is diagnosed with Alzheimer's disease when the activity level exceeds a predetermined threshold (e.g., at least or about 50%, 100%, 200%, 300%, 400%, 500%, 600%, 700%, or more than 700% increased or elevated as compared to the activity level from the cohort of control individual).

Any suitable methods for determining the expression profile or the activity profile of the one or more non-classical variant(s) are contemplated. Exemplary methods include long-read sequencing of a biological sample from the individual or binding of one or more probe(s) to the biological sample from the individual.

Sequencing: In some embodiments, the expression profile of one or more non-classical variant(s) of amyloid precursor protein (APP) gene is measured by sequencing of a biological sample from the individual. Any suitable sequencing methods are contemplated, and exemplary sequencing methods include, but are not limited to, single molecule real-time sequencing, Polony sequencing, sequencing by ligation, reversible terminator sequencing, proton detection sequencing, ion semiconductor sequencing, nanopore sequencing, electronic sequencing, pyrosequencing, Maxam-Gilbert sequencing, chain termination (e.g., Sanger) sequencing, +S sequencing, sequencing by synthesis, or short read sequencing.

In some embodiments, the nucleotide sequencing comprises long-read sequencing (e.g., single molecule real-time sequencing, etc.). In some embodiments, the single molecule real-time sequencing is performed by attaching a different fluorescent dye to each of the nucleic acid bases and using a polymerase, and detecting the different fluorescent dyes upon polymerization process. In some embodiments, the long-read sequencing does not require a reference genome. In some embodiments, methods for measuring the expression profile comprise preparation of a biological sample prior to sequencing. In some embodiments, DNA is extracted and purified from the biological sample. In some embodiments, RNA is extracted. In some embodiments, RNA is extracted, purified, and reverse transcribed to cDNA. In some embodiments, after RNA or DNA is extracted, the reverse transcribed cDNA or DNA is amplified prior to sequencing. In some embodiments, single molecule real-time sequencing comprises additional preparation of the biological sample prior to sequencing. In some embodiments, the DNA is fragmented. In some embodiments, target regions are amplified to obtain fragmented DNA. In some embodiments, target regions are enriched by hybridization based DNA pull-down. Following fragmentation, in some embodiments, the ends of the DNA are repaired. In some embodiments, hairpin adapters are ligated to the DNA that then hybridizes to a primer. In some embodiments, a nuclease is used to remove DNA that did not ligate to the hairpin adapters. In some embodiments, a DNA polymerase is mixed and the DNA is sequenced.

In some embodiments, the expression level is measured following long-read sequencing. In some embodiments, the long-read sequencing is RNA sequencing or DNA sequencing. In some embodiments, the long-read sequencing is single molecule real-time sequencing. During a long-read sequencing reaction, sequenced base pairs or "reads" are generated. In some embodiments, the expression level is then quantified by counting a number of reads that map to the one or more non-classical variant(s) of APP sequences during the long-read sequencing reaction. In some embodiments, the one or more non-classical variant(s) of APP sequences comprise a sequence as set forth in SEQ ID NO: 1, 2, 3, 4, 5, 6, 7, 8, 9, 10, 11, 12, 13, 14, 15, or 16.

In some embodiments, the long read sequencing measures a change in the APP gene. In some embodiments, the change is a change in DNA of the APP gene. In some embodiments, the DNA is coding DNA. In some embodiments, the DNA is non-coding DNA. In some embodiments, the change is a change in RNA of the APP gene. In some embodiments, the RNA is coding RNA. In some embodiments, the RNA is non-coding RNA. In some embodiments, the change is a change in a protein encoded by the APP gene.

In some embodiments, the long read sequencing measures a single nucleotide variation (SNV) in the APP gene. In some embodiments, the long read sequencing measures one or more SNVs in the APP gene. In some embodiments, the SNV in APP, which translates to amino acid positions in APP includes, but are not limited to, K670, M671, A673, D678, E682, K687, A692, E693, D694, A713, T714, V715, I716, V717, T719, M722, L723, and K724, wherein the amino acids correspond to positions 670, 671, 673, 678, 682, 687, 692, 693, 694, 713, 714, 715, 716, 717, 719, 722, 723, and 724 of SEQ ID NO: 17. In some embodiments, the SNV in APP, which translates to amino acid positions in APP includes, but are not limited to, A673, A713, T714, V715, I716, V717, T719, and L723, wherein the amino acids correspond to positions 673, 713, 714, 715, 716, 717, 719, and 723 of SEQ ID NO: 17. In some embodiments, the SNV in APP, which translates to amino acid positions in APP includes, but are not limited to, K670N, M671L, A673V, D678H, D678N, E682K, K687N, A692G, E693G, D694N, A713T, T714A, T714I, V715A, V715M, I716F, I716M, I716T, I716V, V717F, V717G, V717I, V717L, T719P, M722K, L723P, and K724N. In some embodiments, the SNV in APP, which translates to amino acid positions in APP includes, but are not limited to, A673V, A713T, T714I, V715M, V715A, I716M, V717I, V717F, T719P, and L723P. In some embodiments, the SNV in APP, which translates to amino acid positions in APP includes, but are not limited to, A201, A235, D243, E246, E296, P299, R468H, A479, K496, A500, Y538, V562, E599, T600, P620, T663, E665, K670, M671, A673, H677, D678, E682, K687, A692, E693, D694, G709, A713, T714, V715, I716, V717, T719, M722, L723, K724, and H733 wherein the amino acids correspond to positions 201, 235, 243, 246, 296, 299, 468, 479, 496, 500, 538, 562, 599, 600, 620, 663, 665, 670, 671, 673, 677, 678, 682, 687, 692, 693, 694, 709, 713, 714, 715, 716, 717, 719, 722, 723, 724, and 733 of SEQ ID NO: 17. In some embodiments, the SNV in APP, which translates to amino acid positions in APP includes, but are not limited to, A201V, A235V, D243N, E246K, E296K, P299L, R468H, A479S, K496Q, A500T, Y538H, V562I, E599K, T600M, P620A, P620L, T663M, E665D, K670N, M671L, A673T, A673V, H677R, D678H, D678N, E682K, K687N, A692G, E693G, D694N, G709S, A713T, A713V, T714A, T714I, V715A, V715M, I716F, I716M, I716T, I716V, V717F, V717I, V717L, T719P, M722K, L723P, K724N, and H733P.

Pull-down Assays: In some embodiments, the expression profile of one or more non-classical variant(s) of the APP gene is measured by a pull-down assay. In some embodiments, one or more probe(s) for use in the pull-down assay is designed to hybridize to a portion or all of exon 1, 2, 3, 4, 5, 6, 7, 8, 9, 10, 11, 12, 13, 14, 15, 16, 17, 18, or combinations thereof. In some embodiments, one or more probe(s) for use in the pull-down assay is designed to hybridize to a portion or all of exon 1, 2, 3, 4, 5, 6, 7, 9, 10, 11, 12, 13, 14, 15, 16, 17, 18, or combinations thereof. In some embodiments, the one or more probe(s) for use in the pull-down assay is designed to hybridize to an APP intron sequence. In some embodiments, the one or more probe(s) for use in the pull-down assay is designed to hybridize to a portion or all of a non-classical variant comprising a sequence as set forth in SEQ ID NO: 1, 2, 3, 4, 5, 6, 7, 8, 9, 10, 11, 12, 13, 14, 15, or 16.

In some embodiments, the one or more probe(s) is labeled with an affinity tag. Exemplary affinity tags include, but are not limited to, biotin, desthiobiotin, histidine, polyhistidine, myc, hemagglutinin (HA), FLAG, glutathione S transferase (GST), or derivatives thereof. In some embodiments, the affinity tag is recognized by avidin, streptavidin, nickel, or glutathione.

In some embodiments, following a pull-down assay, one or more non-classical variant(s) of APP are amplified. In some embodiments, the one or more non-classical variant(s) of APP are amplified using primers designed to detect exon 1, 2, 3, 4, 5, 6, 7, 8, 9, 10, 11, 12, 13, 14, 15, 16, 17, or 18. In some embodiments, the one or more non-classical variant(s) of APP are amplified using primers designed to detect exon 1, 2, 3, 4, 5, 6, 7, 9, 10, 11, 12, 13, 14, 15, 16, 17, or 18. In some embodiments, the primers are used to detect one or more non-classical variant comprising a sequence as set forth in SEQ ID NO: 1, 2, 3, 4, 5, 6, 7, 8, 9, 10, 11, 12, 13, 14, 15, or 16. In some embodiments, the one or more non-classical variant is amplified by PCR. In some embodiments, the PCR is qPCR.

Following the pull-down assay, in some embodiments, the one or more non-classical variant(s) of APP are not amplified. In some embodiments, the one or more non-classical variant(s) of APP are visualized using a fluorescent assay, a radioactivity assay, or a luminescent assay. For example, the one or more probes used to hybridize to the one or more non-classical variant(s) of APP further comprises a fluorescent tag that is detected using the fluorescent assay. In some embodiments, the one or more non-classical variant(s) of APP are visualized by gel electrophoresis.

In some embodiments, the pull down assay measures a change in the APP gene. In some embodiments, the change is a change in DNA of the APP gene. In some embodiments, the DNA is coding DNA. In some embodiments, the DNA is non-coding DNA. In some embodiments, the change is a change in RNA of the APP gene. In some embodiments, the RNA is coding RNA. In some embodiments, the RNA is non-coding RNA. In some embodiments, the change is a change in a protein encoded by the APP gene.

Hybridization Assays: In some embodiments, the expression profile of one or more non-classical variant(s) of the amyloid precursor protein (APP) gene is measured by binding of one or probe(s) to one or more non-classical variant(s) of APP. In some embodiments, the one or more probe(s) is a polypeptide. In some embodiments, the one or more probe(s) is a polynucleotide.

In some embodiments, intraexonic rearrangements are detected by measuring binding of the one or more probe(s). In some embodiments, the one or more probe(s) hybridizes to target sequences within at least two exons of APP gene. For example, the one or more probe(s) hybridizes to sequences with one end complementary to a 3' end of one exon of APP and a second end complementary to a 5' end of a downstream exon of APP. In some embodiments, the one or more probe(s) hybridizes to target sequences within at least two exons that are consecutive exons of APP. In some embodiments, the one or more probe(s) hybridizes to target sequences within at least two exons that are non-consecutive exons of APP. In some embodiments, the one or more probe(s) hybridizes to target sequences within an APP intron sequence.

In some embodiments, the one or more probe(s) are provided in an array. In some embodiments, the array comprises one or more probe(s) for measuring an expression profile for one or more non-classical variant(s) of APP. In some embodiments, the one or more probe(s) detects RNA or DNA. In some embodiments, the one or more probe(s) detect exonic rearrangements such as intraexonic rearrangements of APP. In some embodiments, the one or more probes hybridize to a portion or all of an exon 1, 2, 3, 4, 5, 6, 7, 8, 9, 10, 11, 12, 13, 14, 15, 16, 17, 18, or combinations thereof of APP. In some embodiments, the one or more probes hybridize to a portion or all of an exon 1, 2, 3, 4, 5, 6, 7, 9, 10, 11, 12, 13, 14, 15, 16, 17, 18, or combinations thereof of APP. For example, the array comprises RNA probes designed to hybridize to the one or more non-classical variant(s) of APP.

In some embodiments, the one or more probe(s) are provided on a microarray chip. In some embodiments, the chip comprises one or more probe(s) for measuring an expression profile for one or more non-classical variant(s) of APP. In some embodiments, the one or more probe(s) detects RNA. In some embodiments, the one or more probe(s) detects DNA. In some embodiments, the one or more probe(s) detect exonic rearrangements such as intraexonic rearrangements of APP. In some embodiments, the one or more probes hybridize to a portion or all of an exon 1, 2, 3, 4, 5, 6, 7, 8, 9, 10, 11, 12, 13, 14, 15, 16, 17, 18, or combinations thereof of APP. In some embodiments, the one or more probes hybridize to a portion or all of an exon 1, 2, 3, 4, 5, 6, 7, 9, 10, 11, 12, 13, 14, 15, 16, 17, 18, or combinations thereof of APP.

In some embodiments, the one or more probe(s) bind to RNA or DNA from the one or more non-classical variant(s) of APP gene. In some embodiments, the one or more probe(s) are used for an amplification reaction. In some embodiments, the amplification reaction is PCR. In some embodiments, the amplification reaction is quantitative such as qPCR. In some embodiments, the PCR reaction utilizes a TaqMan™ or a similar quantitative PCR technology. In some embodiments, at least one primer used in the PCR reaction comprises a sequence as set forth in SEQ ID NO: 19 or 20.

The one or more probe(s), in some embodiments, bind to a protein encoded by the one or more non-classical variant(s) of APP gene. Exemplary methods for detecting binding of the one or more probe(s) include, but are not limited to, enzyme linked immunosorbent assays (ELISA), Western blots, spectroscopy, mass spectrometry, peptide arrays, colorimetry, electrophoresis, isoelectric focusing, immunoprecipitations, immunoassays, and immunofluorescence. In some embodiments, methods for detecting binding of the one or more probe(s) comprise use of microscopy methods. In some embodiments, microscopy methods comprise stimulated emission depletion (STED), ground state depletion (GSD), RESOLFT (reversible saturable optical linear fluorescence transitions), or structured illumination microscopy (SIM). In some embodiments, microscopy methods comprise stochastic super-resolution including, but not limited to, super-resolution optical fluctuation imaging (SOFI) and all single-molecular localization method (SMLM) such as spectral precision determination microscopy (SPDM), SPDMphymod, photo-activated localization microscopy (PALM), FPALM, stochastic optical reconstruction microscopy (STORM), and dSTORM In some embodiments, the expression profile of the one or more non-classical variant(s) of the APP gene is measured by in situ hybridization or immunological hybridization. In some embodiments, the in situ hybridization is performed without amplification. In some embodiments, the in situ hybridization is performed without polymerase dependent amplification. In some embodiments, the in situ hybridization comprises capturing the one or more non-classical variant(s) of APP from the biological sample on a solid support prior to contacting the one or more non-classical variant(s) of APP with the one or more probe(s). In some embodiments, the in situ hybridization is chromogenic in situ hybridization. In some embodiments, the in situ hybridization is fluorescence in situ hybridization. In some embodiments, in situ hybridization allows for detection of intraexonic rearrangements. In some embodiments, in situ hybridization allows for detection for genomic rearrangements such as between introns and exons or between exons and exons. In some embodiments, the one or more probe(s) for in situ hybridization hybridizes to a region spanning an intraexonic rearrangement. For example, for the non-classical variant cAPP-R3/16, the one or more probe(s) hybridize to a region spanning exon 3 and exon 16. In some embodiments, the one or more probe(s) hybridize to a region of a sequence as set forth in SEQ ID NO: 1, 2, 3, 4, 5, 6, 7, 8, 9, 10, 11, 12, 13, 14, 15, or 16.

Described herein, in certain embodiments, one or more probe(s) that hybridize to an intraexonic junction are non-classical variants of APP comprising portions of at least two exons, wherein the at least two exons are linked by intraexonic junctions. In some embodiments, the one or more probe(s) hybridize to an intraexonic junction between exon 1 and exon 2, 3, 4, 5, 6, 7, 8, 9, 10, 11, 12, 13, 14, 15, 16, 17, 18, or combinations thereof. In some embodiments, the one or more probe(s) hybridize to an intraexonic junction between exon 2 and exon 1, 3, 4, 5, 6, 7, 8, 9, 10, 11, 12, 13, 14, 15, 16, 17, 18, or combinations thereof. In some embodiments, the one or more probe(s) hybridize to an intraexonic junction between exon 3 and exon 1, 2, 4, 5, 6, 7, 8, 9, 10, 11, 12, 13, 14, 15, 16, 17, 18, or combinations thereof. In some embodiments, the one or more probe(s) hybridize to an intraexonic junction between exon 4 and exon 1, 2, 3, 5, 6, 7, 8, 9, 10, 11, 12, 13, 14, 15, 16, 17, 18, or combinations thereof. In some embodiments, the one or more probe(s) hybridize to an intraexonic junction between exon 5 and exon 1, 2, 3, 4, 6, 7, 8, 9, 10, 11, 12, 13, 14, 15, 16, 17, 18, or combinations thereof. In some embodiments, the one or more probe(s) hybridize to an intraexonic junction between exon 6 and exon 1, 2, 3, 4, 5, 7, 8, 9, 10, 11, 12, 13, 14, 15, 16, 17, 18, or combinations thereof. In some embodiments, the one or more probe(s) hybridize to an intraexonic junction between exon 7 and exon 1, 2, 3, 4, 5, 6, 8, 9, 10, 11, 12, 13, 14, 15, 16, 17, 18, or combinations thereof. In some embodiments, the one or more probe(s) hybridize to an intraexonic junction between exon 8 and exon 1, 2, 3, 4, 5, 6, 7, 9, 10, 11, 12, 13, 14, 15, 16, 17, 18, or combinations thereof. In some embodiments, the one or more probe(s) hybridize to an intraexonic junction between exon 9 and exon 1, 2, 3, 4, 5, 6, 7, 8, 10, 11, 12, 13, 14, 15, 16, 17, 18, or combinations thereof. In some embodiments, the one or more probe(s) hybridize to an intraexonic junction between exon 10 and exon 1, 2, 3, 4, 5, 6, 7, 8, 9, 11, 12, 13, 14, 15, 16, 17, 18, or combinations thereof. In some embodiments, the one or more probe(s) hybridize to an intraexonic junction between exon 11 and exon 1, 2, 3, 4, 5, 6, 7, 8, 9, 10, 12, 13, 14, 15, 16, 17, 18, or combinations thereof. In some embodiments, the one or more probe(s) hybridize to an intraexonic junction between exon 12 and exon 1, 2, 3, 4, 5, 6, 7, 8, 9, 10, 11, 13, 14, 15, 16, 17, 18, or combinations thereof. In some embodiments, the one or more probe(s) hybridize to an intraexonic junction between exon 13 and exon 1, 2, 3, 4, 5, 6, 7, 8, 9, 10, 11, 12, 14, 15, 16, 17, 18, or combinations thereof. In some embodiments, the one or more probe(s) hybridize to an intraexonic junction between exon 14 and exon 1, 2, 3, 4, 5, 6, 7, 8, 9, 10, 11, 12, 13, 15, 16, 17, 18, or combinations thereof. In some embodiments, the one or more probe(s) hybridize to an intraexonic junction between exon 15 and exon 1, 2, 3, 4, 5, 6, 7, 8, 9, 10, 11, 12, 13, 14, 16, 17, 18, or combinations thereof. In some embodiments, the one or more probe(s) hybridize to an intraexonic junction between exon 16 and exon 1, 2, 3, 4, 5, 6, 7, 8, 9, 10, 11, 12, 13, 14, 15, 17, 18, or combinations thereof. In some embodiments, the one or more probe(s) hybridize to an intraexonic junction between exon 17 and exon 1, 2, 3, 4, 5, 6, 7, 8, 9, 10, 11, 12, 13, 14, 15, 16, 18, or combinations thereof. In some embodiments, the one or more probe(s) hybridize to an intraexonic junction between exon 18 and exon 1, 2, 3, 4, 5, 6, 7, 8, 9, 10, 11, 12, 13, 14, 15, 16, 17, or combinations thereof. In some embodiments, the one or more probe(s) hybridize to an intraexonic junction between exon 1 and exon 11, exon 1 and exon 14, exon 2 and exon 17, exon 2 and exon 14, exon 2 and exon 18, exon 2 and exon 16, exon 3 and exon 16, exon 3 and exon 14, exon 3 and exon 17, exon 6 and exon 17, exon 6 and exon 18, exon 3 and exon 9, exon 2 and exon 9, exon 16 and exon 18, exon 6 and exon 12, exon 5 and exon 16, or exon 16 and exon 17.

In situ hybridization, in some embodiments, comprises probes for detecting one or more non-classical variant(s) of APP. In some embodiments, the probes hybridize to RNA comprising the one or more non-classical variant(s) of APP. In some embodiments, the probes hybridize to DNA comprising the one or more non-classical variant(s) of APP. In some embodiments, the probes hybridize to RNA comprising a portion of a sequence as set forth in SEQ ID NO: 1, 2, 3, 4, 5, 6, 7, 8, 9, 10, 11, 12, 13, 14, 15, or 16. In some embodiments, the probes comprise a base-pairing region complementary to the target nucleic acid, a spacer sequence, and a base-tail sequence. In some embodiments, two tail sequences form a hybridization site for amplification. In some embodiments, the target nucleic acid is visualized following amplification. In some embodiments, the probes hybridize to protein encoded by the non-classical variant of APP. In some embodiments, the probes are removed prior to visualization. In some embodiments, the probes are removed enzymatically, chemically, or mechanically. For example, the probes are removed using restriction enzymes.

In some embodiments, a number of probes are used for in situ hybridization. In some embodiments, in situ hybridization comprises at least or about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 or more 100 probes. In some embodiments, in situ hybridization comprises at most 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 probes. In some embodiments, a number of probe pairs are used for in situ hybridization. In some embodiments, the number of probe pairs comprises at least or about 1, 2, 3, 4, 5, 6, 7, 8, 9, 10, 11, 12, 13, 14, 15, 16, 17, 18, 19, 20, 25, 30, 35, 40, 45, 50, or more than 50 probe pairs. In some embodiments, in situ hybridization comprises at most 1, 2, 3, 4, 5, 6, 7, 8, 9, 10, 11, 12, 13, 14, 15, 16, 17, 18, 19, 20, 25, 30, 35, 40, 45, or 50 probe pairs. In some embodiments, following hybridization of a probe or a probe pair, the probe or probe pair are amplified prior to visualization.

In some embodiments, a probe is labeled. In some embodiments, a probe is labeled with a radioactive label, a fluorescent label, an enzyme, a chemiluminescent tag, a colorimetric tag, an affinity tag or other labels or tags that are known in the art.

Exemplary affinity tags include, but are not limited to, biotin, desthiobiotin, histidine, polyhistidine, myc, hemagglutinin (HA), FLAG, glutathione S transferase (GST), or derivatives thereof. In some embodiments, the affinity tag is recognized by avidin, streptavidin, nickel, or glutathione.

In some embodiments, the fluorescent label is a fluorophore, a fluorescent protein, a fluorescent peptide, quantum dots, a fluorescent dye, a fluorescent material, or variations or combinations thereof.

Exemplary fluorophores include, but are not limited to, Alexa-Fluor dyes (e.g., Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 647, Alexa Fluor® 660, Alexa Fluor® 680, Alexa Fluor® 700, and Alexa Fluor® 750), APC, Cascade Blue, Cascade Yellow and R-phycoerythrin (PE), DyLight 405, DyLight 488, DyLight 550, DyLight 650, DyLight 680, DyLight 755, DyLight 800, FITC, Pacific Blue, PerCP, Rhodamine, and Texas Red, Cy5, Cy5.5, Cy7.

Examples of fluorescent peptides include GFP (Green Fluorescent Protein) or derivatives of GFP (e.g., EBFP, EBFP2, Azurite, mKalamal, ECFP, Cerulean, CyPet, YFP, Citrine, Venus, YPet).

Examples of fluorescent dyes include, but are not limited to, xanthenes (e.g., rhodamines, rhodols and fluoresceins, and their derivatives); bimanes; coumarins and their derivatives (e.g., umbelliferone and aminomethyl coumarins); aromatic amines (e.g., dansyl; squarate dyes); benzofurans; fluorescent cyanines; indocarbocyanines; carbazoles; dicyanomethylene pyranes; polymethine; oxabenzanthrane; xanthene; pyrylium; carbostyl; perylene; acridone; quinacridone; rubrene; anthracene; coronene; phenanthrecene; pyrene; butadiene; stilbene; porphyrin; pthalocyanine; lanthanide metal chelate complexes; rare-earth metal chelate complexes; and derivatives of such dyes. In some embodiments, the fluorescein dye is, but not limited to, 5-carboxyfluorescein, fluorescein-5-isothiocyanate, fluorescein-6-isothiocyanate and 6-carboxyfluorescein. In some embodiments, the rhodamine dye is, but not limited to, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, and rhodamine 101 sulfonyl chloride (sold under the tradename of TEXAS RED®). In some embodiments, the cyanine dye is Cy3, Cy3B, Cy3.5, Cy5, Cy5.5, Cy7, IRDYE680, Alexa Fluor 750, IRDye800CW, or ICG.

Fluorescent labels are detected by any suitable method. For example, a fluorescent label is detected by exciting the fluorochrome with the appropriate wavelength of light and detecting the resulting fluorescence, e.g., by microscopy, visual inspection, via photographic film, by the use of electronic detectors such as charge coupled devices (CCDs), or photomultipliers. In some embodiments, the one or more probe(s) are labeled with the same fluorescent label. In some embodiments, the one or more probe(s) are labeled with different fluorescent labels.

In some embodiments, the expression level is measured using PCR. Examples of PCR techniques include, but are not limited to quantitative PCR (qPCR), single cell PCR, PCR-RFLP, digital PCR (dPCR), droplet digital PCR (ddPCR), single marker qPCR, hot start PCR, and Nested PCR.

In some embodiments, the expression level is measured using qPCR. In some embodiments, the qPCR comprises use of fluorescent dyes or fluorescent probes. In some embodiments, the fluorescent dye is an intercalating dye. Examples of intercalating dyes include, but are not limited to, intercalating dyes include SYBR green I, SYBR green II, SYBR gold, ethidium bromide, methylene blue, Pyronin Y, DAPI, acridine orange, Blue View, or phycoerythrin. In some embodiments, the qPCR comprises use of more than one fluorescent probe. In some embodiments, the use of more than one fluorescent probes allows for multiplexing. For example, different non-classical variants are hybridized to different fluorescent probes and can be detected in a single qPCR reaction.

In some embodiments, the probe is used for visualization of the one or more non-classical variant(s) of APP in an individual. In some embodiments, the probe is visualized by X-Ray, fluoroscopes, ultrasound, CT-scan, PET scan, magnetic resonance image (MRIs), or electromagnetic field.

In some embodiments, the hybridization assay measures a change in the APP gene. In some embodiments, the change is a change in DNA of the APP gene. In some embodiments, the DNA is coding DNA. In some embodiments, the DNA is non-coding DNA. In some embodiments, the change is a change in RNA of the APP gene. In some embodiments, the RNA is coding RNA. In some embodiments, the RNA is non-coding RNA. In some embodiments, the change is a change in a protein encoded by the APP gene.

Samples: Any suitable samples, preferably any biological samples, to obtain DNA and/or RNA sequencing and/or expression information are contemplated. In some embodiments, the expression profile or the activity profile is determined from a biological sample from the individual. In some embodiments, the biological sample comprises RNA or DNA. In some embodiments, the RNA is pre-mRNA. In some embodiments, the RNA is mRNA. In some embodiments, the DNA is nuclear DNA. In some embodiments, the DNA is extrachromosomal or extranuclear DNA. In some embodiments, the DNA is circular DNA.

In some embodiments, the biological sample is from a blood sample. In some embodiments, one or more biomarkers in the blood are measured. In some embodiments, the blood sample is processed by centrifugation such as by density centrifugation. In some embodiments, the blood sample is treated with a red blood cell lysis agent. In some embodiments, the blood sample comprises cells from the Central Nervous System (e.g., neurons, astrocytes, or microglia) that are released during break down of the blood brain barrier. In some embodiments, the biological sample is from cerebrospinal fluid. In some embodiments, the cerebrospinal fluid comprises cells from the central nervous system (e.g., neurons, astrocytes, or microglia) that are released during break down of the blood brain barrier.

A biological sample, in some embodiments, comprises exosomes. Exosomes are cell-derived vesicles that are released from many cell types including, but not limited to, dendritic cells (DCs), lymphocytes, platelets, mast cells, epithelial cells, endothelial cells, and neurons. In some embodiments, the exosomes are found in blood and/or cerebrospinal fluid.

In some embodiments, nucleic acid is extracted from the biological sample. In some embodiments, the nucleic acid is DNA. In some embodiments, the DNA is genomic DNA. In some embodiments, the DNA is extrachromosomal DNA. In some embodiments, the DNA is circular DNA. In some embodiments, the nucleic acid is RNA. The nucleic acid, in some embodiments, is extracted using any technique that does not interfere with subsequent analysis. For example, the nucleic acid is extracted using alcohol precipitation, using ethanol, methanol, or isopropyl alcohol, phenol, chloroform, cesium chloride, or in combination thereof. In some embodiments, the nucleic acid is extracted using sodium, potassium or ammonium acetate or any other salt commonly used to precipitate DNA. In some embodiments, the nucleic acid is extracted using a column or resin based nucleic acid purification. In some embodiments, after extraction the nucleic acid is stored in water, Tris buffer, or Tris-EDTA buffer before subsequent analysis. For example, storage is less than 8° C., 4° C., −20° C., or −70° C. In some embodiments, the nucleic acid is stored for 1, 2, 3, 4, 5, 6, or 7 days. In some embodiments, the nucleic acid is stored for 1, 2, 3, or 4 weeks. In some embodiments, the nucleic acid is stored for 1, 2, 3, 4, 5, 6, 7, 8, 9, 10, 11, or 12 months.

In some embodiments, the expression profile or the activity profile is used to more accurately diagnose or treat an individual having a disease or disorder. In some embodiments, use of the expression profile or the activity profile is at least or about 15%, 20%, 25%, 30%, 35%, 40%, 45%, 50%, 55%, 60%, 65%, 70%, 75%, 80%, 85%, 90%, 95% or more than 95% more accurate at diagnosing a disease or disorder. In some embodiments, use of the expression profile or the activity profile is at least or about 1.5 times (1.5×), 2×, 2.5×, 3×, 3.5×, 4.0×, 4.5×, 5×, 6×, 7×, 8×, 9×, 10×, or more than 10× more accurate at diagnosing a disease or disorder. In some embodiments, the disease or disorder is Alzheimer's disease. In some embodiments, methods as described herein for accurately diagnosing or treating Alzheimer's disease are improved as compared to methods comprising neurological tests, mental exams, or brain imaging (e.g., MRI, CT, or PET scans).

In some embodiments, determining whether the individual has or is predisposed to Alzheimer's disease is based on the expression profile or the activity profile from, wherein a likelihood of having or being predisposed to Alzheimer's disease is increased when the expression profile or the activity profile is elevated compared to a reference expression profile or reference activity profile of the one or more non-classical variant(s) derived from a cohort of control individuals. Methods as described herein for determining a likelihood of having or being predisposed to Alzheimer's disease, in some embodiments, are improved as compared to methods comprising neurological tests, mental exams, or brain imaging (e.g., MRI, CT, or PET scans). In some embodiments, the likelihood of having or being predisposed to Alzheimer's disease is increased by at least or about 15%, 20%, 25%, 30%, 35%, 40%, 45%, 50%, 55%, 60%, 65%, 70%, 75%, 80%, 85%, 90%, 95% or more than 95% by determining the expression profile or activity profile of the one or more non-classical variant(s). In some embodiments, the likelihood of having or being predisposed to Alzheimer's disease is increased by at least or about 1.5×, 2×, 2.5×, 3×, 3.5×, 4.0×, 4.5×, 5×, 6×, 7×, 8×, 9×, 10×, or more than 10× by determining the expression profile or activity profile of the one or more non-classical variant(s).

Consequently such determined or identified expression profile or the activity profile can be used for treating an individual having a disease or disorder. In some embodiments, a therapeutic agent is administered, and/or optimized, based on the expression profile or the activity profile. In some embodiments, the expression profile or the activity profile is measured prior to a treatment, during a treatment, or after a treatment. For example the expression profile or the activity profile is measured at 1 day, 2 days, 3 days, 4 days, 5 days 6 days, 1 week, 2 weeks, 3, weeks, 4 weeks, 1 month, 2 months, 3 months, 4 months, 5 months, 6 months, 7 months, 8 months, 9 months, 10 months, 11 months, 1 year, 2 years, or more than 2 years before treatment. In some embodiments, the expression profile or the activity profile is measured at 1 day, 2 days, 3 days, 4 days, 5 days 6 days, 1 week, 2 weeks, 3, weeks, 4 weeks, 1 month, 2 months, 3 months, 4 months, 5 months, 6 months, 7 months, 8 months, 9 months, 10 months, 11 months, 1 year, 2 years, or more than 2 years occurs after treatment.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1. Identification of Non-Classical Variants

Non-classical variants were identified from neurons isolated from non-diseased brains and Alzheimer's disease brains.

Fluorescence Activated Cell Sorting of Neurons

Neuronal nuclei were isolated from postmortem frontal cortices (CTX) and cerebellums (CBL) of non-diseased (Non-AD) and Alzheimer's disease (AD) brains and prepared for fluorescence activated cell sorting (FACS). Isolated nuclei were fixed and labeled with rabbit anti-NeuN antibody (1:800) (Millipore, Germany) and Alexa Fluor 488 donkey anti-rabbit IgG secondary (1:500) (Life Technologies, Carlsbad, Calif.), and counterstained with propidium iodide (PI) (50 µg/ml) (Sigma, St. Louis, Mo.). Electronically gated diploid neuronal nuclei, determined by PI fluorescence and immunolabeling, were analyzed and sorted.

RNA Extraction

Figure 2:
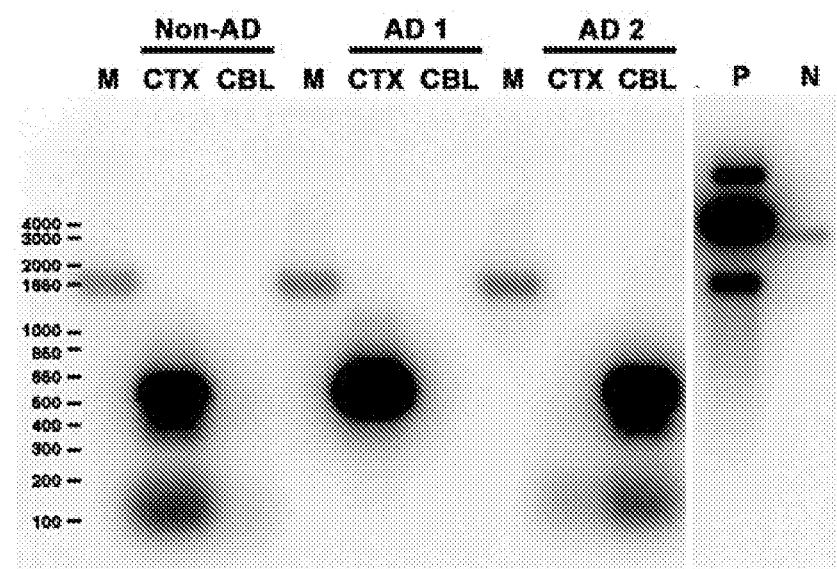
FIG. 2 illustrates a Southern blot of RT-PCR from neurons isolated from cortices (CTX) and cerebellums (CBL) from non-diseased (Non-AD) postmortem brains and Alzheimer's disease (AD) brains hybridized with APP cDNA probe. P and N represent positive (APP plasmid) and negative (Presenilin 1 plasmid) control, respectively.

Following FACS, RNA was extracted from populations of 50 NeuN positive nuclei. Extracted RNA were reverse-transcribed with (CTAGTTCTGCATCTGCT-CAAAGAACTTG) (SEQ ID NO: 18) and amyloid precursor protein (APP) cDNA was amplified by polymerase-chain reactions (PCR) using a forward primer (ATGCTGCCCGGTTTGGCA) (SEQ ID NO: 19) and a reverse primer (CTAGTTCTGCATCTGCT-CAAAGAACTTG) (SEQ ID NO: 20). Half of the PCR products were run and separated on agarose gels with a DNA ladder (M) (FIG. 1). Gels were transferred to nylon membranes and then blotted with $P^{32}$-labelled APP cDNA probe (SEQ ID NO. 21) as seen in Table 3. Radioactivity on the membranes was detected by Typhoon phosphorimager (FIG. 2).

TABLE 3

| SEQ ID NO | Name | Sequence |
|---|---|---|
| 21 | APP cDNA Probe | ACTGCTCCTGCTGGCCGCCTGGACGGCTCGGGCGCTGGAGGTAC CCACTGATGGTAATGCTGGCCTGCTGGCTGAACCCCAGATTGCC ATGTTCTGTGGCAGACTGAACATGCACATGAATGTCCAGAATGG GAAGTGGGATTCAGATCCATCAGGGACCAAAACCTGCATTGATA |

TABLE 3-continued

| SEQ ID NO | Name | Sequence |
|---|---|---|
| | | CCAAGGAAGGCATCCTGCAGTATTGCCAAGAAGTCTACCCTGAA |
| | | CTGCAGATCACCAATGTGGTAGAAGCCAACCAACCAGTGACCAT |
| | | CCAGAACTGGTGCAAGCGGGGCCGCAAGCAGTGCAAGACCCATC |
| | | CCCACTTTGTGATTCCCTACCGCTGCTTAGTTGGTGAGTTTGTAA |
| | | GTGATGCCCTTCTCGTTCCTGACAAGTGCAAATTCTTACACCAGG |
| | | AGAGGATGGATGTTTGCGAAACTCATCTTCACTGGCACACCGTC |
| | | GCCAAAGAGACATGCAGTGAGAAGAGTACCAACTTGCATGACTA |
| | | CGGCATGTTGCTGCCCTGCGGAATTGACAAGTTCCGAGGGGTAG |
| | | AGTTTGTGTGTTGCCCACTGGCTGAAGAAAGTGACAATGTGGAT |
| | | TCTGCTGATGCGGAGGAGGATGACTCGGATGTCTGGTGGGGCGG |
| | | AGCAGACACAGACTATGCAGATGGGAGTGAAGACAAAGTAGTA |
| | | GAAGTAGCAGAGGAGGAAGAAGTGGCTGAGGTGGAAGAAGAAG |
| | | AAGCCGATGATGACGAGGACGATGAGGATGGTGATGAGGTAGA |
| | | GGAAGAGGCTGAGGAACCCTACGAAGAAGCCACAGAGAGAACC |
| | | ACCAGCATTGCCACCACCACCACCACCACCACAGAGTCTGTGGA |
| | | AGAGGTGGTTCGAGAGGTGTGCTCTGAACAAGCCGAGACGGGGC |
| | | CGTGCCGAGCAATGATCTCCCGCTGGTACTTTGATGTGACTGAAG |
| | | GGAAGTGTGCCCCATTCTTTTACGGCGGATGTGGCGGCAACCGG |
| | | AACAACTTTGACACAGAAGAGTACTGCATGGCCGTGTGTGGCAG |
| | | CGCCATTCCTACAACAGCAGCCAGTACCCCTGATGCCGTTGACA |
| | | AGTATCTCGAGACACCTGGGGATGAGAATGAACATGCCCATTTC |
| | | CAGAAAGCCAAAGAGAGGCTTGAGGCCAAGCACCGAGAGAGAA |
| | | TGTCCCAGGTCATGAGAGAATGGGAAGAGGCAGAACGTCAAGC |
| | | AAAGAACTTGCCTAAAGCTGATAAGAAGGCAGTTATCCAGCATT |
| | | TCCAGGAGAAAGTGGAATCTTTGGAACAGGAAGCAGCCAACGA |
| | | GAGACAGCAGCTGGTGGAGACACACATGGCCAGAGTGGAAGCC |
| | | ATGCTCAATGACCGCCGCCGCCTGGCCCTGGAGAACTACATCAC |
| | | CGCTCTGCAGGCTGTTCCTCCTCGGCCTCGTCACGTGTTCAATAT |
| | | GCTAAAGAAGTATGTCCGCGCAGAACAGAAGGACAGACAGCAC |
| | | ACCCTAAAGCATTTCGAGCATGTGCGCATGGTGGATCCCAAGAA |
| | | AGCCGCTCAGATCCGGTCCCAGGTTATGACACACCTCCGTGTGAT |
| | | TTATGAGCGCATGAATCAGTCTCTCTCCCTGCTCTACAACGTGCC |
| | | TGCAGTGGCCGAGGAGATTCAGGATGAAGTTGATGAGCTGCTTC |
| | | AGAAAGAGCAAAACTATTCAGATGACGTCTTGGCCAACATGATT |
| | | AGTGAACCAAGGATCAGTTACGGAAACGATGCTCTCATGCCATC |
| | | TTTGACCGAAACGAAAACCACCGTGGAGCTCCTTCCCGTGAATG |
| | | GAGAGTTCAGCCTGGACGATCTCCAGCCGTGGCATTCTTTTGGGG |
| | | CTGACTCTGTGCCAGCCAACACAGAAAACGAAGTTGAGCCTGTT |
| | | GATGCCCGCCCTGCTGCCGACCGAGGACTGACCACTCGACCAGG |
| | | TTCTGGGTTGACAAATATCAAGACGGAGGAGATCTCTGAAGTGA |
| | | AGATGGATGCAGAATTCCGACATGACTCAGGATATGAAGTTCAT |
| | | CATCAAAAATTGGTGTTCTTTGCAGAAGATGTGGGTTCAAACAA |
| | | AGGTGCAATCATTGGACTCATGGTGGGCGGTGTTGTCATAGCGA |
| | | CAGTGATCGTCATCACCTTGGTGATGCTGAAGAAGAAACAGTAC |
| | | ACATCCATTCATCATGGTGTGGTGGAGGTTGACGCCGCTGTCACC |
| | | CCAGAGGAGCGCCACCTGTCCAAGATGCAGCAGAACGGCTACGA |
| | | AAATCCAACCTA |

Figure 3:
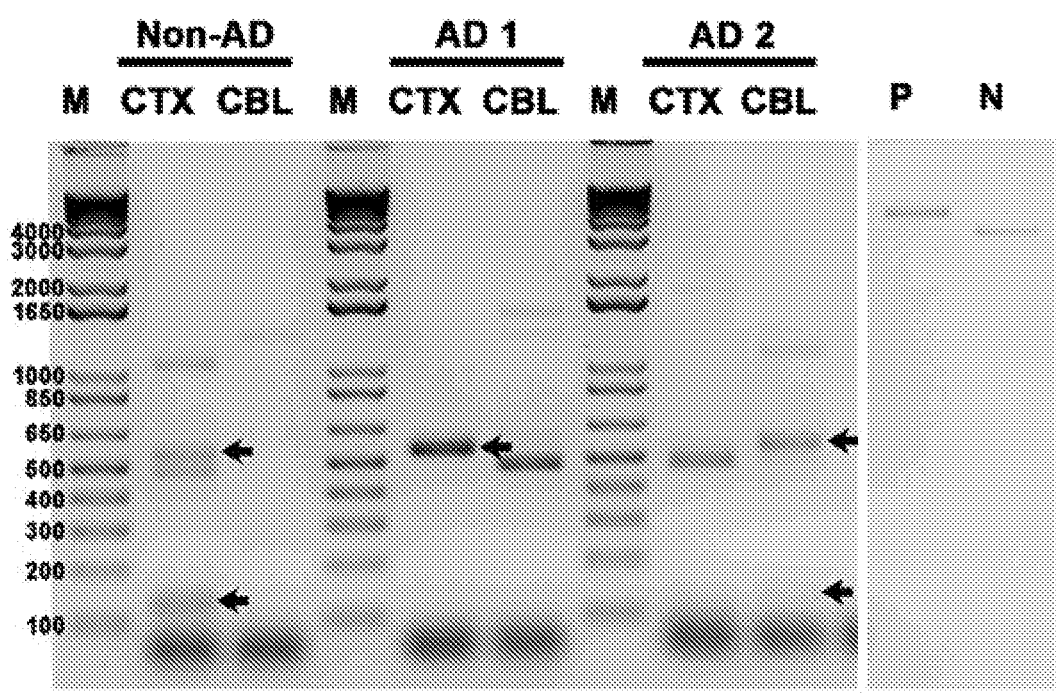
FIG. 3 illustrates a gel electrophoresis of RT-PCR from neurons isolated from cortices (CTX) and cerebellums (CBL) from non-diseased (Non-AD) postmortem brains and Alzheimer's disease (AD) brains. Arrows indicate positive signals corresponding to signal from Southern blot.
Figure 4:
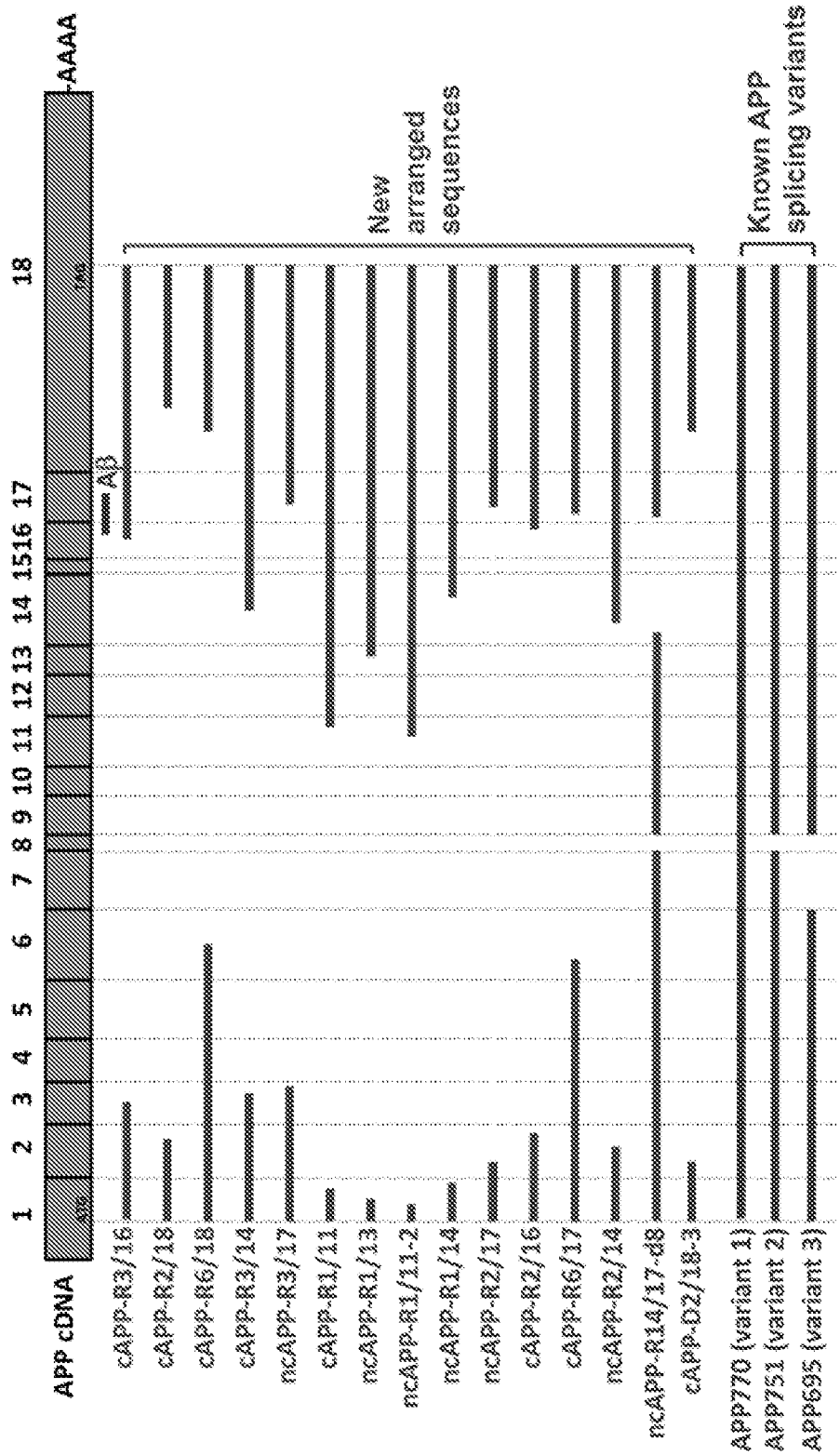
FIG. 4 illustrates exemplary non-classical variants.

The remaining PCR products were run on another agarose gel, and the bands corresponding to the positive signals (indicated by arrows) on nylon membranes were excised (FIG. 3). Excised PCR products were cloned and sequenced for variant analysis. Following sequencing, non-classical variants as seen FIG. 4 were identified.

Example 2. cDNA Library

A cDNA library was prepared from populations of 50 nuclei from non-diseased (Non-AD) and Alzheimer's disease (AD) brains with lambda phage library system (Clonetech Laboratories).

Percentages of non-classical variants cAPP-R3/16, ncAPP-R2/17, ncAPP-R1/13, and cAPP-R1/11 were determined in Non-AD and AD nuclei as seen in Table 4.

TABLE 4

| Non-classical Variant | Non-AD | AD |
|---|---|---|
| CAPP-R3/16 | 25% | 89.4% |
| ncAPP-R2/17 | 75% | 0% |
| ncAPP-R1/13 | 0% | 5.3% |
| CAPP-R1/11 | 0% | 5.3% |

Figure 5A:
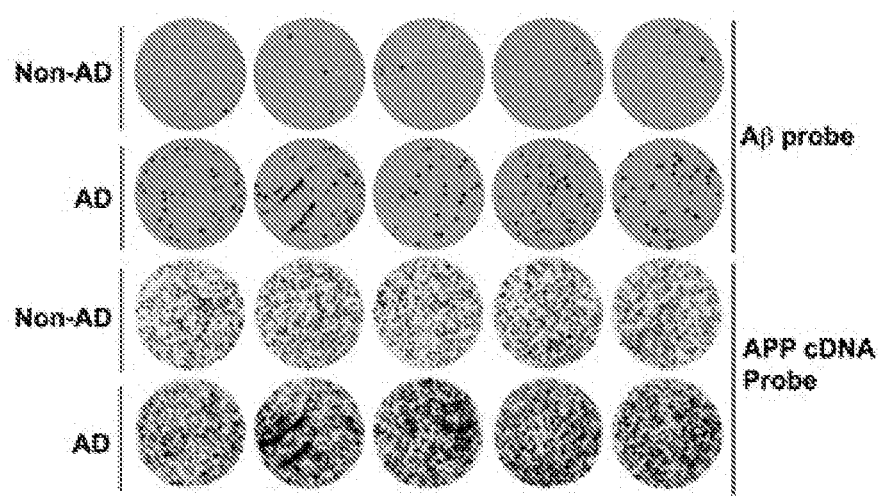
FIG. 5A illustrates amyloid beta positive clones from non-diseased (Non-AD) brains and Alzheimer's disease (AD) brains detected with amyloid beta (Aβ) probes and APP cDNA probes.
Figure 5B:
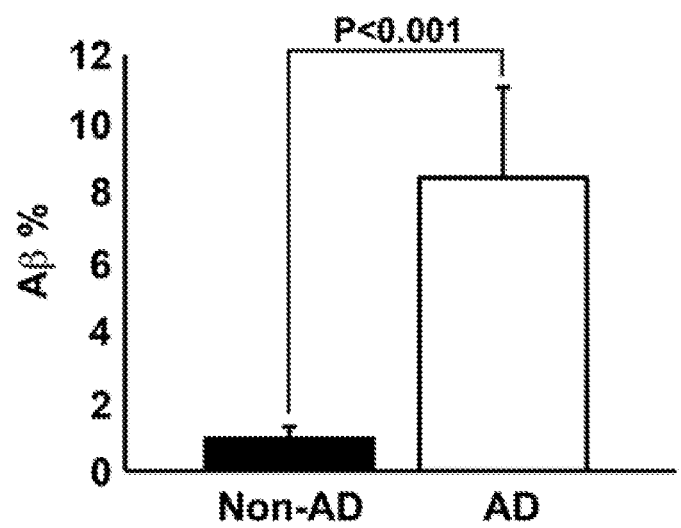
FIG. 5B illustrates a graph of percentage of amyloid beta in non-diseased (Non-AD) brains and Alzheimer's disease (AD) brains.
Figure 6:
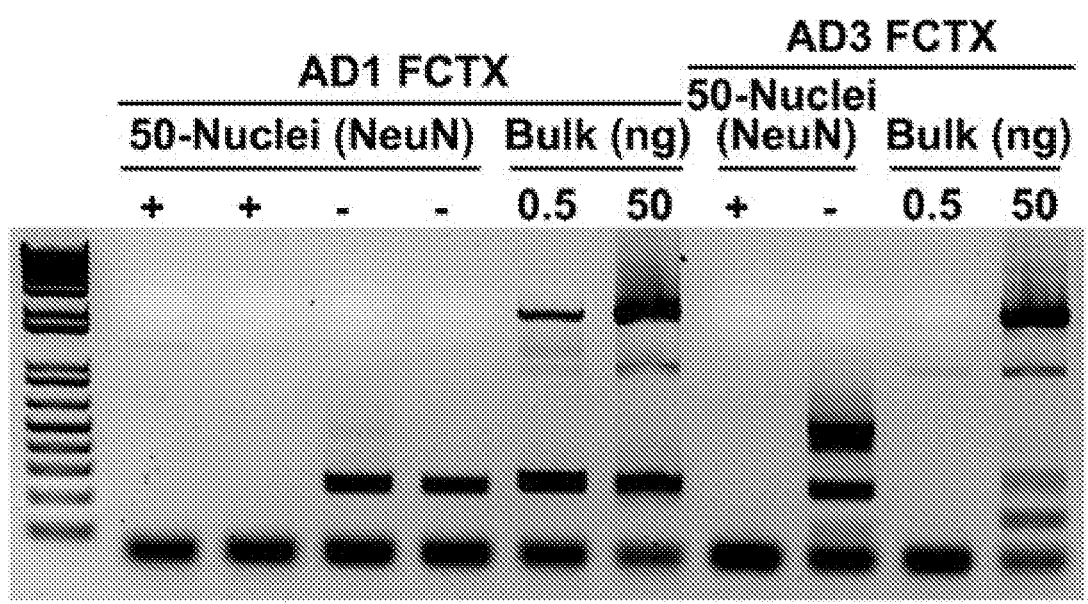
FIG. 6 illustrates a gel electrophoresis of RT-PCR from frontal cortices of Alzheimer's disease (AD) brains (AD1 and AD3) in sorted neuronal and non-neuronal nuclei and bulk RNA.

Percentages of amyloid beta positive phage clones from Non-AD and AD brains were also determined using probes for amyloid beta (GATGCAGAATTCCGA-CATGACTCAGGATATGAAGTTCATCATCAAAAAT-TGGTG TTCTTTGCAGAAGATGTGGGTT-CAAACAAAGGTGCAATCATTGGACTCATGGTGG GCGGTGTTGTCATAGCG) (SEQ ID NO: 22) and APP cDNA (FIG. 5A). A significant increase in percentage of amyloid beta was seen in AD brains than non-AD brains (FIG. 5B). Comparing APP mRNA in sorted nuclei or bulk RNA, FIG. 6 shows that full-length APP mRNA is mainly in the cytoplasm.

Example 3. Non-Classical Variants Detected in Genomic DNA

Neuronal nuclei were sorted from human postmortem frontal cortices from non-diseased and Alzheimer's disease brains. Genomic DNA was extracted and purified using DNeasy Blood and Tissue Kit (Qiagen, Valencia, Calif.). Purified genomic DNA was used as a template for PCR amplification using primers for APP comprising a forward primer (ATGCTGCCCGGTTTGGCA) (SEQ ID NO: 23) and a reverse primer (CTAGTTCTGCATCTGCT-CAAAGAACTTG) (SEQ ID NO: 24). PCR products amplified with APP primers were run on an agarose gel (FIG. 7A) as well as a no template control (NTC). In addition to APP, PSEN1 primers were used to amplify the purified genomic DNA and were run on an agarose gel with a positive control (PC) and a no template control (NTC) (FIG. 7B). PCR products were cloned and sequenced for variant identification.

Figure 7A:
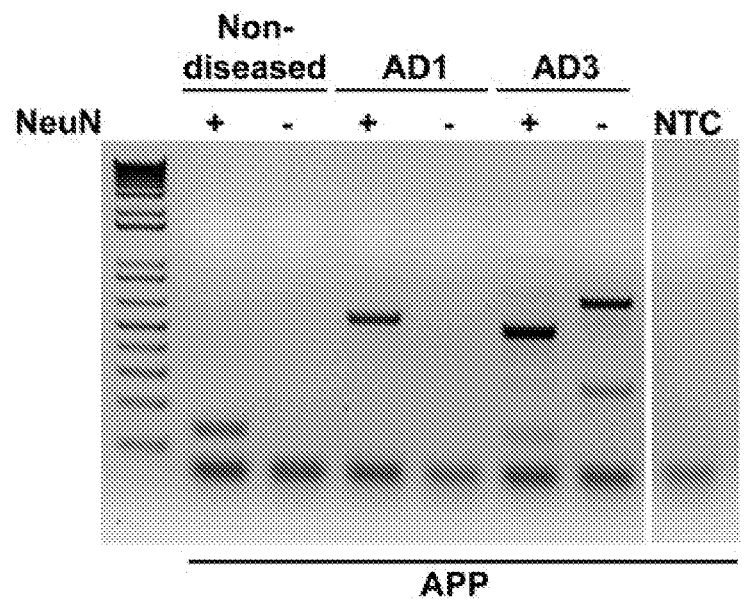
FIG. 7A illustrates a gel electrophoresis of PCR for genomic DNA isolated from frontal cortices of non-diseased brains and Alzheimer's disease (AD) brains (AD1 and AD3) with APP primers. NTC represents no template control.
Figure 7B:
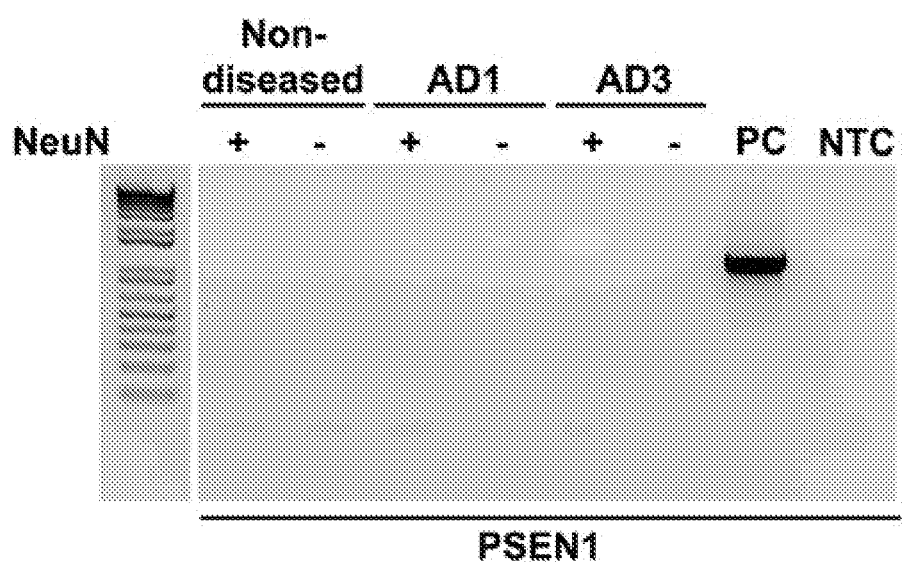
FIG. 7B illustrates a gel electrophoresis of PCR for genomic DNA isolated from frontal cortices of non-diseased brains and Alzheimer's disease (AD) brains (AD1 and AD3) with Presenilin 1 (PSEN1) primers. NTC represents no template control, and PC represents positive control.

Referring to FIG. 7A, non-classical variants of APP were identified in neuronal and non-neuronal gDNA. Using primers for PSEN1, non-classical variants were not identified on gDNA (FIG. 7B).

Example 4. Quantitative Polymerase Chain Reaction of Non-Classical Variant cAPP-R3/16 on DNA Populations of 20 nuclei were isolated and analyzed by quantitative polymerase chain reaction (qPCR) to detect non-classical variant cAPP-R3/16.

Genomic DNA from sorted nuclei was extracted by QuickExtract DNA extraction solution (Epicentre) and preamplified by TaqMan PreAmp Master Mix (Thermo Fisher Scientific). Standard qPCR reactions using TaqMan probe based assays were performed in triplicate. Reactions were run on a BioRad qPCR thermocycler using TaqMan Real-Time PCR Master Mix (Thermo Fisher Scientific). The crossing threshold (Ct) was determined for primers for cAPP-R3/16, PSEN1 and TERT within the linear region of the amplification curve.

Figure 8:
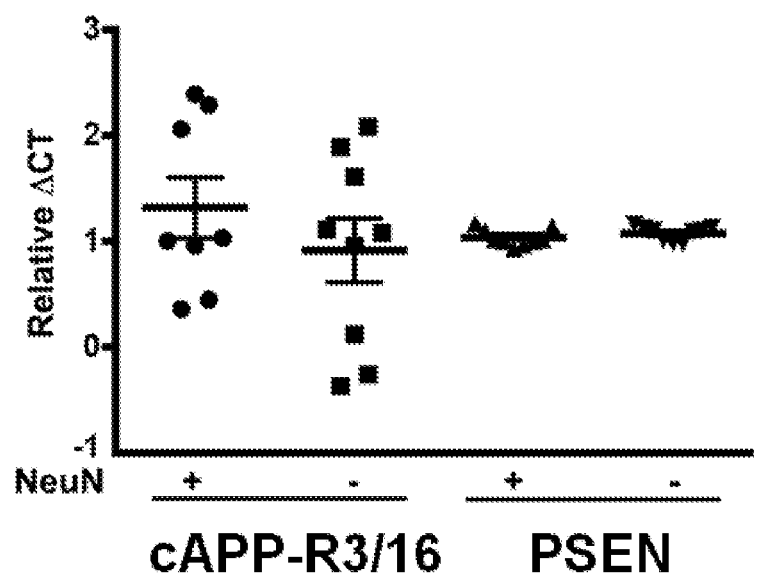
FIG. 8 illustrates a graph of relative ΔCT for neuronal and non-neuronal samples in which cAPP-R3/16 and PSEN are detected.

Referring to FIG. 8, the non-classical variant cAPP-R3/16 was quantitatively detected in neuronal and non-neuronal cells with a wide range of distribution whereas as PSEN1 was with a consistent distribution.

Example 5. Pull-Down Assay of Non-Classical Variants

Non-classical variants were detected using a DNA pull-down assay. The in vitro transcribed RNA probe sequence used for DNA pull-down was APP cDNA sequence. The pull-down sequences were cloned and sequenced for APP variant analysis.

Example 6. DNA In Situ Hybridization of Neuronal Cells

Neuronal nuclei were isolated from frontal cortices of AD brains as described in Example 1 and analyzed for intron/exon and exon/exon sequences of APP.

gDNA in nuclei were hybridized with intron/exon and exon/exon probes and labeled with different colors by chromogenic method. Briefly, neuronal nuclei from AD brains were fixed and sorted for NeuN positivity, and dried onto slides. Neuronal nuclei were treated with RNase cocktail (Ambion) for 1 hour at 40° C., following by hydrogen peroxide treatment for 10 minutes at room temperature and protease treatment for 10 minutes at 40° C. DNA denaturation was performed by incubating the slides with 0.58× SSC, 70% formamide, and 0.1% SDS for 20 minutes at 80° C. DNA in situ hybridization probes were incubated with samples at 40° C. overnight.

Chromogenic developing procedures were performed according to manufacturer's protocol (Advanced Cell Diagnostics). Slides were then visualized by microscopy.

Figure 9:
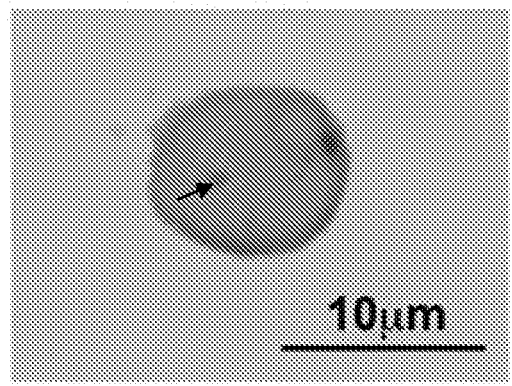
FIG. 9 illustrates genomic rearrangements in an Alzheimer's disease (AD) neuronal nuclei detected by DNA in situ hybridization.

As seen in FIG. 9, genomic rearrangements were observed. Specifically, exon-exon junctions as seen in the arrow were present.

Example 7. RNA In Situ Hybridization of Tissue

Brain samples from patients with AD were isolated and sectioned, and non-classical variants were analyzed.

Non-classical variants were analyzed using RNA in situ hybridization. 10 μm human AD frontal cortices were sectioned and fixed by neutral buffered formalin. Fixed tissue sections were treated with hydrogen peroxide for 10 minutes at room temperature, followed by target retrieval and protease treatment. RNA in situ hybridization probes were incubated with samples for 2 hours at 40° C. Chromogenic developing procedures were performed according to manufacturer's protocol. After RNA in situ hybridization, anti-Aβ monoclonal antibody (MOAB, Millipore) was incubated with sample at room temperature overnight. Horseradish peroxidase based developing method was used for signal detection. Slides were then visualized by microscopy at 200× and 630× magnification.

Figure 10:
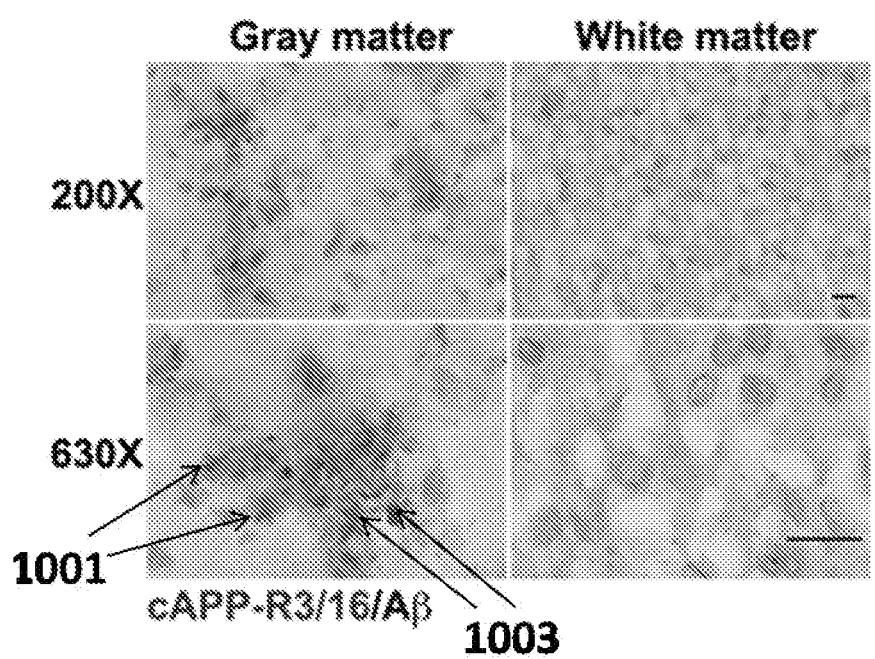
FIG. 10 illustrates intraexonic rearrangements in tissue sections from an Alzheimer's disease (AD) brain detected by RNA in situ hybridization of non-classical variant cAPP-R3/16 (arrow, 1001). Amyloid beta (Aβ) is stained in brown (arrow, 1003). Tissue sections are visualized at 200× and 630× magnification.

As seen in FIG. 10, intraexonic rearrangement junctions were observed. Specifically, the non-classical variant cAPP-R3/16 (red, 1001) was detected near amyloid beta plaques (brown, 1003).

Example 8. Single Molecule Real-Time Sequencing of Non-Classical Variants

Non-classical variants were detected by single molecule real-time (SMRT) sequencing.

RNA Samples were prepared from 2 AD temporal lobes. Methods for preparation of RNA for sequencing were provided according to manufacturer's instructions (Pacific Biosciences). Briefly, target cDNA was prepared and captured by xGene lockdown probes. cDNA of interest was then ligated to adaptors and ready for SMRT sequencing with RSII sequencer.

Figure 11:
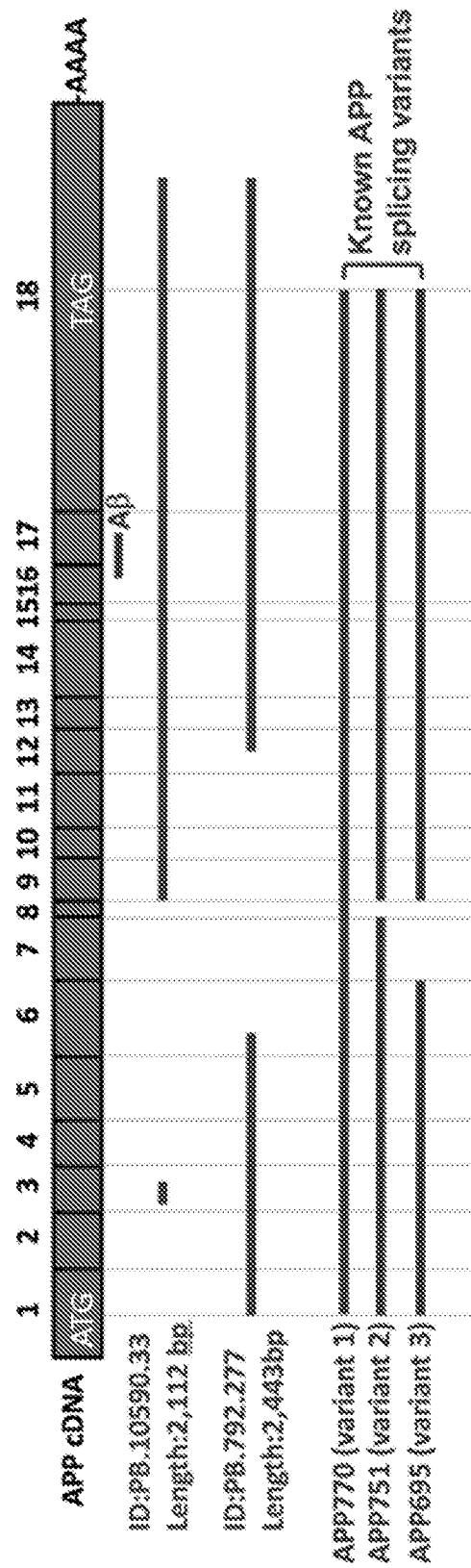
FIG. 11 illustrates non-classical variants detected by single molecule real-time sequencing.

Following cDNA sequencing, non-classical variants were identified (FIG. 11).

Example 9. DNA In Situ Hybridization of Nuclei from AD and Non-Diseased Brains Non-neuronal and neuronal nuclei were isolated from non-diseased and AD brains as described in Example 1 and analyzed for exon-exon junctions and intraexonic rearrangements of APP. Non-classical variants were analyzed using DNA in situ hybridization. Briefly, nuclei dried on to slides were treated with RNase cocktail for 1 hour at 40° C., followed by hydrogen peroxidase treatment, target retrieval, protease treatment, and DNA denaturation. DNA in situ hybridization probes were incubated with samples at 40° C.

overnight. Chromogenic developing procedures were performed according to manufacturer's protocol. Probes used here were designed to detect exon 16 and exon 17.

Figure 12:
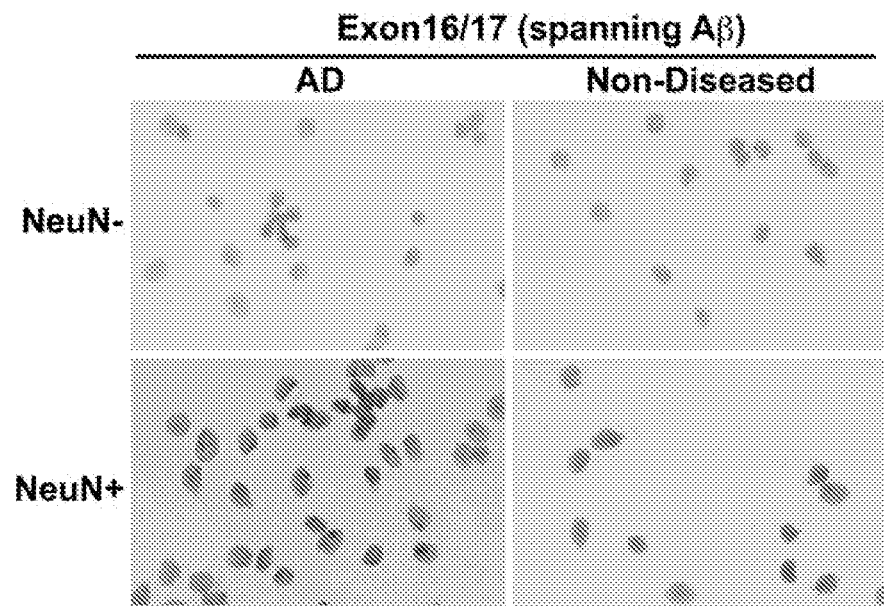
FIG. 12 illustrates the presence of exon 16 and exon 17 junction in neuronal and non-neuronal nuclei from non-diseased and Alzheimer's disease (AD) brains detected by DNA in situ hybridization.

Nuclei from neuronal and non-neuronal cells showed an increased signal in AD brains as compared to non-diseased brains (FIG. 12).

Example 10. Non-Classical Variants Expressed Protein

Non-classical variants were analyzed for ability to express protein.

Figure 13A:
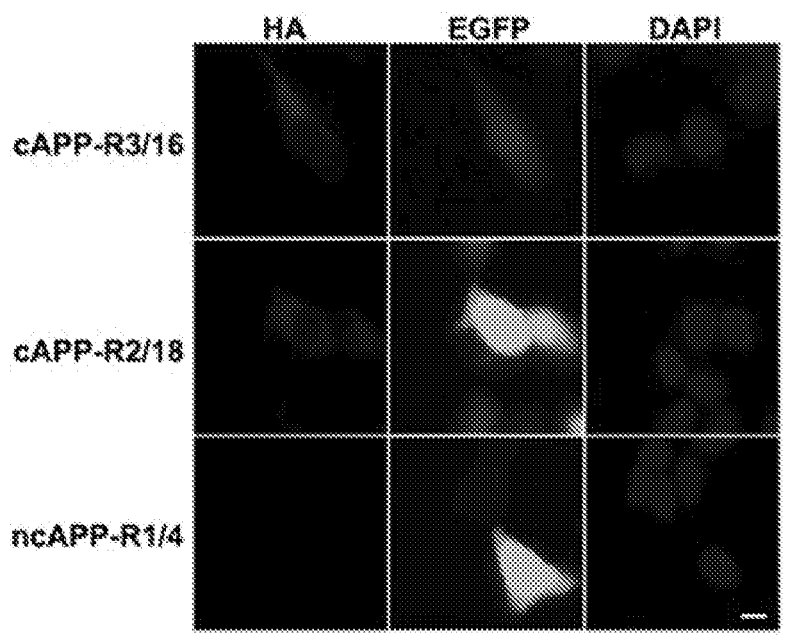
FIG. 13A illustrates immunofluorescence images of cells transfected with non-classical variants cAPP-R3/16, cAPP-R2/18, and ncAPP-R1/4 that are hemagglutinin (HA) epitope tagged (left panel). EGFP co-expression (middle panel) and DAPI staining (right panel) are shown.
Figure 13B:
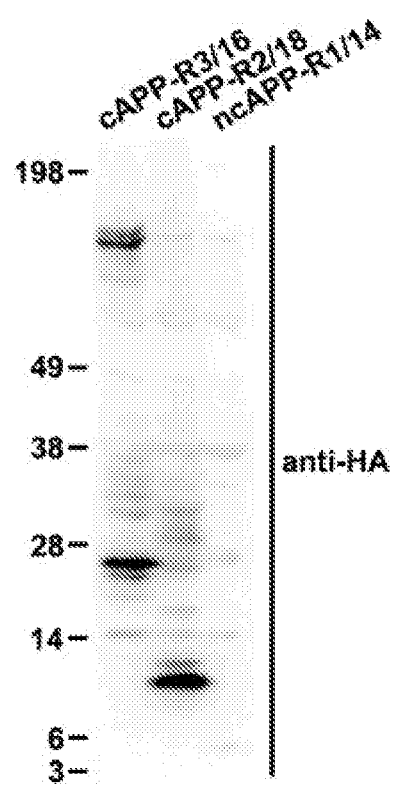
FIG. 13B illustrates a Western blot of cell lysate from cells transfected with non-classical variants cAPP-R3/16, cAPP-R2/18, and ncAPP-R1/4 that are hemagglutinin (HA) epitope tagged. The Western blot was probed with HA antibody.

Non-classical variants cAPP-R3/16, cAPP-R2/16, and ncAPP-R1/4 were epitope tagged with hemagglutinin (HA). The non-classical variants were transfected and expressed in cells. Referring to FIG. 13A, nuclei were stained with DAPI (right panel). The epitope tagged non-classical variants also heterologously expressed EGFP (center panel). Non-classical variants comprising coding regions expressed HA-tagged protein (left panel). Western blot for HA showed similar results in that non-classical variants comprising coding regions expressed HA-tagged protein (FIG. 13B).

Example 11. Non-Classical Variants Detected in Cells Expressing APP cDNA

Figure 14A:
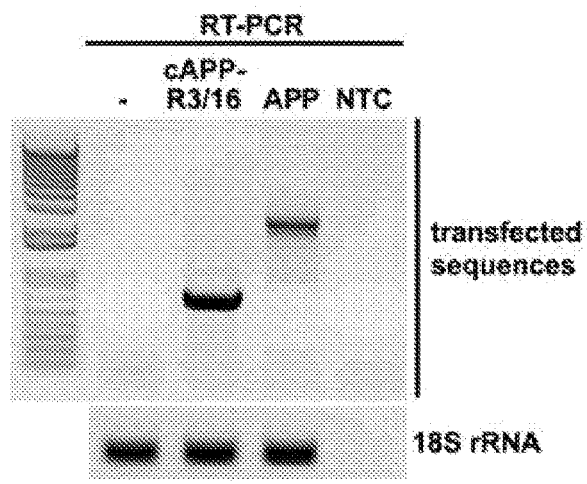
FIG. 14A illustrates a gel electrophoresis of RT-PCR of LN-229 cells transfected with non-classical variant cAPP-R3/16 or wild-type APP (APP).

LN-229 cells were transfected with vehicle, non-classical variant cAPP-R3/16, or wild-type APP cDNA (APP). RNA was extracted from the LN-229 cells and subject to reverse transcription PCR (RT-PCR). RT-PCR products were run on a gel. The non-classical variant cAPP-R3/16 and APP were detected (FIG. 14A).

Figure 14B:
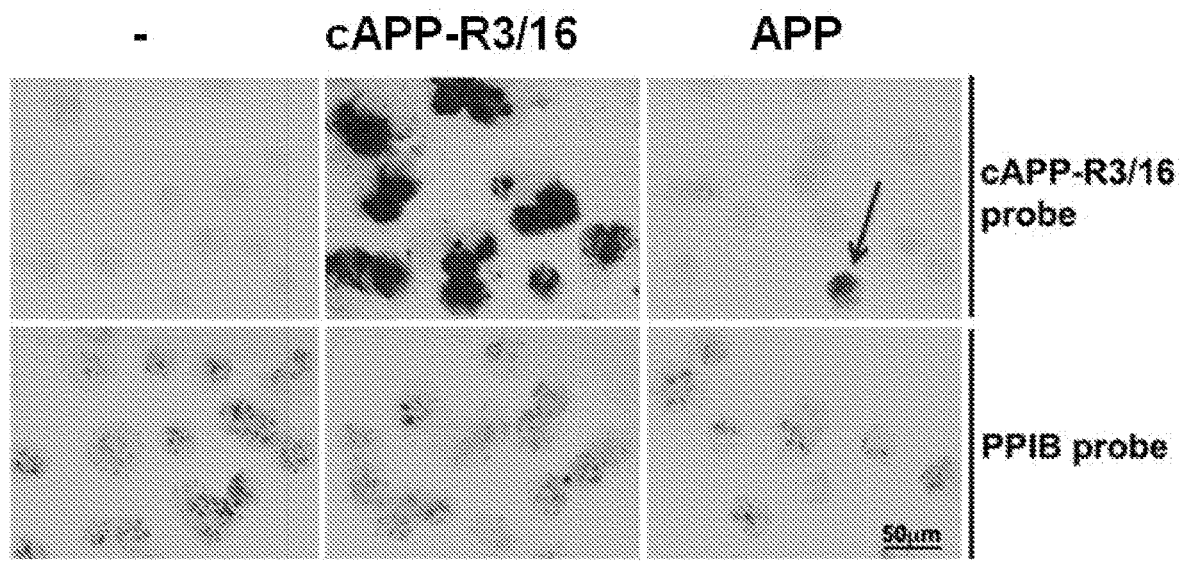
FIG. 14B illustrates cAPP-R3/16 induction in LN-229 cells transfected with cAPP-R3/16 or wild-type APP (APP) detected by DNA in situ hybridization using cAPP-R3/16 probe and PPIB probe as a positive control.

LN-229 cells were also transfected with vehicle, non-classical variant cAPP-R3/16, or APP for analysis by RNA in situ hybridization. Cells were fixed in neutral buffered formalin for 10 min at room temperature. Fixed cells were treated with hydrogen peroxide, following by target retrieval and protease treatment. RNA in situ hybridization probes were incubated with samples for 2 hours at 40° C. Chromogenic developing procedures were performed according to manufacturer's protocol. Probes used for staining were cAPP-R3/16 and PPM as a positive control. The non-classical variant cAPP-R3/16 was detected in cells expressing non-classical variant cAPP-R3/16 as well as in cells expressing wild-type APP (FIG. 14B).

Example 12. Methods for Analysis of Non-Classical Variants of APP

Nuclei Extraction and Fluorescence-Activated Nuclear Sorting (FANS)

For in situ, hybridization analyses, isolated nuclei were fixed in 1:10 diluted buffered formalin (Fisher Healthcare) for 5 minutes. Fixed or unfixed nuclei were then labeled with anti-NeuN rabbit monoclonal antibody (1:800) (Millipore, Germany) and Alexa Fluor 488 donkey anti-rabbit IgG (1:500) (Life Technology, Carlsbad, Calif.), and counterstained with propidium iodide (PI) (50 μ/ml) (Sigma, St. Louis, Mo.). Diploid NeuN positive and negative nuclei were gated by PI and immunofluorescence, and sorted into appropriate populations for RT-PCR, genomic DNA PCR, and in situ hybridization. FANS was performed with a FACS-Aria II.

RNA Extraction and RT-PCR

RNA extraction from 50-nuclei populations and bulk tissues were performed using Quick-RNA MicroPrep (Zymo Research, Irvine, Calif.) and RNAeasy Mini kits (Qiagen, Valencia, Calif.), respectively, according to manufacturer's protocol. OneStep Ahead RT-PCR (Qiagen, Valencia, Calif.) was used for RT-PCR with APP sense primer 5'-ATGCTGCCCGGTTTGGCA-3' (SEQ ID NO: 25) and APP anti-sense primer 5'-CTAGTTCTGCATCTGCT-CAAAGAACTTG-3' (SEQ ID NO: 26). Low annealing stringency PCR was carried out with the following thermal cycling steps: 95° C. 15 seconds, 55° C. 15 seconds, and 68° C. 2.5 minutes.

Southern Blotting

RT-PCR products were run on an agarose gel, denatured, and transferred to a positively charged nylon membrane. UV crosslinked membranes were incubated with denatured and purified $^{32}$P-labelled APP cDNA probes at 42° C. overnight. Blots were washed four times with increasing washing stringency. Images were developed by Typhoon (GE Healthcare Life Sciences) or Fujifilm FLA-5100 phosphorimager.

DNA Extraction and Genomic DNA PCR

DNA extraction from isolated neuronal nuclei populations was performed using DNAeasy and QIAamp DNA Mini kits (Qiagen, Valencia, Calif.) according to manufacturer's instruction. High annealing stringency PCR for APP was performed by FastStart PCR master (Sigma, St. Louis, Mo.) with 95° C. 30 seconds, 65° C. 30 seconds, and 72° C. 2.5 minutes, and Platinum SuperFi DNA polymerase (Life Technology) with 98° C. 10 seconds, 65° C. 10 seconds, and 72° C. 1.5 minutes. For PSEN1 PCR, the primer sequences were the following: sense 5'-ATGACAGAGTTACCTGCACC-3' (SEQ ID NO: 27) and anti-sense 5'-CTAGATATAAAATT-GATGGAA-3' (SEQ ID NO: 28). Thermal cycling steps were 95° C. 30 seconds, 52° C. 30 seconds, 72° C. 2 minutes, and 98° C. 10 seconds, 52° C. 10 seconds, 72° C. 1 minute for FastStart PCR master and Platinum SuperFi DNA polymerase, respectively.

Junction-Specific Genomic In Situ Hybridization (jgISH) and RNA-ISH

For jgISH pretreatment, sorted nuclei were dried on Plus Gold slides (Fisher Scientific, Pittsburgh, Pa.). Nuclei were then treated with RNase cocktail enzyme mix (1:50) (ThermoFisher) at 40° C. for 60 minutes, followed by 1:10 dilution buffered formalin fixation at room temperature for 5 minutes. After two washes with distilled water, slides were treated with hydrogen peroxide at room temperature for 10 minutes, target retrieval reagent at 95° C. for 15 minutes, followed by protease treatment at 40° C. for 10 minutes. Restriction enzyme was applied after protease treatment for 2 hours if needed. DNA was denatured (2×SSC, 70% formamide and 0.1% sodium dodecyl sulfate) at 80° C. for 20 minutes. After cooling down the slides to room temperature, probes were applied and incubated with nuclei at 40° C. overnight. Samples were then developed.

For RNA-ISH pretreatment, 10 μm fresh frozen human tissue sections were fixed by 1:10 dilution buffered formalin on ice for 10 minutes. After two washes with PBS, tissue sections were soaked in serial diluted ethanol (50%, 70% and 100%) for 5 minutes at each step. Slides were then treated with hydrogen peroxide at room temperature for 10 minutes, followed by protease at room temperature for 20 minutes. Probes were incubated with tissue sections at 40° C. for 2 hours. Hydrogen peroxide, 10× target retrieval buffer, proteases, probes (Ex16/17 targeting ACATGACTCAGGATATGAAGTTCATCATCAAAAAT-TGGTGTTCTTTGCA (SEQ ID NO: 29); IEJ 3/16 targeting TGCCAAGAAGTCTACCCTGAACTGCAGATCAC-CAAGATGGATGC (SEQ ID NO: 30, including sense and anti-sense probes) and reagents for signal developing were all purchased from Advanced Cell Diagnosis (ACD, Newark, Calif.). Nuclei or tissue sections were counterstained with hematoxylin. Zeiss AX10 Imager.M2 microscope and ZEN2 software were used for image acquisition. Images were thresholded, and foci number/size were quantified using ImageJ for statistical analysis.

SMRT Sequencing

Neuronal DNA was used as template for APP PCR by Platinum SuperFi DNA polymerase with high annealing stringency (98° C. 10 seconds, 65° C. 10 seconds, and 72° C. 1.5 minutes). Multiple PCR reactions were pooled and purified by DNA Clean and Concentrator-5 (Zymo Research, Irvine, Calif.) for SMRT sequencing library preparation. PCR products were repaired using SMRTbell template prep kit version 2.0 (PacBio) and purified using AMPure PB beads (PacBio). Adapters were ligated to DNA to create SMRTbell libraries. Sequencing polymerase was annealed, and the SMRTbell library was loaded using Magbead binding. Raw bam sequencing files were converted to fastq format using the ccs2 algorithm in SMRTLink Version 4.0. Reads were only included in the analyzed fastq file if 1) there were more than 20 passes of the sequencing polymerase over the DNA molecule in the zero mode waveguide well and 2) the read was calculated to possess a >0.9999 predicted accuracy.

Genomic Data Analyses with Customized Bioinformatic Algorithms

Novel algorithms were developed to detect and analyze exon rearrangement in genes of interest. The algorithms were specifically designed to analyze long-read sequences generated by Pacific Biosciences Sequel platform. A series of quality control (QC) procedures were performed prior to sequence processing to ensure high quality of reads being analyzed.

Quality Control: Consensus Sequence and Read Quality.

PacBio circular consensus sequences (CCS) reads with less than 20 passes were filtered out to ensure overall sequence quality. Quality score and read length distributions are examined: for APP gene PCR enriched sequences, average median read-wide Phred score is 93 and read length ranged from 64 to 2470 nucleotides. Reads for which the median Phred score was >85 were analyzed.

Quality Control: Sequencing Artifacts.

Errors in homopolymers were handled with a method combining quality score information and reference sequence at the beginning of a homopolymer. The CCS FASTQ files encoded uncertainty in the homopolymer run length in the first Phred score of each run. If this Phred score was lower than a threshold of 30, then this position was marked as a likely sequencing artifact and not a real variant.

PCR Primer Filter.

The reads were checked to ensure the correct start and end sites with forward and reverse PCR primer sequences. BLAST (command line tool "blastn" 2.6.0+) was used to align primer sequences in either orientation to each read with word size 13, gap open penalty 0 and gap extension penalty 2. Any read where both primers were not detected was filtered out. Furthermore, reads on the negative strand were reverse complemented in this step. BLAST seed length was optimized to avoid ambiguity and ensure sensitivity.

Alignment to APP Reference Sequences.

Ensembl reference sequence for APP protein was downloaded from the GRCh38 reference human genome assembly using the UCSC Genome Browser (http://genome.ucsc.edu/cgi-bin/hgGateway) with RefSeq accession number NM_000484.3. Since the PCR primers started at the start codon and end with the stop codon, sequences of exons 1 and 18 were trimmed to these positions so only the coding sequence of each of the 18 exons was kept and stored as a FASTA file. BLAST was then used to look for local alignment between 18 exons and each quality-filtered CCS read; blastn parameters used: -outfmt 6, -wordsize 25, -gapopen 0, -gapextend 2. These resulting alignment coordinates were used to mark regions of each read covered by exons for analysis of exon arrangements, lengths and patterns of exon-exon joins.

Construction and Retroviral Transduction of Human APP Exon 16/Exon 17 Concatamers.

Phosphorylated oligonucleotides (Integrated DNA Technologies) composed of human APP exon 16 and exon 17 sequences with BamHI and BglII restriction sites on the 5' ends were annealed, and ligated into the BamHI site of the retroviral expression vector 5-003-AB LZRSpBMN-linker-IRES-EGFP. Single and concatamerized oligonucleotide inserts were identified by PCR using primers flanking the BamHI insertion site and identified clones were sequenced to confirm insert copy number (GENEWIZ). Helper-free ecotropic virus was produced by transfecting DNA constructs (Lipofecatamine 2000, Thermo Fisher Scientific) with single or multiple copies of the oligonucleotide inserts into the retrovirus packaging line Phoenix-ECO. Forty-eight hours post-transfection, retroviral supernatants were harvested and 2 mL of selected virus was used for transduction of NIH-3T3 cells in 6 well plates. Retroviral transduction was carried out by removing the cell growth medium, replacing it with 2 mL of retroviral supernatant containing 4 µg/ml polybrene, and spinning at 25° C. for 1 hour at 2800 r.p.m. Forty-eight hours post-transduction, the percentage of GFP+ cells, as identified by flow cytometry, was used to evaluate the transduction efficiency. The following primers were used to produce the retroviral constructs: 16/17 Bam: 5'-GATCCACATGACTCAGGATATGAAGTTCATCAT-CAAAAATTGGTGTTCTTTGCAA-3', (SEQ ID NO: 31) and 16/17 BglII Rev: 5'-GATCTTGCAAAGAACACCAAT-TTTTGATGATGAACTTCATATCCTGAGTCATGTG-3' (SEQ ID NO: 32).

Cell Culture

NIH-3T3 cells were purchased from ATCC. Cells were maintained in Dulbecco's modified Eagle's medium (Invitrogen) containing 5% fetal bovine serum (Invitrogen) at 37° C. under 5% CO2.

Example 13. Non-Classical RNA Variants of APP in Populations of Neuronal Nuclei

Non-classical variants were analyzed in transcriptionally amplified RNA from populations of neuronal nuclei.

Figure 15A:
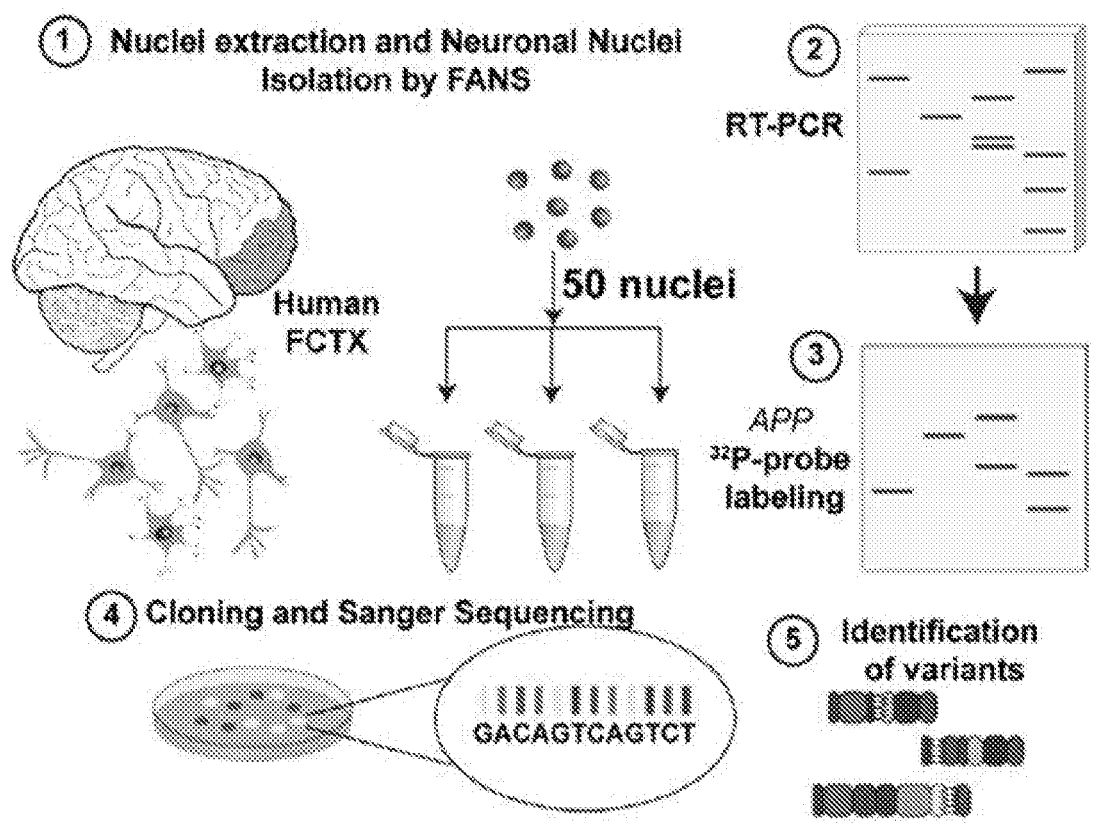
FIG. 15A illustrates a schematic for identification of non-classical RNA variants of APP from populations of neurons. (1) 50 neuronal nuclei were sorted from human prefrontal cortices (FCTX) by fluorescence-activated nuclear sorting (FANS) and used for (2) RT-PCR. Resulting RT-PCR products were screened by (3) Southern blot with $^{32}$P-labeled APP cDNA probes. (4) Bands with positive signals from duplicate gels were cloned and sequenced. (5) Non-classical variants were identified. Figure discloses SEQ ID NO: 33.

Non-classical variant sequences of APP were analyzed by RT-PCR in nuclei isolated by fluorescence activated nuclear sorting (FANS). The workflow (FIG. 15A) commenced with FANS to isolate neurons from both non-diseased and verified SAD prefrontal cerebral cortex (Table 5), which were run in parallel. Groups of 50 NeuN-positive neuronal nuclei were isolated and processed for RT-PCR (FIG. 15A). Validated primers capable of amplifying full-length APP cDNA (APP 770, NM_000484.3) were used, followed by agarose gel electrophoresis.

TABLE 5

| Brain Information. | | | | |
|---|---|---|---|---|
| Brain Name | Braak | Sex | PMI (Hours) | Age (years) |
| SAD-1 | 6 | F | 6 | 88 |
| SAD-2 | 6 | F | 12 | 88 |

TABLE 5-continued

Brain Information.

| Brain Name | Braak | Sex | PMI (Hours) | Age (years) |
|---|---|---|---|---|
| SAD-3 | 6 | F | 6 | 84 |
| SAD-4 | 6 | F | 4 | 86 |
| SAD-5 | 6 | M | 5 | 83 |
| SAD-6 | 6 | F | 10 | 72 |
| ND-1 | 1 | M | U | 87 |
| ND-2 | 1 | F | 72 | 83 |
| ND-3 | U | M | U | 83 |
| ND-4 | 1 | F | 12 | 80 |
| ND-3 | 1 | F | 18 | 93 |
| ND-6 | 2 | M | 12 | 94 |
| ND-7 | U | M | 12 | 69 |
| SAD-7 | 5 | F | 3.7 | 77 |

F = Female,
M = Male,
U = Unknown

Figure 15B:
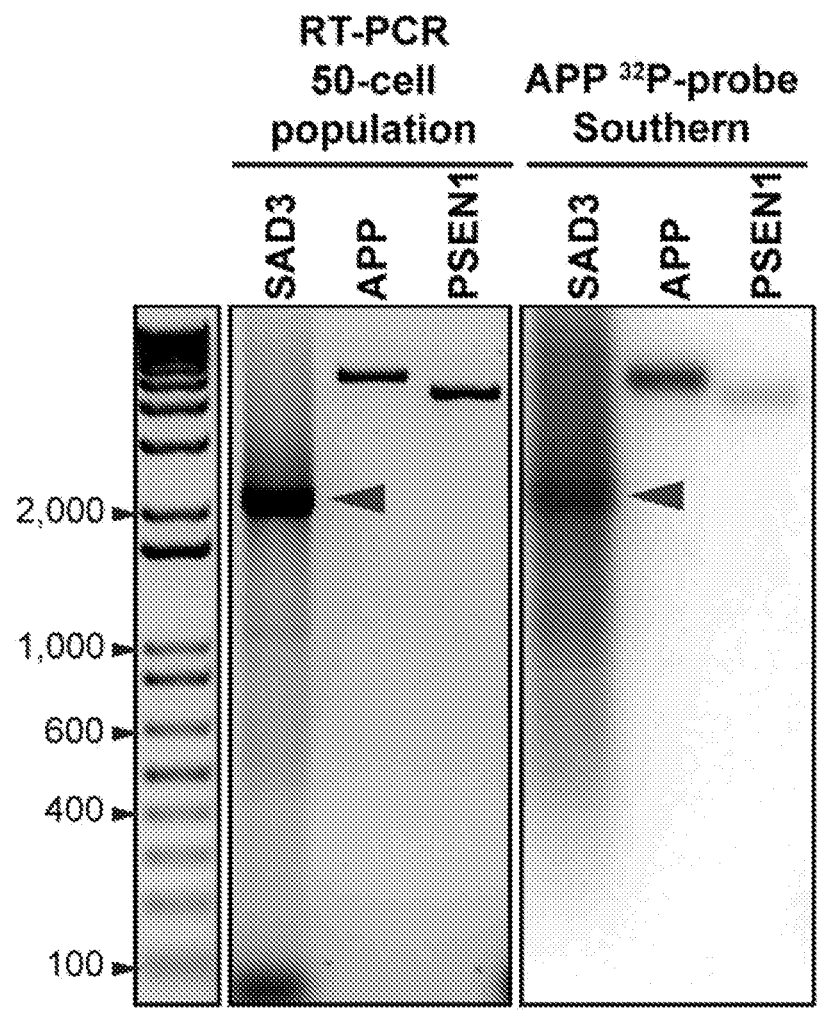
FIG. 15B illustrates a representative gel showing presence of canonical APP splice variants (red arrows).
Figure 15C:
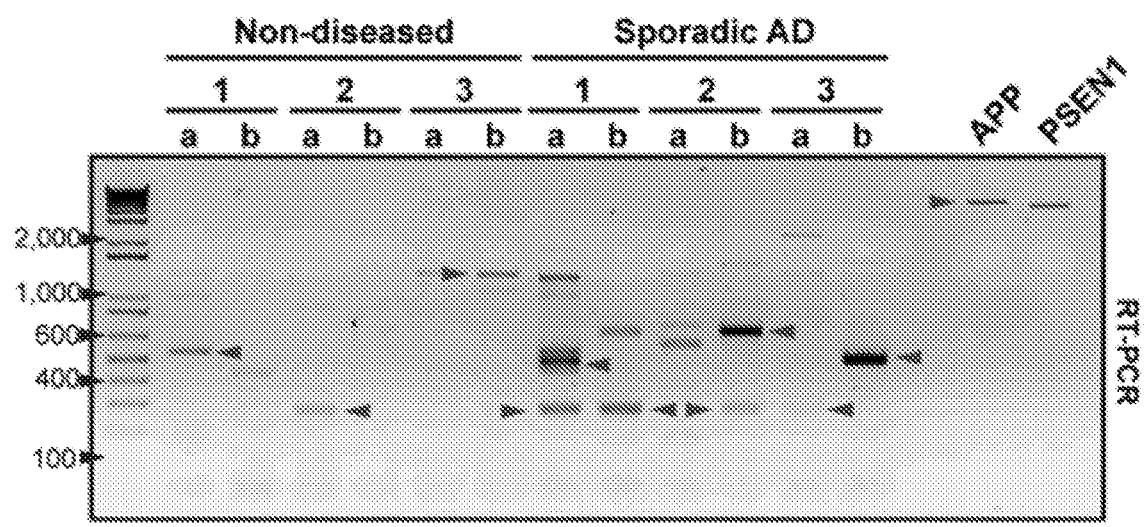
FIG. 15C illustrates electrophoresis of RT-PCR products from 3 non-diseased and 3 sporadic AD brains with two replicates each labeled as "a" and "b." APP and PSEN1 plasmids were run as positive and negative controls for Southern blotting, respectively.
Figure 15D:
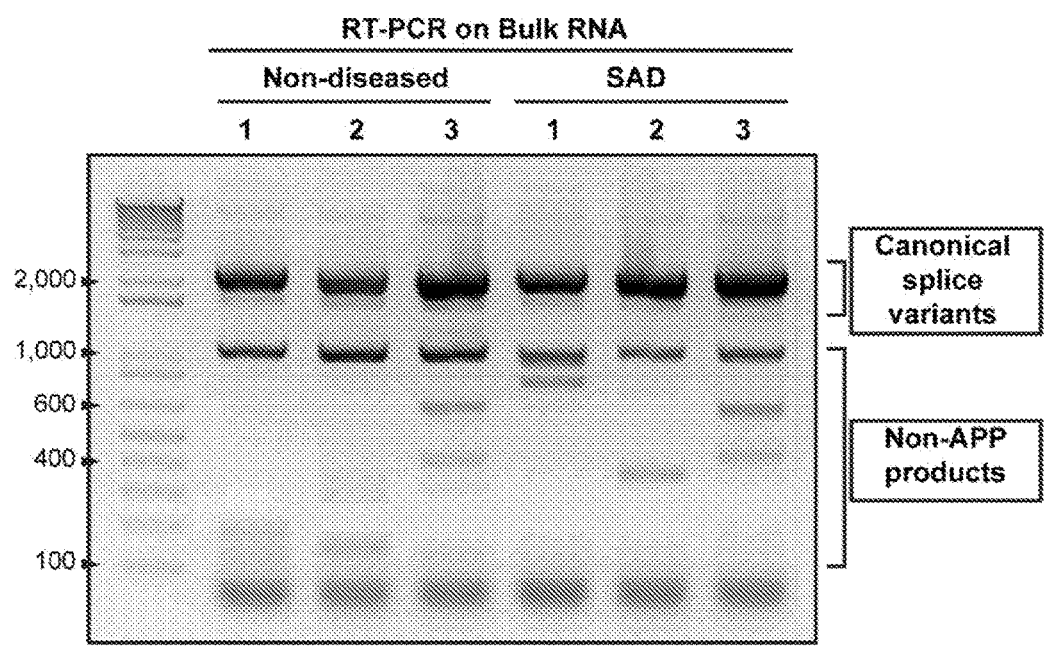
FIG. 15D illustrates a gel electrophoresis of RT-PCR for bulk RNA detecting canonical APP splice variants as major products. Bulk RNA from 3 non-diseased and 3 sporadic Alzheimer's disease (SAD) prefrontal cortices was used for APP RT-PCR. Major products detected were canonical APP splice variants.
Figure 15E:
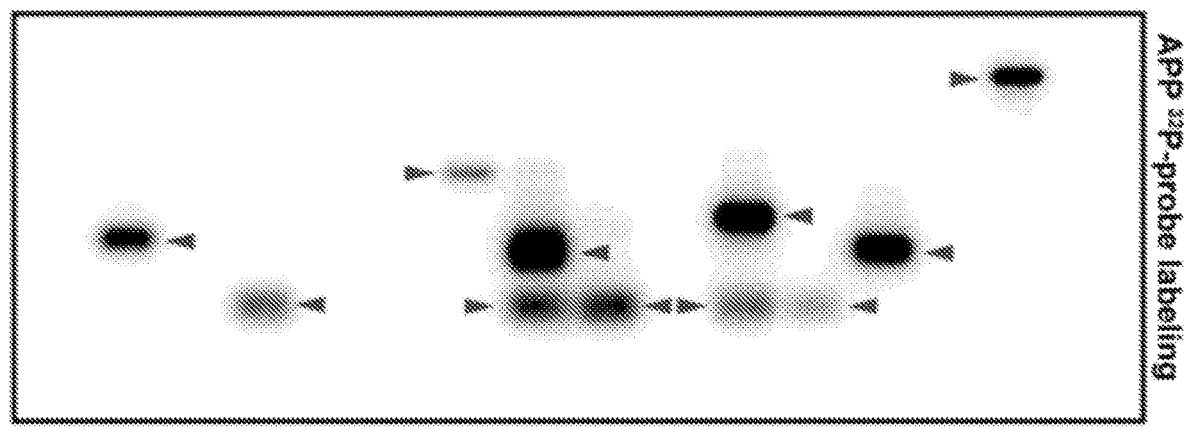
FIG. 15E illustrates Southern blot of RT-PCR products. Arrows indicate examples of corresponding bands from FIG. 15C that were cloned and Sanger sequenced. Non-reactive bands were sequenced and confirmed to be non-APP sequences.
Figure 15F:
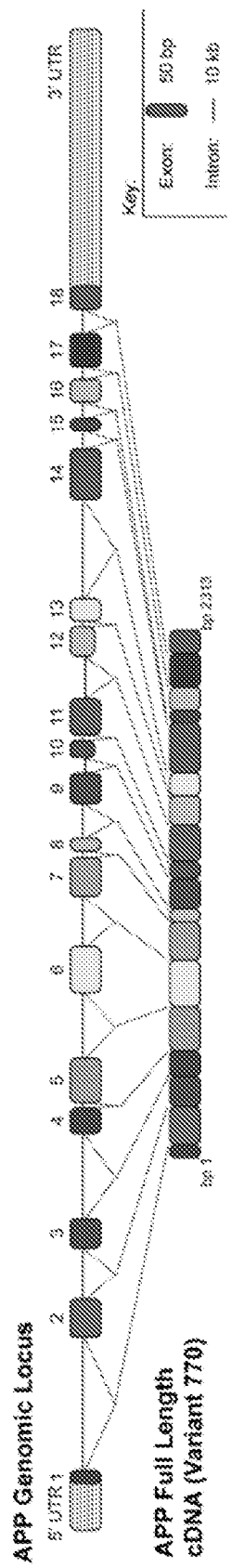
FIG. 15F illustrates a schema of structure of human APP genomic locus and spliced APP770 full length cDNA.
Figure 15G:
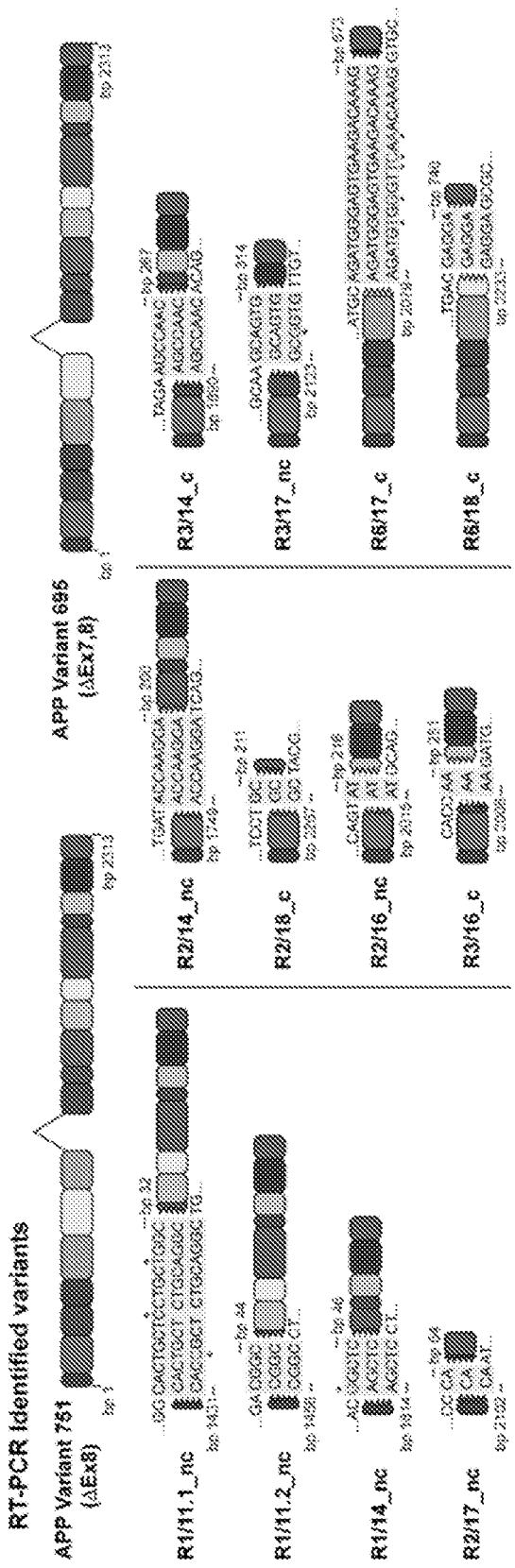
FIG. 15G illustrates schemas of non-classical RNA variants of APP identified by RT-PCR. Sequences of homology regions forming IEJs are shown. Variant sequences deviate from reference sequence are marked with asterisks. Naming scheme=R, RNA identified; #/#, exon::exon join; .#, for multiple unique joins; _c, coding (correctly translated APP protein after junction); _nc, non-coding (frame shift/premature stop codon after junction).

In small population RT-PCR, the splice variants APP 751 (NM_201413.2) and APP 695 (NM_201414.2) were detected (FIG. 15B). Smaller bands of varied sizes were also detected (FIG. 15C). RT-PCR on bulk RNA detected the highly expressed canonical APP splice variants as the major product (FIG. 15D). These RT-PCR products were Southern blotted with $^{32}$P-labeled APP cDNA probes (FIG. 15E), which produced positive bands from duplicate gels, that were cloned and Sanger sequenced. APP splice variants 751 and 695 as well as non-classical variants of APP were detected and characterized by loss of central exons with proximal and distal exons linked by intraexonic junctions (IEJs) (FIG. 15F-15H).

Figure 15H:
FIG. 15H illustrates schemas of sequence homology of non-classical RNA variants of APP at intraexonic junctions. Homology sequences of proximal and distal exons are shaded in gray. Middle sequence is the identified variant, top and bottom sequences are publicly available coding sequences from NM 000484.3 from the respective exons. Nucleotide variations are indicated an asterisk. Non-classical RNA variants identified by Sanger sequencing and PacBio data sets are shown with R and P, respectively. Figure discloses SEQ ID NOS 34-42, respectively, in order of appearance.
Figure 15I:
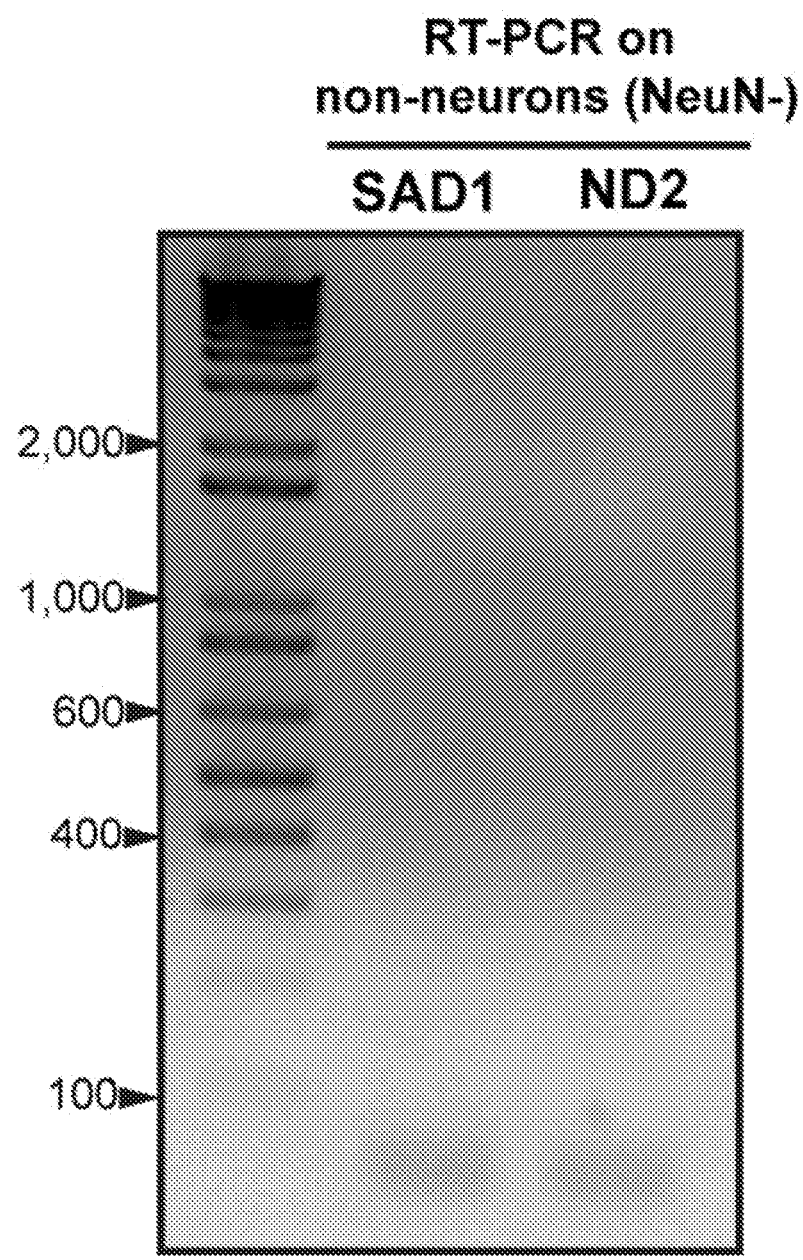
FIG. 15I illustrates a gel electrophoresis of non-neurons.
Figure 15J:
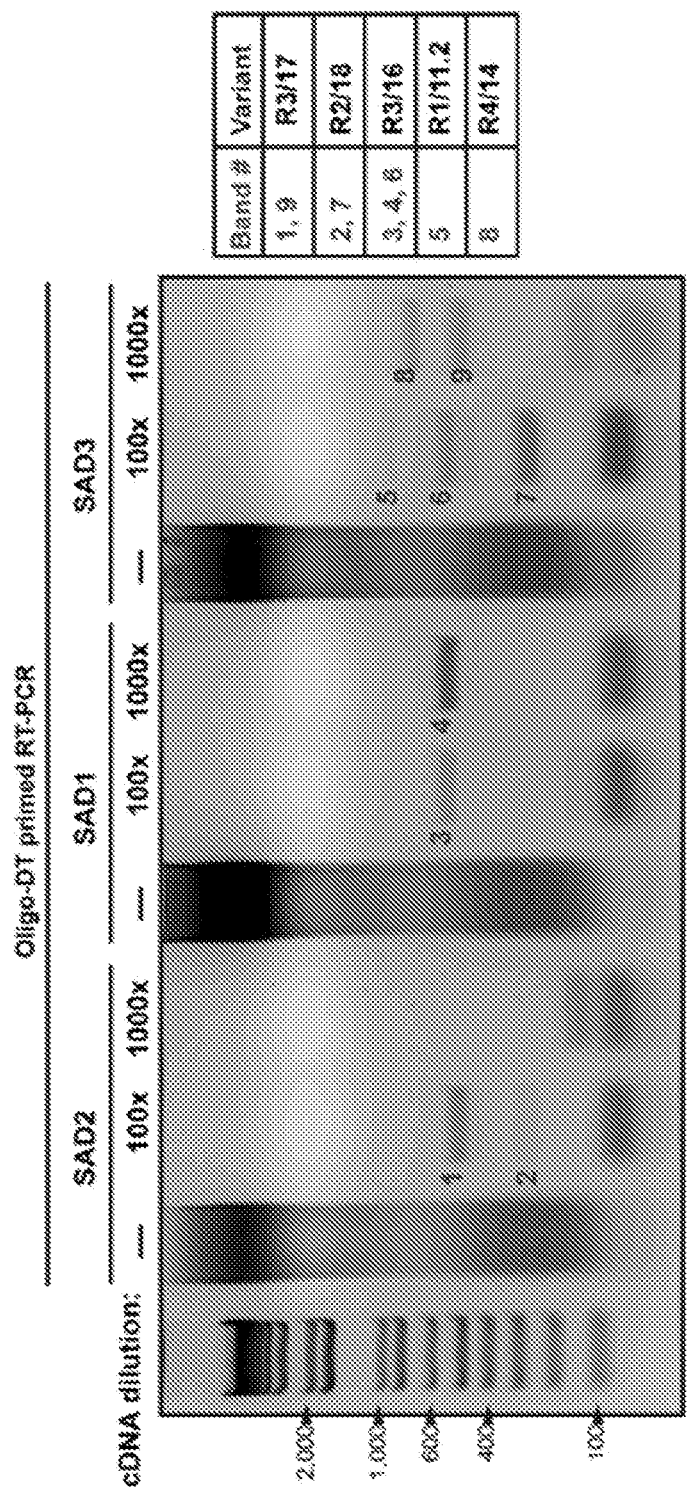
FIG. 15J illustrates gel electrophoresis of APP RNA variants identified from oligo-dT primed cDNA libraries from 50-cell populations of neuronal nuclei.
Figure 15K:
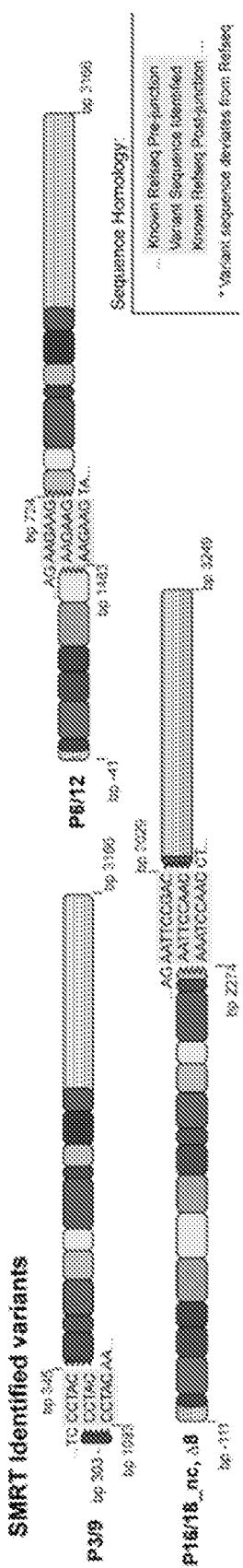
FIG. 15K illustrates APP RNA variants identified from 2 independent long-read single molecule real-time (SMRT) sequencing data sets.
Figure 15L:
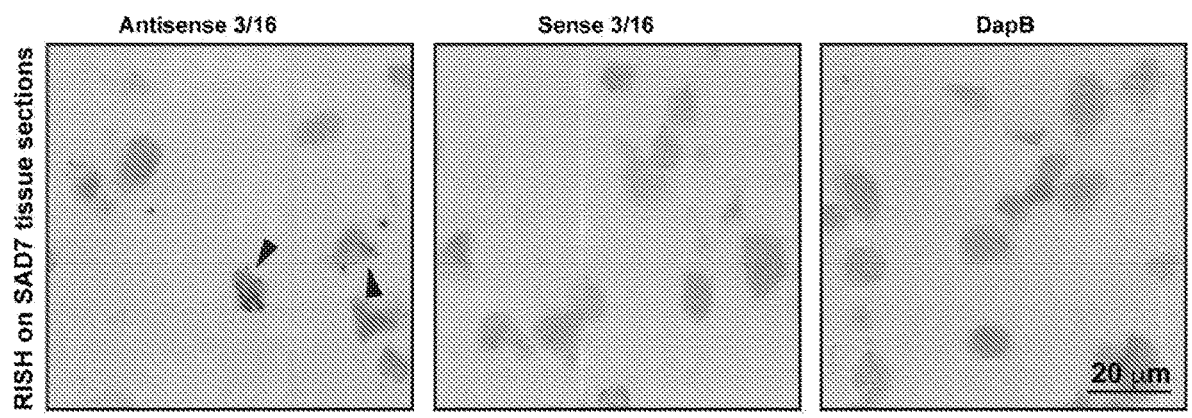
FIG. 15L illustrates images of RNA in situ hybridization (RISH) 3/16 signal from antisense probes showing cytoplasmic distribution of APP 3/16. Negative control sense probes and a bacterial gene targeting probe (DapB) showed no signals.

Twelve non-classical variant sequences with IEJs were identified (FIG. 15H). Non-neurons displayed no variants (FIG. 15I). IEJs were independently observed in 5 oligo-dT primed cDNA libraries; three from sorted SAD neuronal nuclei (FIG. 15J) and two from commercially produced long-read RNA-Seq data sets from whole SAD brain and SAD temporal lobes (FIG. 15K). One non-classical variant sequence was characterized by an IEJ between the $24^{th}$ nucleotide of exon 3 and $45^{th}$ nucleotide of exon 16 (FIG. 15L, "R3/16"). The sequence complementarity of joined exons was found in 12 IEJs ranging in overlap from 2 to 20 nucleotides (FIG. 15H and Table 6).

Example 14. Non-Classical Genomic cDNA Variants of APP in Populations of Neuronal Nuclei Non-classical variants of APP were analyzed in genomic DNA from populations of neuronal nuclei.

Figure 16A:
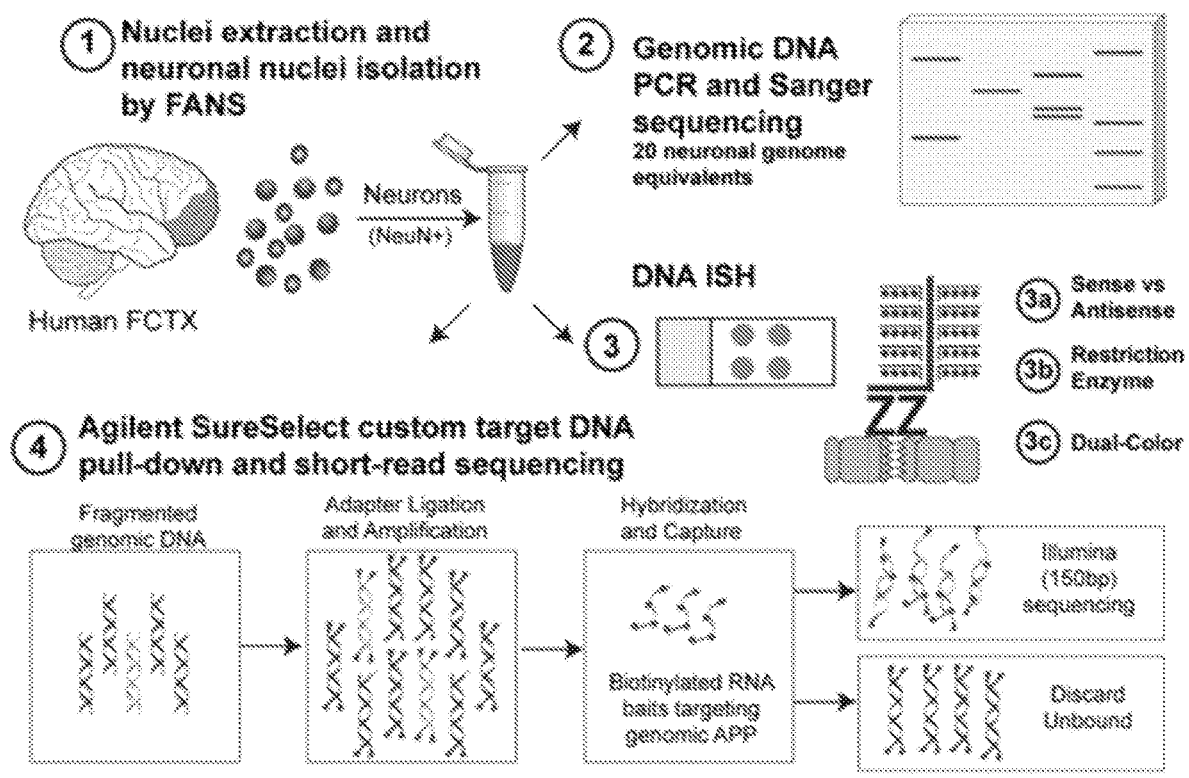
FIG. 16A illustrates a schema for analyzing non-classical genomic cDNA (gencDNA) variants of APP. (1) Neuronal nuclei from human prefrontal cortices (FCTX) were used for (2) genomic DNA PCR, (3) junction-specific genomic in situ hybridization (jgISH), and (4) custom target enrichment via Agilent SureSelect followed by deep sequencing.
Figure 16B:
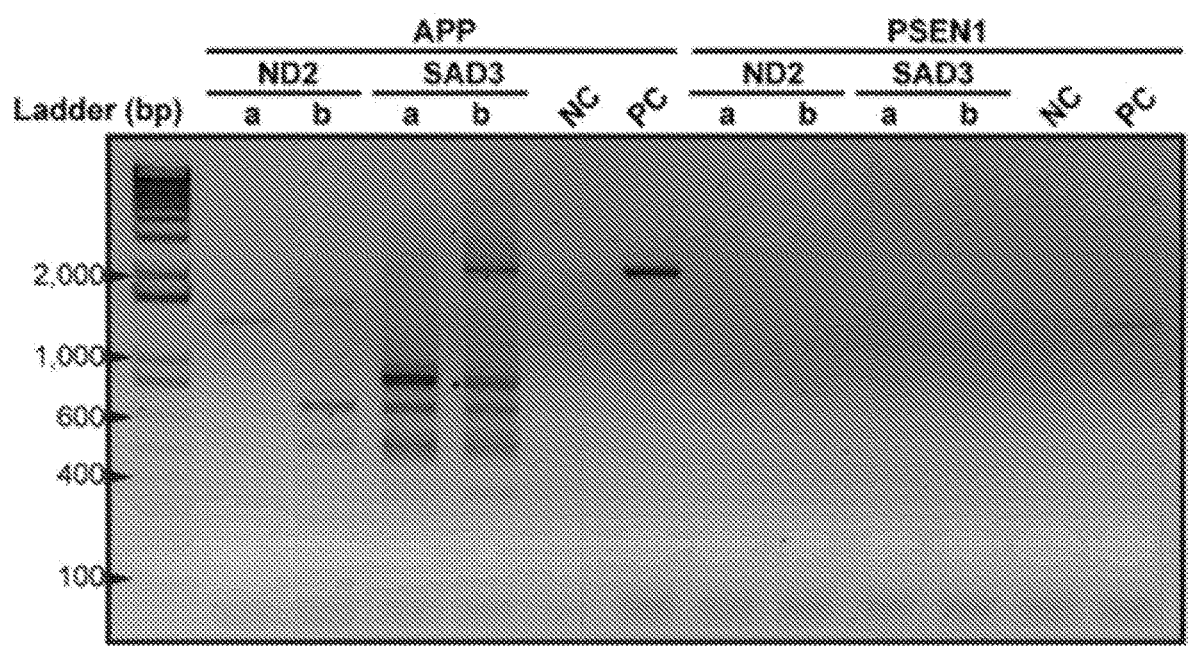
FIG. 16B illustrates a gel electrophoresis of genomic DNA PCR products with APP and PSEN1 primer sets using DNA from non-diseased (ND) and sporadic AD (SAD) neurons with two replicates each labeled as "a" and "b." Non-template control (NC) and positive control (PC) with indicated plasmids are shown.
Figure 16C:
FIG. 16C illustrates a schema showing 13 variants identified first by RT-PCR (APP-R) and DNA PCR (APP-D). Seven were identified in both methods, five by RT-PCR only, and one by DNA PCR only.
Figure 16C:
Figure 16C:
Figure 16C:
Figure 16C:
Figure 16C:
Figure 16C:
Figure 16C:
Figure 16C:
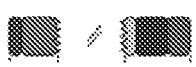
Figure 16C:
Figure 16C:
Figure 16C:
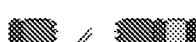
Figure 16C:
Figures 16D, 16E:
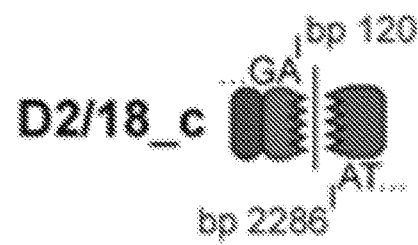
FIG. 16D illustrates one unique variant identified in RT-PCR of RNA.
FIG. 16E illustrates seven variants previously identified in RT-PCR of RNA.
Figure 16F:
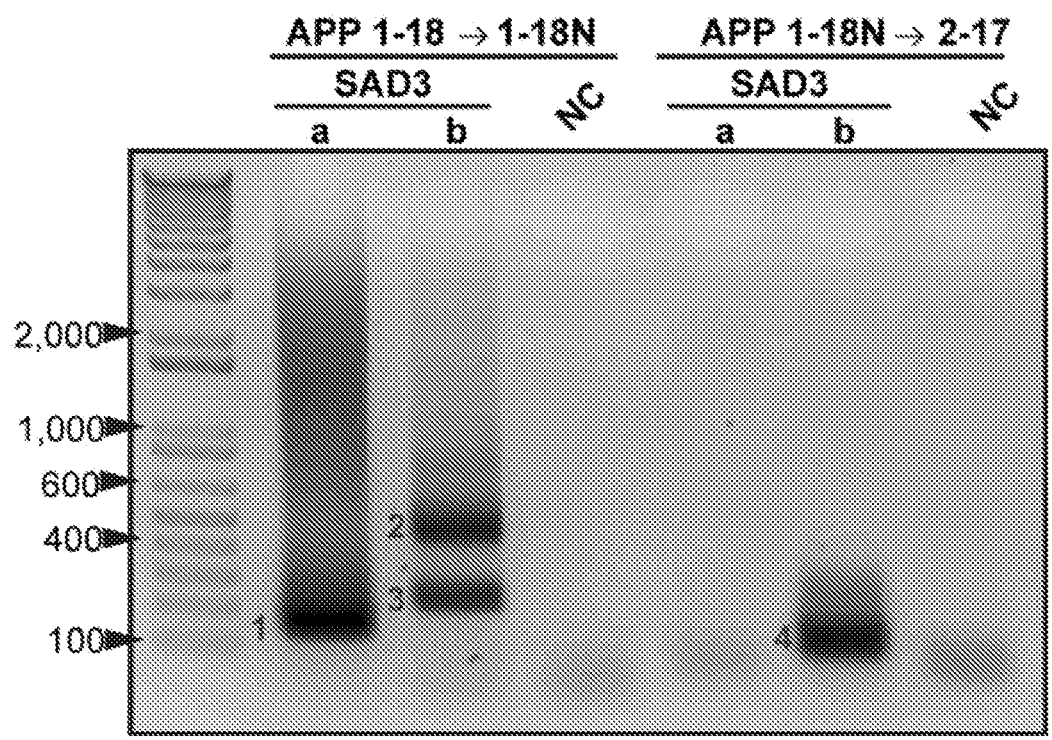
FIG. 16F illustrates a gel electrophoresis of nested PCR products for APP gencDNA identification with alternative APP primers (3 total sets, APP 1-18, APP 1-18N, and APP 2-17).
Figure 16G:
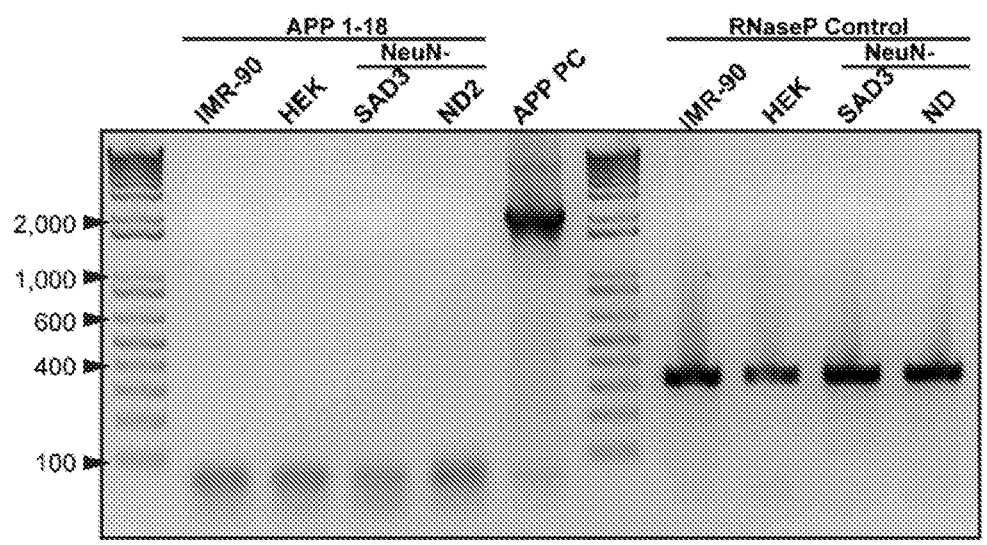
FIG. 16G illustrates a gel electrophoresis of APP 1-18 DNA PCR showing no products in non-neuronal cell types: IMR-90 (human lung fibroblast), HEK-293 (human embryonic kidney) and non-neuron (NeuN negative) genomic DNA from SAD and ND brains. RNaseP was used as a positive control.
Figure 16H:
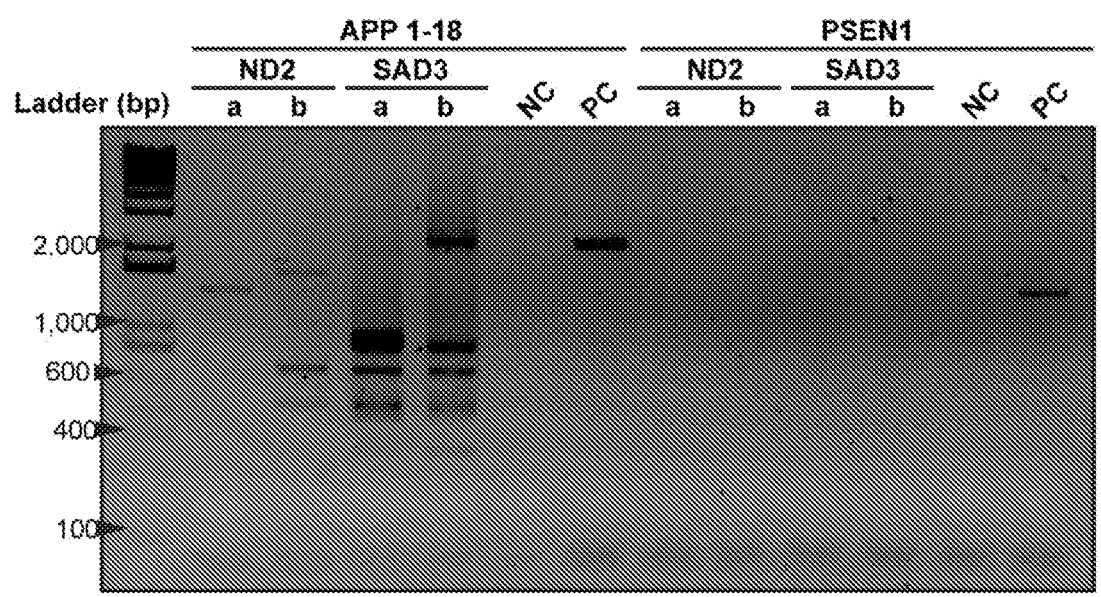
FIG. 16H illustrates a duplicate gel from FIG. 16B, with darker threshold and exposure to show the clear absence of PSEN1 bands.

High-stringency amplification using the APP primers described above was pursued on thoroughly RNased DNA obtained from sets of 20 neuronal nuclei from both normal and SAD brains (FIG. 16A). PCR of the ~300 kb, wild type APP genomic locus was not possible. See FIG. 15F. PCR of nuclear genomic DNA generated clear bands that were similar in size to non-classical variants from RNA-derived RT-PCR products (FIG. 16B, ~100-2,300 bp). Interrogation of a second AD related gene, Presenilin 1 (PSEN1), did not produce products from genomic DNA (FIG. 16B; 94 Kb). Cloning and Sanger sequencing identified multiple genomic cDNAs (gencDNAs) (FIGS. 16C-16E), including one unique sequence not previously identified in RNA (FIG. 16D). The presence of APP gencDNAs in neurons by use of multiple primer sets (FIG. 16F). gencDNAs were not detected in DNA isolated from human lung fibroblasts (IMR-90), human embryonic kidney cells (HEK 293), and non-neuronal nuclei from SAD and non-diseased brains (FIG. 16G). Interrogation of a second AD related gene, Presenilin 1 (PSEN1), did not produce products from genomic DNA (FIG. 16B and FIG. 16H).

TABLE 6

| Name | RNA PCR | DNA PCR | Coding or Non-coding | Start (bp) | Break Start | Break End | End | Sanger Sequence Homology | # of Basepairs in homology domain | Mismatched |
|---|---|---|---|---|---|---|---|---|---|---|
| RT-PCR Identified Variants |||||||||||
| R1_11.1 | Y | Y | Non-Coding | 1 | 32 | 1431 | 2313 | CACTGCTCTGCAGGC | 15 | 3 |
| R1_11.2 | Y | N | Non-Coding | 1 | 44 | 1456 | 2313 | CGGC | 4 | 0 |
| R1_14 | Y | Y | Non-Coding | 1 | 46 | 1814 | 2313 | AGCTC | 5 | 1 |
| R1_14 | Y |  | Non-Coding | 1 | 200 | 1749 | 2313 | ACCAAGGA | 8 | 0 |
| R2_16 | Y |  | Non-Coding | 1 | 216 | 2015 | 2313 | AT | 2 | 0 |
| R2_17 | Y | Y | Non-Coding | 1 | 64 | 2102 | 2313 | CA | 2 | 0 |
| R2_18 | Y | Y | Coding | 1 | 211 | 2267 | 2313 | GC | 2 | 0 |
| R3_14 | Y | Y | Coding | 1 | 267 | 1890 | 2313 | AGCCAAC | 7 | 0 |
| R3_16 | Y | Y | Coding | 1 | 251 | 2008 | 2313 | AA | 2 | 0 |
| R3_17 | Y | Y | Non-Coding | 1 | 314 | 2123 | 2313 | GCAGTG | 6 | 0 |
| R6_17 | Y |  | Coding | 1 | 673 | 2079 | 2313 | AGATGGGAGTGAAGACAAAG | 20 | 0 |
| R6_18 | Y |  | Coding | 1 | 740 | 2233 | 2313 | GAGGA | 5 | 0 |
| DNA PCR Identified Variants |||||||||||
| D2_18 |  | Y | Coding | 1 | 120 | 2287 | 2310 | N/A | N/A | N/A |
| D1_17 |  | Y | Non-Coding | 18 | 51 | 2159 | 2285 | N/A | N/A | N/A |
| D2_16 |  | Y | Non-Coding | 19 | 209 | 2016 | 2285 | TGCAGAATT | 9 | 1 |
| D2_17 |  | Y | Non-Coding | 18 | 64 | 2102 | 2285 | CA | 2 | 0 |
| D2_16.2 |  | Y | Non-Coding | 157 | 209 | 2016 | 2095 | TGCAGAATT | 9 | 1 |
| Commercially available PacBio RNA-Seg |||||||||||
| P3_9 | Y |  | Non-coding | 303 | 345 | 1093 | +853 | CCTAC | 5 | 0 |
| P6_12 | Y | n/a | Non-coding | −41 | 724 | 1483 | +853 | AAGAAG | 6 | 0 |
| P6_18 | Y | n/a | Non-coding | −111 | 2029 | 2274 | +936 | AATTCCGAC | 9 | 0 |

TABLE 6-continued

| Name | RNA PCR | DNA PCR | Coding or Non-coding | Start (bp) | Break Start | Break End | End | Sanger Sequence Homology | # of Basepairs in homology domain | Mismatched |
|---|---|---|---|---|---|---|---|---|---|---|
| DNA PCR on CHO cells: Induced Variants | | | | | | | | | | |
| iD1_17 | n/a | Y | Non-Coding | 1 | 51 | 2159 | 2313 | N/A | N/A | N/A |
| iD2_13 | n/a | Y | Coding | 1 | 170 | 1626 | 2313 | N/A | N/A | N/A |
| iD4_15 | n/a | Y | Missense* | 1 | 434 | 1920 | 2313 | TGA | 3 | 1 |
| iD6_18 | n/a | Y | Coding | 1 | 705 | 2269 | 2313 | T | 1 | 0 |

Name = First Identified in RNA "R" or DNA "D"_Exon joins; "Coding = Remains in frame after break, Non-Coding = Moves out of frame after break, premature stops.

Example 15. Non-Classical Genomic cDNA (GencDNA) Variants of APP in Single Nuclei Presence of APP gencDNA junctions within single neuronal genomes was analyzed using jgISH.

Figure 17A:
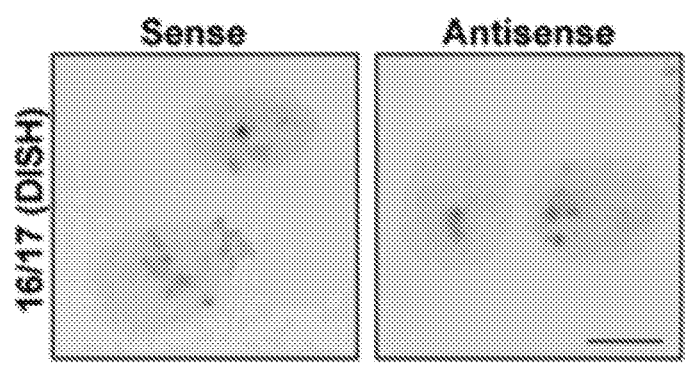
FIGS. 17A-17C illustrate jgISH performed with sense and anti-sense probes targeting APP exon 16 and exon 17 junction (Ex 16/17).
Figure 17B:
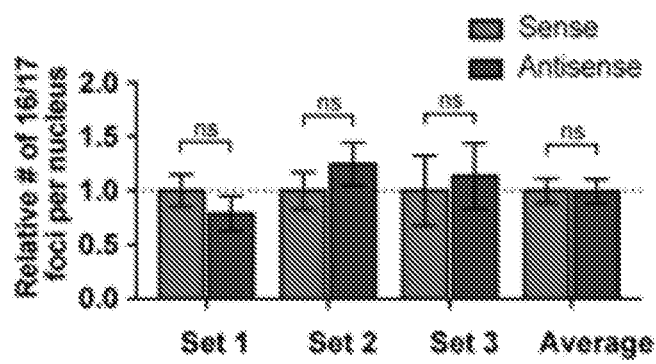
Figure 17C:
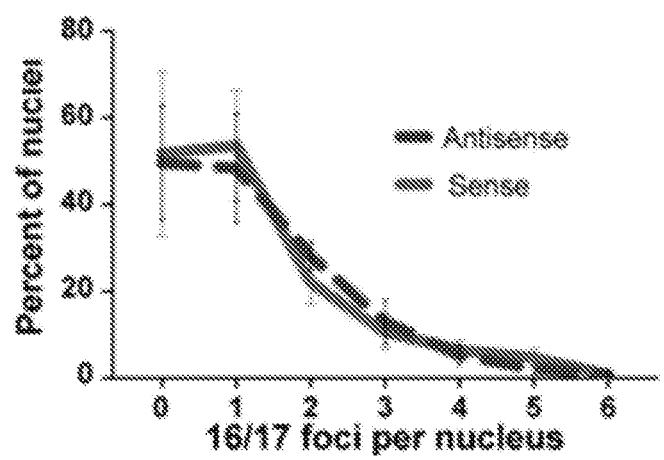
Figure 17D:
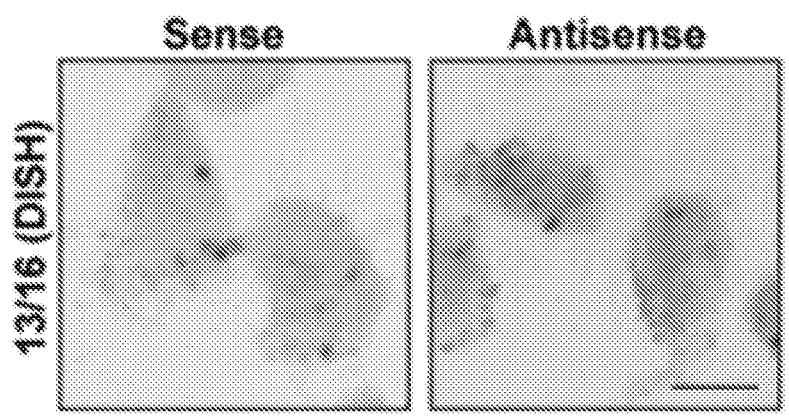
FIGS. 17D-17F illustrate intraexonic junction between APP exon 3 and exon 16 (IEJ 3/16) on SAD neuronal nuclei.
Figure 17E:
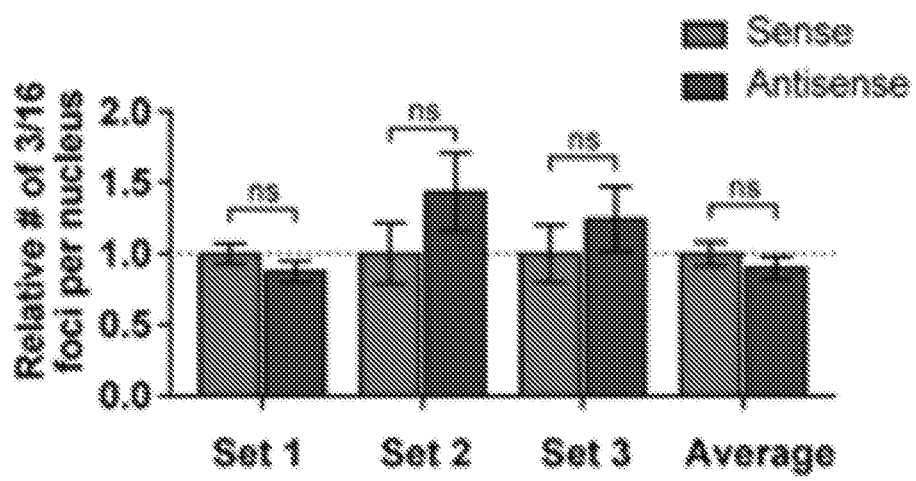
Figure 17F:
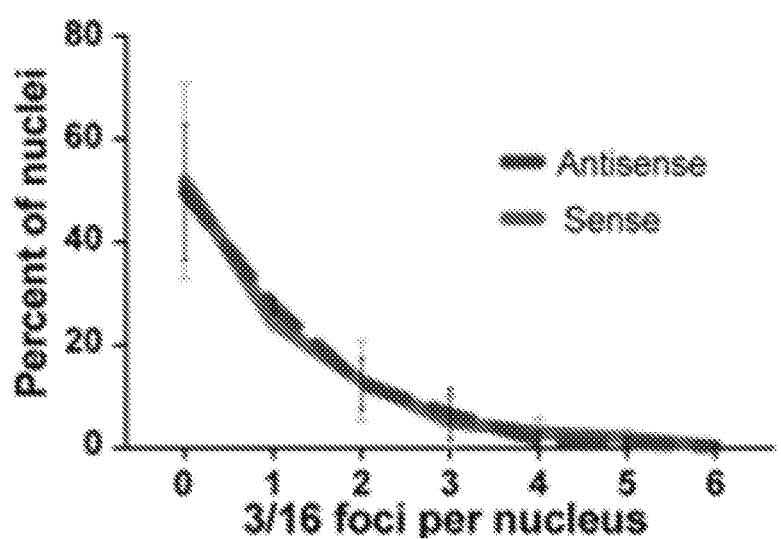
Figure 17G:
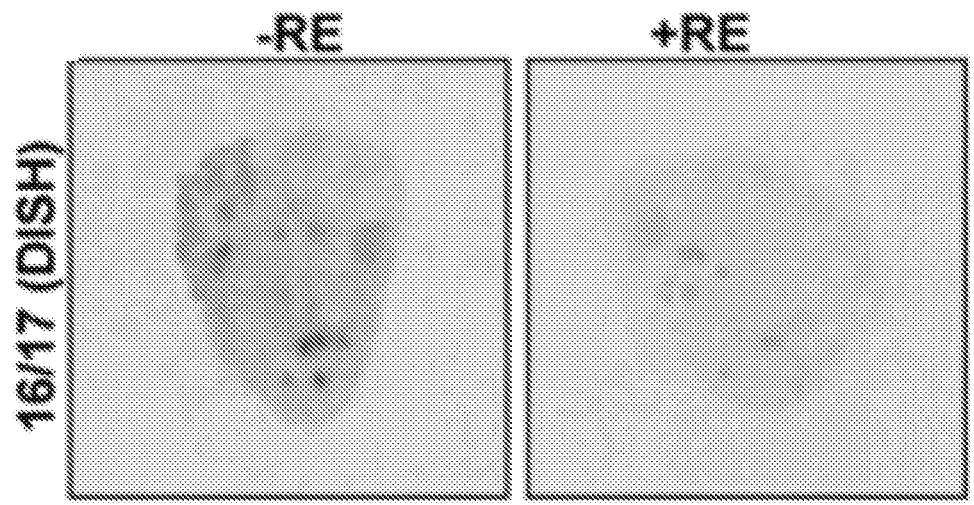
FIGS. 17G-17J illustrate restriction enzyme (RE) digestion. RE digestion was performed using MluCI (FIGS. 17G-17H) and PstI+MsII (FIGS. 17I-17J) to eliminate Ex 16/17 and IEJ 3/16 target sequences, respectively.
Figure 17H:
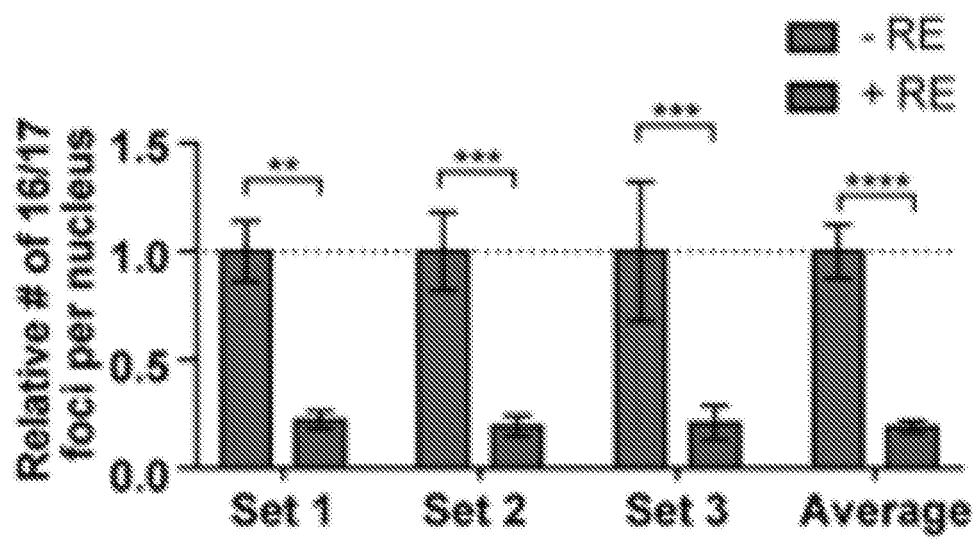
Figure 17I:
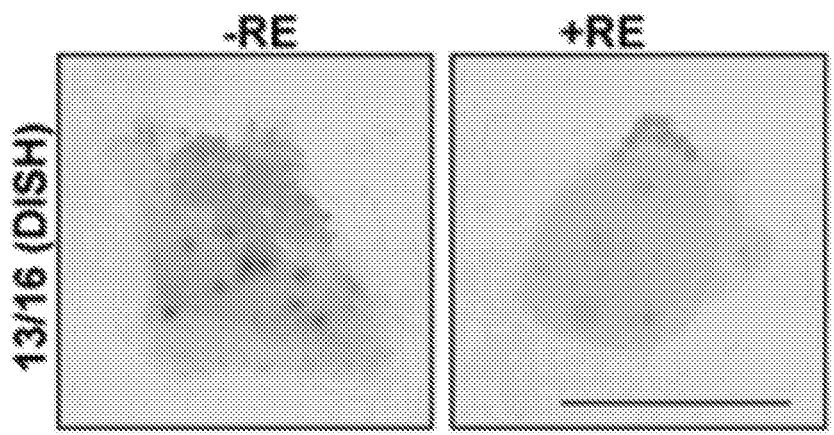
Figure 17J:
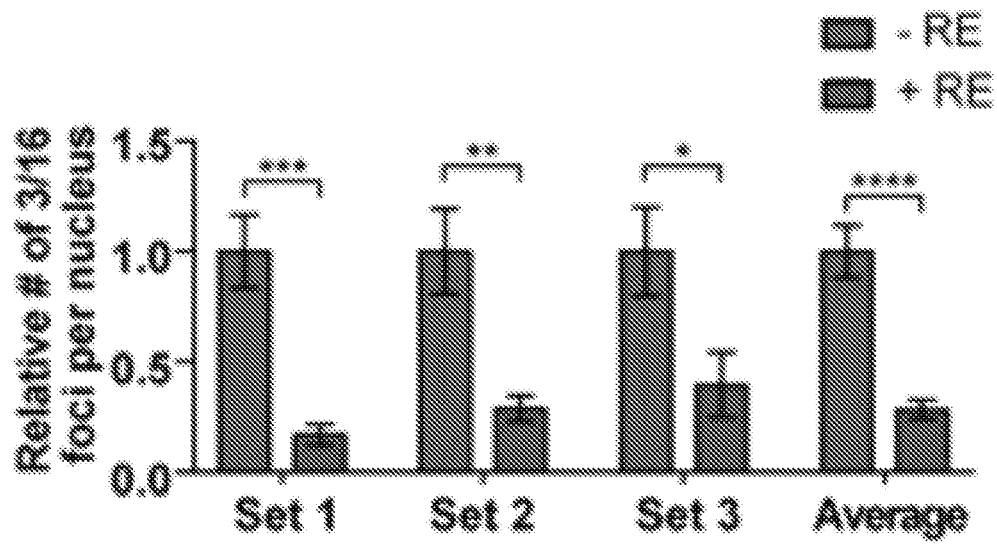
Figure 17K:
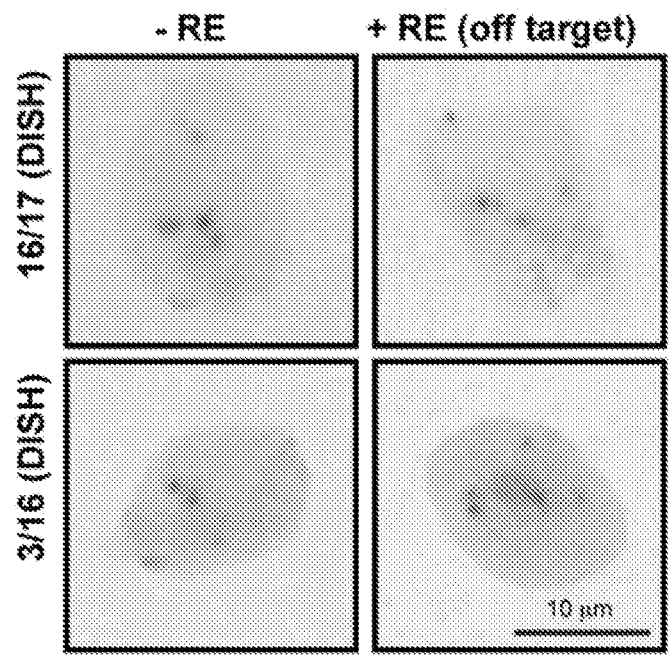
FIG. 17K illustrates off-target restriction enzyme with XbaI showing digestion did not affect DISH3/16 and DISH16/17 signals.
Figure 17L:
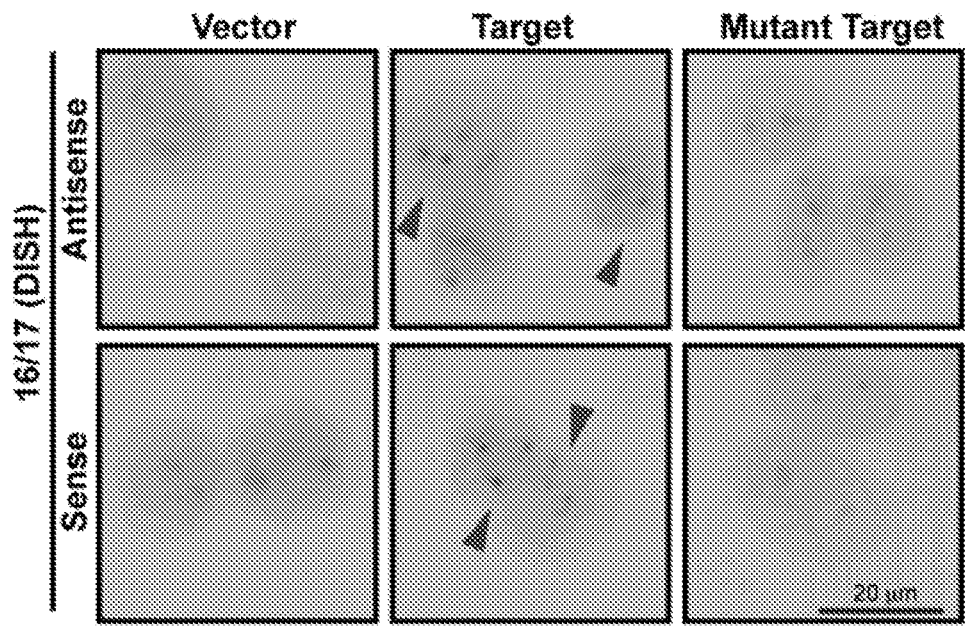
FIGS. 17L-17M illustrate synthetic DNA containing 3/16 or 16/17 target sequences (target), or wild type human genomic APP sequences lacking IEJs and exon::exon junctions (mutant target) that were introduced by retroviral transduction in NIH-3T3 cells. DISH3/16 and DISH16/17 signals from both sense and antisense probes were only detected in target infected cells.
Figure 17M:
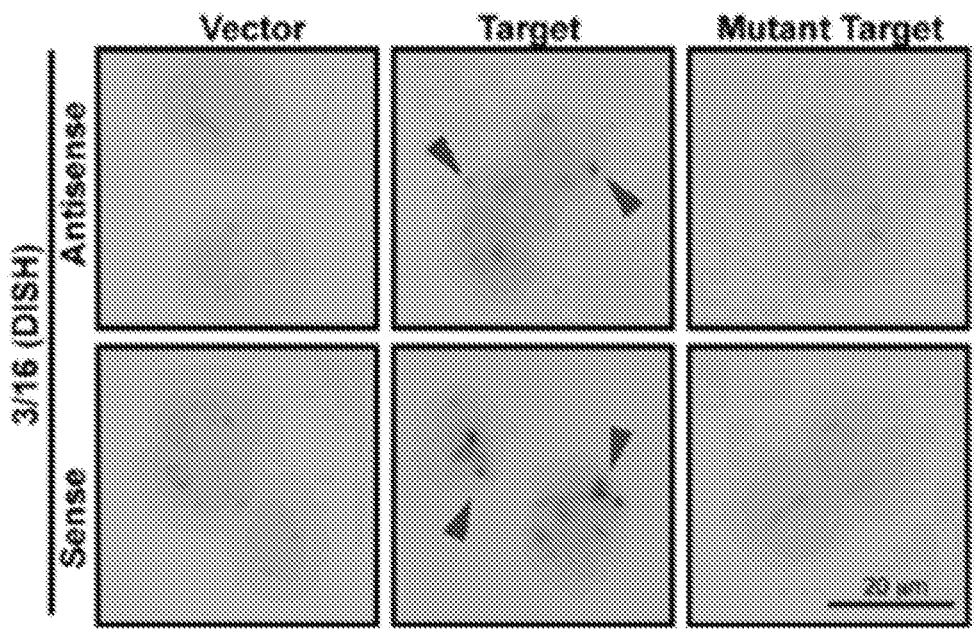
Figure 17N:
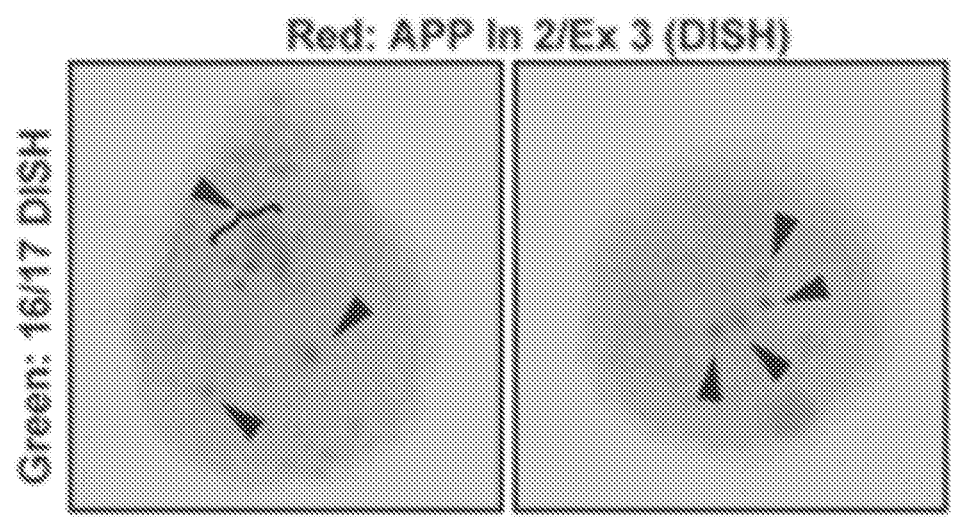
FIG. 17N illustrates dual DISH with Intron2/Exon3 (Red) genomic locus and 16/17 (green).

Briefly, sample preparation and hybridization protocols for RNA-ISH were used according to manufacturer's instruction (ACD, Newark, Calif.) to recognize genomic DNA sequences. Probes used passed multiple specificity requirements involving both positive and negative controls (FIGS. 17A-17F and Table 7). Two jgISH probes were used: one that recognized gencDNAs via the exon 16::exon 17 junction (Ex 16/17), which spans the Ab coding region of APP; and one that recognized IEJ formed between exons 3 and 16 (IEJ 3/16), representing one APP variant. All bound probes were enzymatically visualized, appearing as red dots (as indicated by the arrows) of varied diameter. Both sense and anti-sense jgISH probes produced similar results in RNase treated SAD neuronal nuclei (FIGS. 17A-17F). By comparison, RNA signals were only detected using the anti-sense probes (FIG. 15L); therefore sense probes were exclusively used for genomic DNA detection. The jgISH sense probe signals were eliminated by specific restriction enzyme digestion of genomic DNA that eliminated the sequence recognition site (FIGS. 17G-17K). In addition, no DISH signal was detected on cells infected with retroviruses containing wild type human genomic APP sequences lacking the IEJ and exon::exon junction (FIG. 17L-17M). Use of dual DISH on APP intron2::exon3 wild type genomic sequence, with DISH3/16 or DISH16/17, demonstrated that APP gencDNAs did not co-localize with the wild type APP locus (FIG. 17N). Taken together, the DISH protocol detected specific APP gencDNA junctions without polymerase dependent template amplification.

TABLE 7

List of jgISH positive control, negative control, and experimental probes

| Junction | Target | Sample | Type | Probes |
|---|---|---|---|---|
| Ex 16/17 | DNA | Human nuclei + RNase | Exp | Sense |
| | | | Exp | Anti-sense |
| | | Human nuclei + RNase + restriction enzyme (MluCI) | Neg | Sense |
| | | Human nuclei + RNase + off-target restriction enzyme (XbaI) | Pos | Sense |
| | | Synthetic target | Pos | Sense |
| | | | Pos | Anti-sense |
| | | Synthetic mutant target | Neg | Sense |
| | | | Neg | Anti-sense |
| IEJ 3/16 | DNA | Synthetic target concatamer | Pos | Sense |
| | | WT mouse nuclei + RNase | Neg | Sense |
| | | J20 mouse nuclei + RNase | Exp | Sense |
| | | Human nuclei + RNase | Exp | Sense |
| | | | Exp | Anti-sense |
| | | Human nuclei + RNase + restriction enzyme (PSTI & MsII) | Neg | Sense |
| | | Human nuclei + RNase + off-target restriction enzyme (XbaI) | Pos | Sense |
| | | Synthetic target | Pos | Sense |
| | | | Pos | Anti-sense |
| | | Synthetic mutant target | Neg | Sense |
| | | | Neg | Anti-sense |
| | | WT mouse nuclei + RNase | Exp | Sense |
| | | J20 mouse nuclei + RNase | Exp | Sense |
| | RNA | SAD tissue | Neg | Sense |
| | | | Exp | Anti-sense |
| | | | Neg | DapB |
| In2/Ex3 | DNA | Human nuclei + RNase | Exp | Sense |

Exp = Experimental,
Neg = negative control,
Pos = positive control

Figure 17O:
FIG. 17O illustrates Agilent SureSelect Custom DNA pull down targeting entire genomic locus of APP and hybridization enrichment producing an unbiased depth across the full genomic locus. Exons and introns are shown on two scales.
Figure 17P:
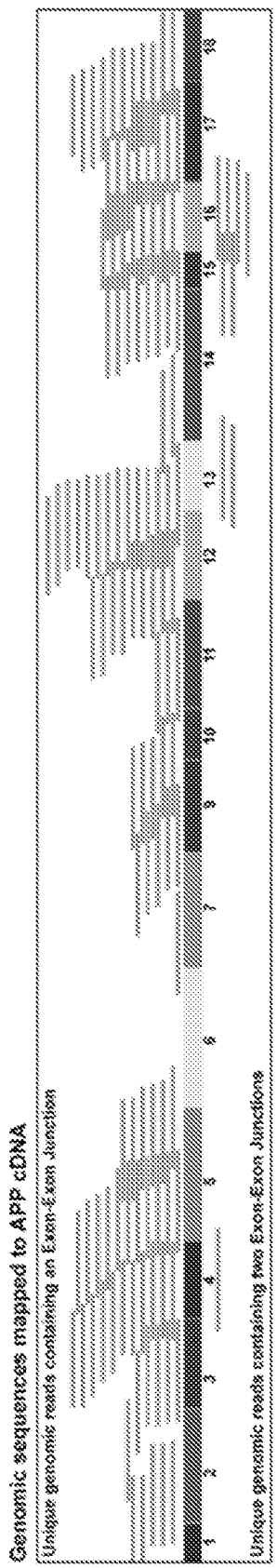
FIG. 17P illustrates a schematic of APP cDNA and genomic exon-exon junctions identified by Agilent SureSelect enrichment of the APP locus followed by short-read Illumina sequencing. Top: Reads spanning 1 exon::exon junction; Bottom: Reads spanning two Exon::Exon junctions.

A stand-alone methodology (FIG. 16A) identified APP gencDNAs without primary PCR amplification by using a custom Agilent SureSelect targeted DNA pull-down (Agilent Technologies, Santa Clara, Calif.) with unbiased coverage (FIG. 17O) across the entire APP genomic locus. This completely independent approach interrogated 40,000 SAD neuronal nuclei and identified all expected exon::exon gencDNA junctions (FIG. 17P).

This example shows that the jgISH protocol detected specific genomic junctions without polymerase dependent template amplification. Moreover, use of Ex16/17 and IEJ 3/16 probes identified the mosaic presence of these gencDNA sequences in neuronal nuclei.

Figure 18A:
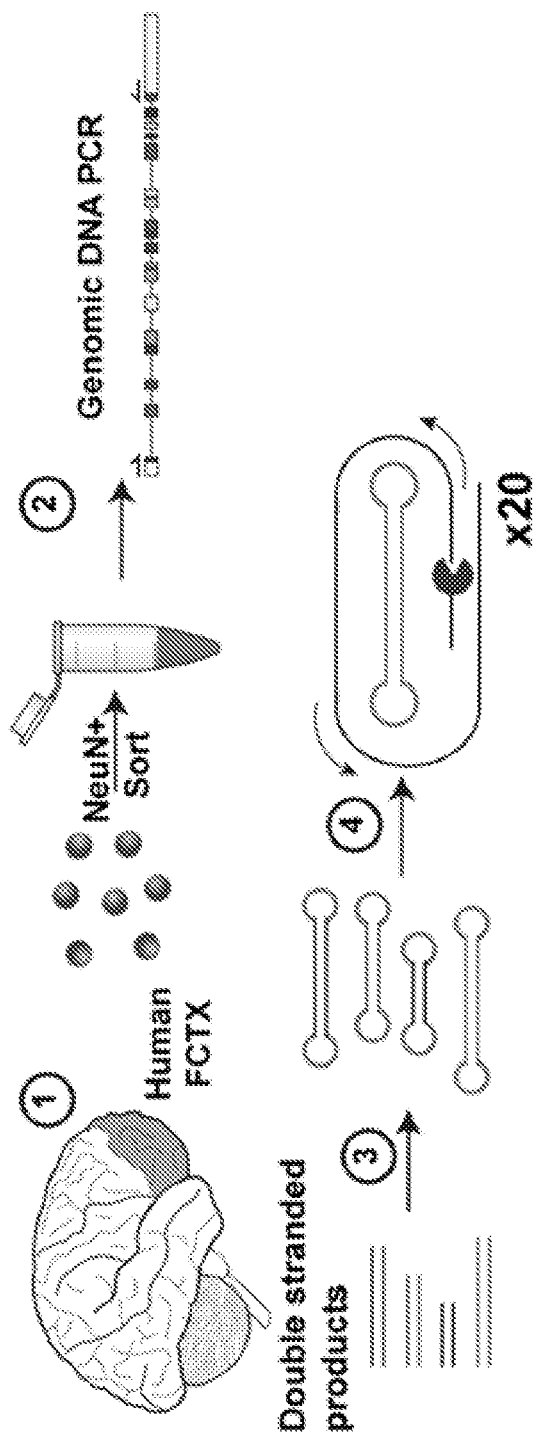
FIG. 18A illustrates a schema of non-classical gencDNAs variants of APP identified by SMRT sequencing from SAD brains. (1) Neuronal nuclei from SAD prefrontal cortex (FCTX) were sorted and used for (2) genomic DNA PCR. Multiple reactions were pooled for (3) library preparation to enable (4) high fidelity sequencing (SMRT 20×CCS calling).
Figure 18B:
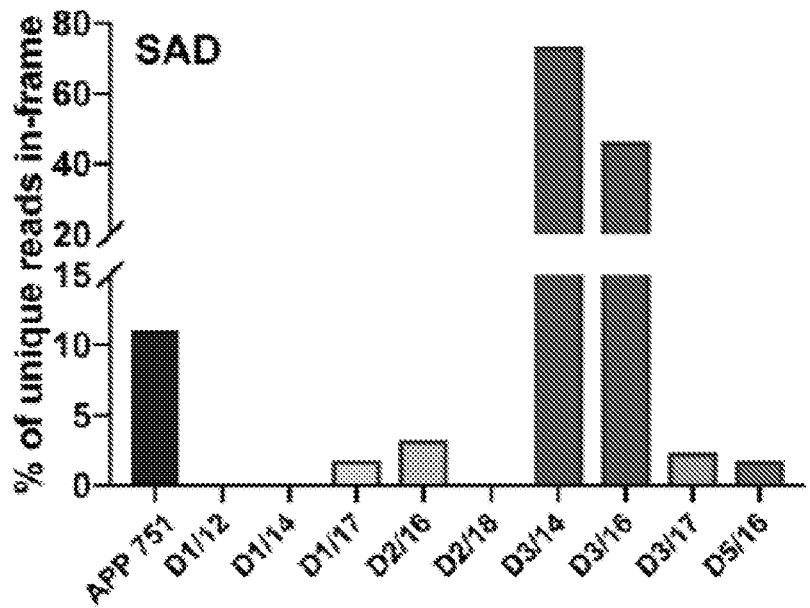
FIG. 18B illustrates a graph of percentage of in-frame reads from SAD brains.
Figure 18C:
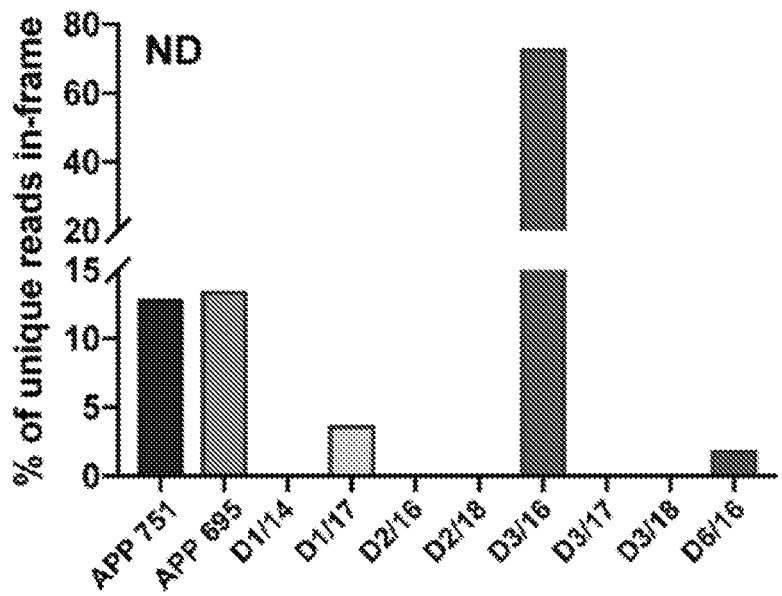
FIG. 18C illustrates a graph of percentage of in-frame reads from non-diseased brains.
Figure 18D:
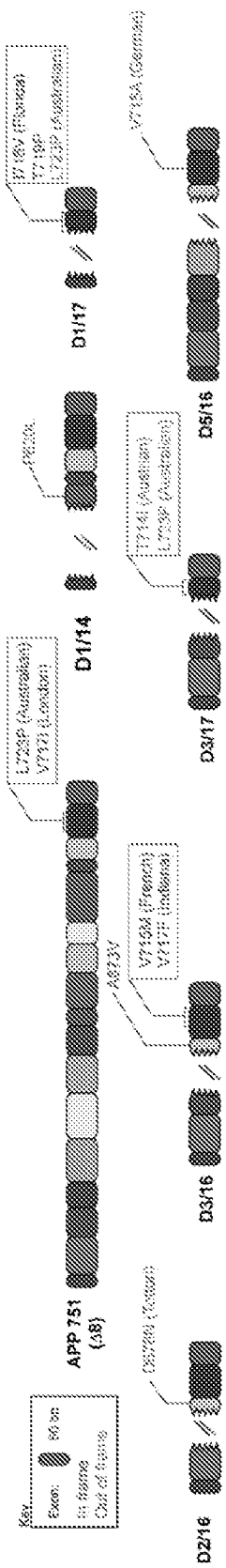
FIG. 18D illustrates a schematic of 11 different familial AD mutations identified in 6 APP gencDNAs, and APP 751. In-frame (red) and out-of-frame (grey) mutations are indicated based on the known APP reading frame analysis.

Example 16. Thousands of Distinct APP GencDNAs from Populations of Neuronal Nuclei Non-classical gencDNA variants of APP were analyzed using multiple independent reactions on neuronal populations from brains (FIG. 18A), utilizing a DNA polymerase with 100x higher fidelity compared to native Taq (Platinum SuperFi DNA Polymerase, Invitrogen). The resulting samples were pooled for library preparation to enable SMRT CCS of single DNA molecules. SMRT libraries yielded high-certainty consensus calling (20 CCS subreads with 99.9999% accuracy, median Phred score of 93). 6,299 unique sequences (10.0% in frame) including 45 different IEJs were identified in neuronal nuclei from SAD brains (FIG. 18B), and 1,084 unique sequences (12.1% in frame) including 20 IEJs were found in neuronal nuclei from non-diseased brain (FIG. 18C). Mosaic SNVs were far more prevalent throughout SAD gencDNAs and included 11 known SNVs previously published as pathogenic FAD mutations (FIG. 18D), including the well-known Indiana mutation; no known pathogenic FAD SNVs were identified in non-diseased brains (data not shown).

Example 17. GencDNA Production Increases with Age in J20 Neurons

Figure 19A:
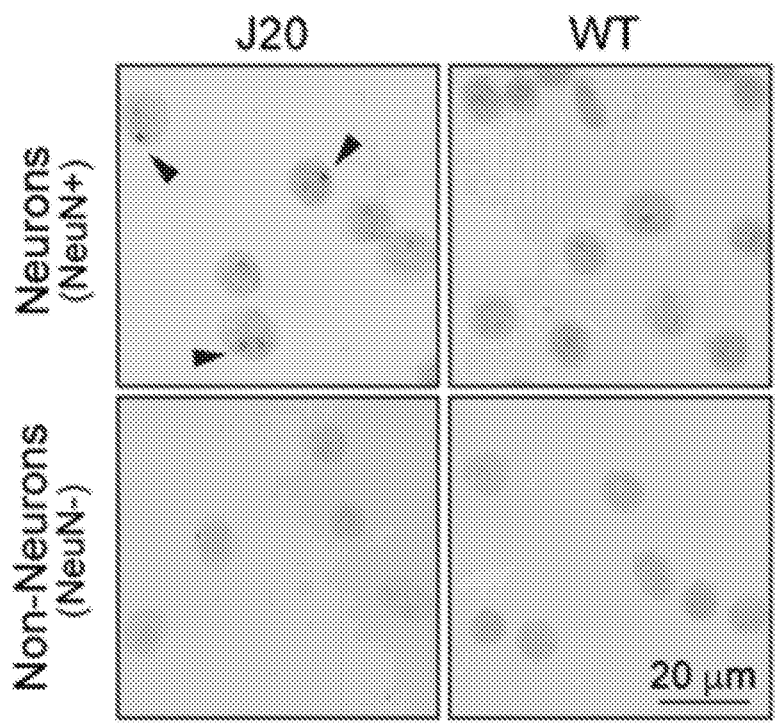
FIG. 19A illustrates images of DISH3/16 of nuclei isolated from the cortex of an AD mouse model (J20 transgenic, with neuron specific expression of human APP cDNA containing Swedish and Indiana mutations) versus WT littermates.
Figure 19B:
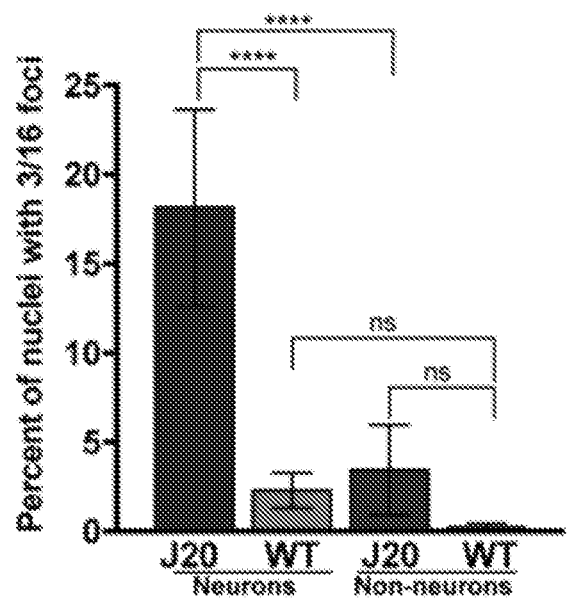
FIG. 19B illustrates a graph of percent of nuclei with one or more foci was statistically increased in J20 neurons (calculated using non-parametric Kruskal-Wallis test with Dunn's correction for multiple comparisons).
Figure 19C:
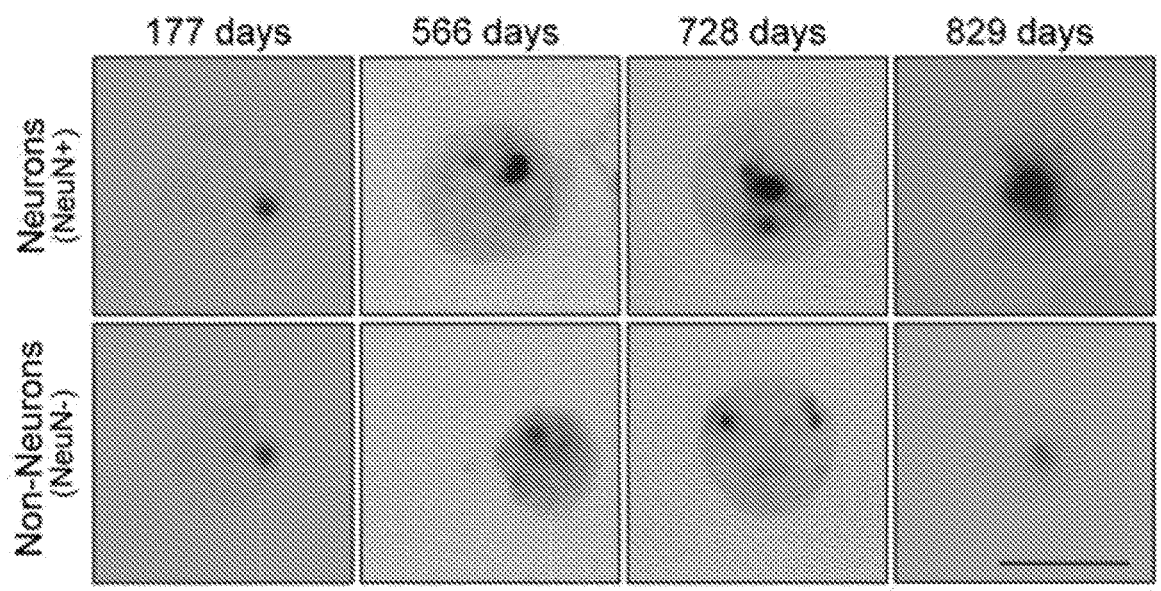
FIGS. 19C-19D illustrate DISH16/17 foci area increased with age in J20 mice.
Figure 19D:
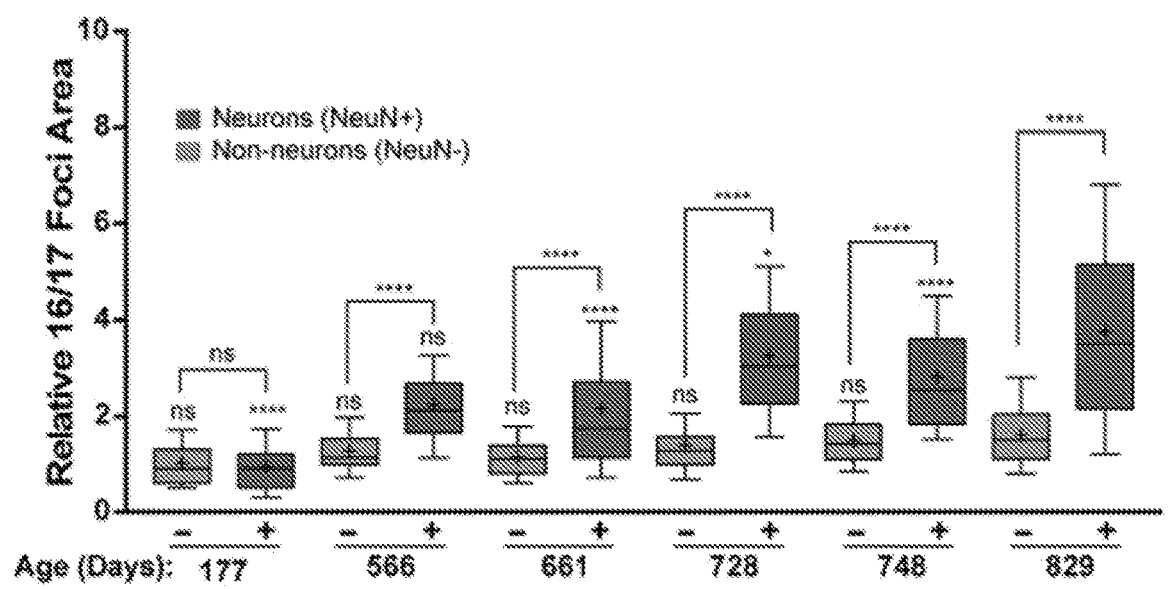
Figure 19E:
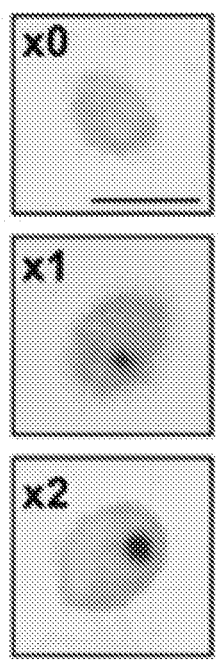
FIGS. 19E-19G illustrates data of synthetic DNA targets containing the Ex 16/17 junction sequence introduced by retroviral transduction in NIH-3T3 cells, and the target sequence (provirus) identified by DISH16/17. A concatamer (×2) showed increased foci size, represented as a cumulative distribution (FIG. 19F) and average foci area (FIG. 19G). Statistical significance was calculated using non-parametric Kruskal-Wallis test with Dunn's correction for multiple comparisons $****p<0.0001$. Error bars are ±SEM. Scale bars are 10 µm unless otherwise noted.
Figure 19F:
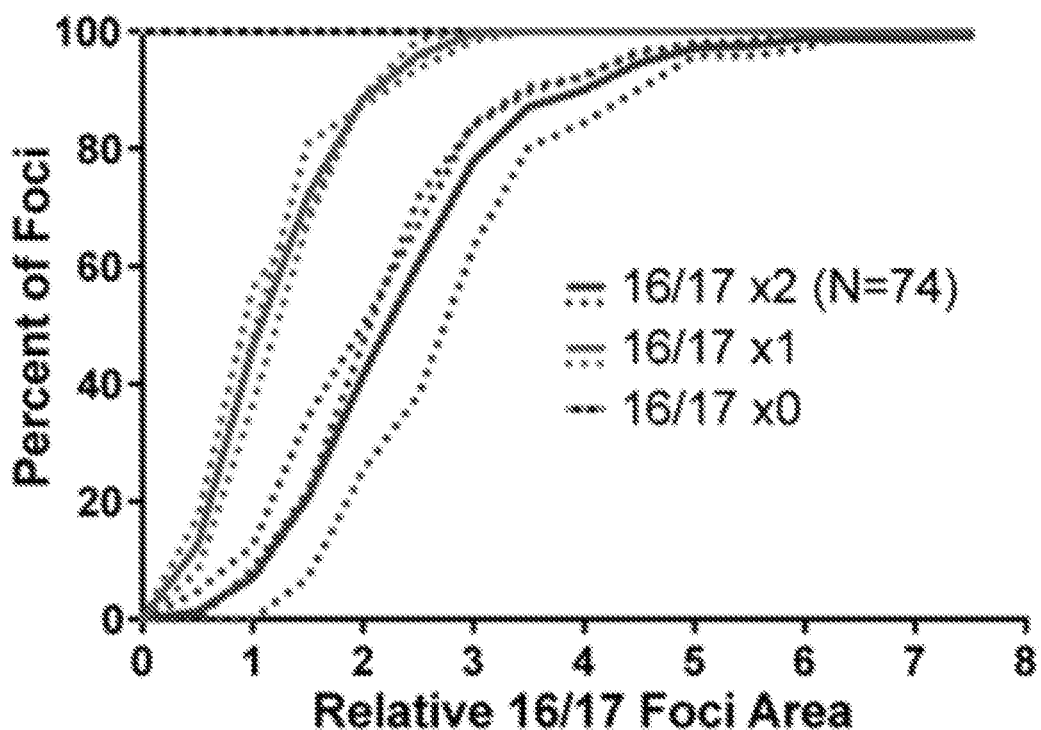
Figure 19G:
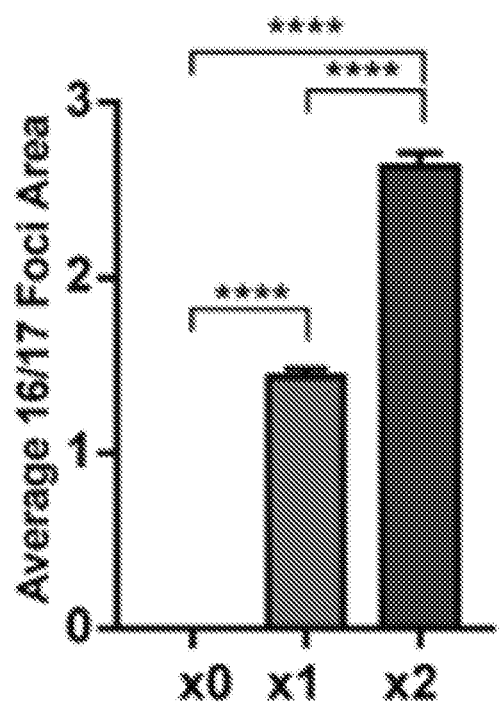

GencDNA production was tested in a mouse model for Alzheimer's disease. Experiments in wild type mice demonstrated that DISH was specific for human APP and did not recognize the endogenous mouse locus (FIG. 19A). DISH3/16 identified enriched signals in J20 neuronal nuclei, contrasting with low levels in non-neuronal nuclei from the same animals (FIGS. 19A-19B). The more prevalent gencDNA sequence recognized by DISH16/17 was also highly enriched in neurons and remarkably, demonstrated an age-dependent increase in gencDNA foci area over a 2.3-year period, a pattern of change that did not occur in non-neuronal nuclei (FIGS. 19C-19D). Use of retroviral provirus containing 0, 1, or 2 copies of the DISH16/17 target sequence, demonstrates that foci area is semi-quantitative and reflects DNA copy numbers (FIGS. 19E-19G). The increase in foci area selectively within J20 neurons occurs during postnatal life after cerebral cortical neurogenesis has ceased. These results support neuronal gene transcription in generating gencDNAs.

Example 18. Reverse Transcriptase Inhibitors Inhibit Generation of GencDNAs

Figure 20A:
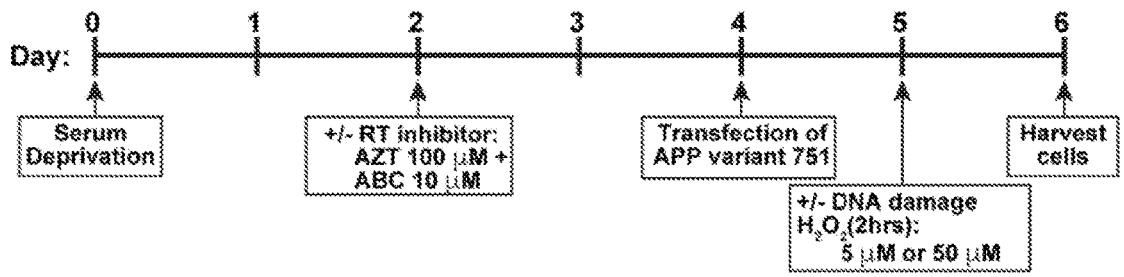
FIG. 20A illustrates a schematic of cell culture experiments: (1) Timeline of CHO cell experiments. DNA was extracted from transfected cells and used for (2) genomic DNA PCR (3), Cloning and Sanger sequencing of products, and (4) identification of variants.
Figure 20A:
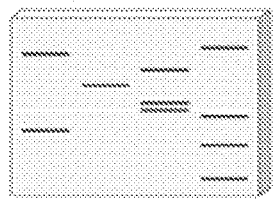
Figure 20A:
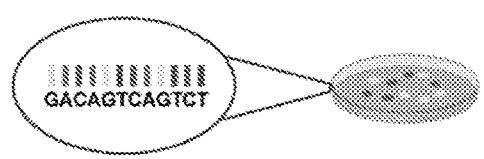
Figure 20A:

The method is graphically represented in FIG. 20A. CHO cells were serum-deprived for 2 days, followed by addition of reverse transcriptase (RT) inhibitors azidothymidine (AZT, 100 μM) and abacavir (ABC, 10 μM) (Tocris, Minneapolis, Minn.) until the end of the experiment. Medium was changed daily with fresh RT inhibitors. Cells were transfected with APP 751 by GenJet (SignaGen Laboratories, Gaithersburg, Md.) on day 3, then on day 4 cells were treated with 0 μM, 5 μM, or 50 μM of hydrogen peroxide (Fisher Scientific) for 2 hrs. After 1 day, cells were collected and genomic DNA was extracted for PCR analysis.

In Vitro Reverse Transcriptase Activity Assay

In one example, lysates were prepared in reverse transcriptase disruption buffer and contained Complete™, EDTA-free Protease Inhibitor Cocktail (Sigma-Aldrich, St. Louis, Mo.) and PhosSTOP™ phosphatase inhibitors (Sigma-Aldrich, St. Louis, Mo.). One microgram of extract was used in the reverse transcription step of the assay. Reverse transcription was carried out at 37° C. for 45 min, followed by 15 min at 70° C. The RT product of this first step was assayed in triplicate by quantitative PCR. Levels of reverse transcription activity were determined by the Delta Cq method, compared to the activity in negative controls (water and no nucleotides) that were given Cq scores of 40. $1 \times 10^5$ picounits of SuperScript™ II Reverse Transcriptase (ThermoFisher Scientific) were used as a positive control for the assay. Lysates for heat inactivation experiments were incubated for 15 min at 70° C. prior to the reverse transcription step. For inhibitor experiments, lysates were incubated with inhibitor in the presence of all the components of the reaction except for dNTPs. After 10 min at room temperature, dNTPs were added and the reaction was incubated at 37° C. as above. AZT-TP was purchased from TriLink Biotechnologies (San Diego, Calif.).

In another example, the in vitro reverse transcriptase activity assay was conducted with reagents and protocol as shown in Tables 8-11.

TABLE 8

| | Reagent preparation |
|---|---|
| 10x modified RT buffer | 1 ml 10x RT buffer (Invitrogen) |
| | 50 μl 1M MgCl2 |
| | 10 μl 10% Nonident P-40 |
| Annealed Primer A and MS2 RNA | 32.5 μl 10 uM Primer A |
| | 37.5 μl MS2 RNA (0.8 mg/ml) |
| | * Heat to 65 C. in heatblock for 5 minutes, then plunge on ice |
| qPCR Primer/Probe mix | 25 μl 100 uM Primer A |
| | 25 μl 100 uM Primer B |
| | 7.5 μl 100 uM Probe |
| | 567.5 μl Nuclease Free Water |
| Reverse Transcription Lysis Buffer (RTLB) | 20 mM Tris pH 7.8 Made into a 2x stock |
| | 50 mM KCl |
| | 1 mM MgCl2 |
| | 1 mM EGTA |
| | 10% glycerol |
| | 0.5% Detergent (TX-100) Added fresh/ml |
| | 1x Complete Protease Inhibitors (Roche) |
| | 1x Stop It Phosphatase Inhibitors (Roche) |
| | 10 mM DTT |
| | For 1 ml RTLB |
| | 500 μl 2x stock |
| | 10 μl 1M DTT |
| | 100 μl 10x Complete Protease Inhibitors (Roche) |
| | 100 μl 10x Stop It Phosphatase Inhibitors (Roche) |
| | 50 μl 10% TX-100 |
| | 240 μl Nuclease Free Water |

TABLE 9

| | Primers |
|---|---|
| Primer A | 5' - GCC TTA GCA GTG CCC TGT CT - 3' |
| Primer B | 5' - AAC ATG CTC GAG GGC TTT A - 3' |
| Primer C | 5' - CTT GAA CCC ACT AGG TAT AGT G |

TABLE 10

| | Protocol |
|---|---|
| 1) Reverse Transcription Reaction | 2.5 μl 10x modified RT buffer |
| | 2 μl 2.5 mM dNTPs |
| | 0.5 μl 100 mM DTT |
| | 0.7 μl Annealed Primer A/MS2 RNA |
| | 0.2 μl RNaseOUT |
| | 1 μl 1 mg/ml cell/brain lysate |
| | 18.1 μl Nuclease Free Water |
| | *** All procedures done in biological cabinet |
| | *** Controls |
| | Positive Controls: CHO Cell lysate, HIV RT, MMLV (Superscript II) |
| | Negative Controls: Denatured CHO lysate, RTLB |
| | Thermocycler protocol: 45 minutes at 37 C. → 15 minutes at 70 C. |
| 2) Pre-Amplification | 7.5 μl 10x PCR Buffer -MgCl2 |
| | 2.25 μl 50 mM MgCl2 |
| | 1.5 μl 10 mM dNTPs |
| | 1.5 μl Primer A |
| | 1.5 μl Primer D |
| | 0.3 μl Platinum Taq |

TABLE 10-continued

| | Protocol |
|---|---|
| | 0.7 µl 2 mg/ml RNase A<br>34.75 µl Nuclease Free Water<br>Thermocycler protocol: 5 minutes at 95 C. →<br>(15 seconds at 95 C. → 15 seconds at 62 C. →<br>30 seconds at 72 C.) × 20 → 5 minutes at<br>72 C. → Hold at 4 C. |
| 3) qPCR | 10 µl cDNA<br>3.5 µl 10x PCR Buffer -MgCl2<br>1.05 µl 50 mM MgCl2<br>0.7 µl 10 mM dNTPs<br>2.2 µl Primer/Probe mix<br>0.35 µl 2 mg/ml RNase A<br>0.175 µl Platinum Taq<br>17.025 µl Nuclease Free Water<br>** Triplicate samples of 10 µl in 384-well Taqman plate.<br>Mix samples and aliquot with multichannel<br>Spin down at 4,000 rpm for 2-3 minutes<br>CFX protocol<br>Background: cycles 3-10 30 minutes at 37 C.<br>2 minutes at 95 C. → (15 seconds at 95 C. →<br>45 seconds at 56 C.) |

TABLE 11

| Analysis |
|---|
| Background: cycles 3-10 |
| Background subtracted |
| Manual threshold 200 RFU |
| Delta Cq method to compare RT activity |
| 1) Delta Cq |
| Cq-average(Negative Control Cq) |
| 2) Relative RT |
| 2^(-DeltaCq) |
| *** No signal = Cq 50 |

Figure 20B:
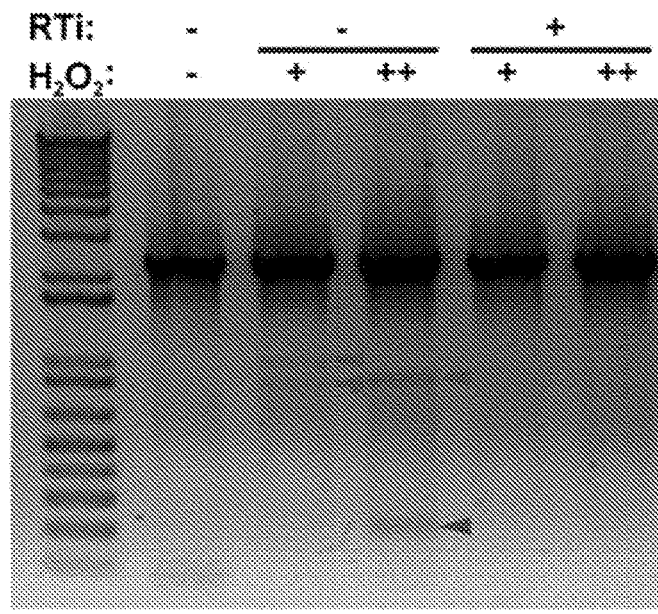
FIG. 20B illustrates a gel electrophoresis of PCR product (marked with arrowhead) indicating which induced variant bands were cloned and sequenced.
Figure 20C:
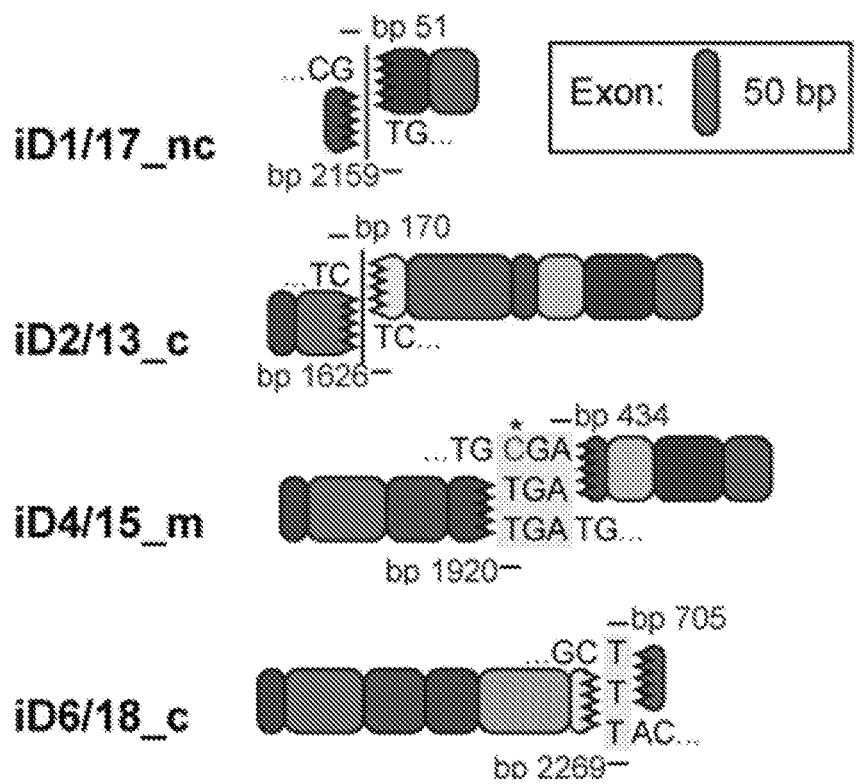
FIG. 20C illustrates a schematic of induced gencDNA variants with new IEJs.
Figure 20D:
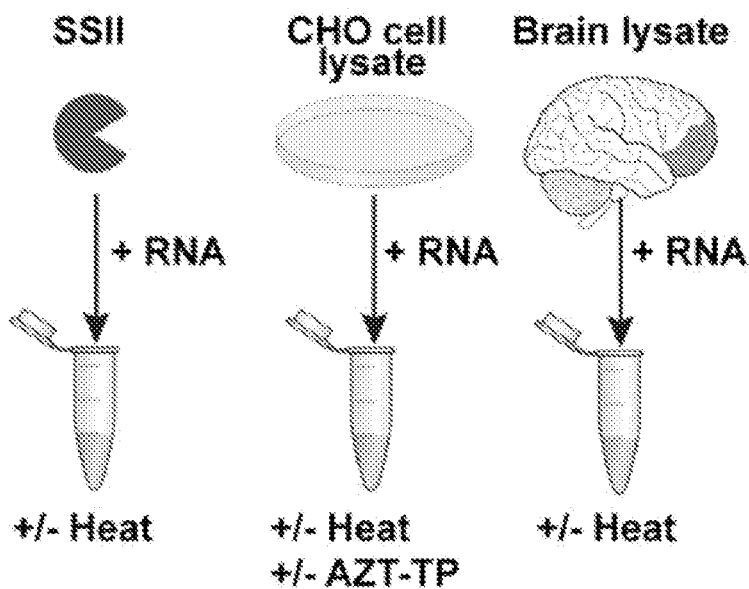
FIG. 20D illustrates a schematic of experiments where reverse transcriptase (RT) activity was analyzed in reverse transcriptase (Super Script II (SSII)) positive controls, CHO cell lysate, and human brain lysate.
Figure 20E:
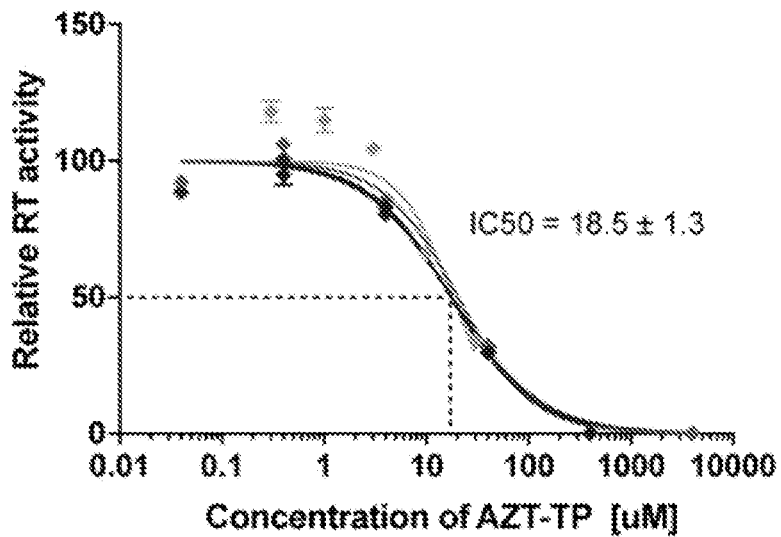
FIG. 20E illustrates a graph of four independent experiments showed decreased reverse transcriptase activity in CHO cell lysate in response to the RT inhibitor azidothymidine triphosphate (AZT-TP) with an IC50 of 18.5 uM (±1.3).
Figure 20F:
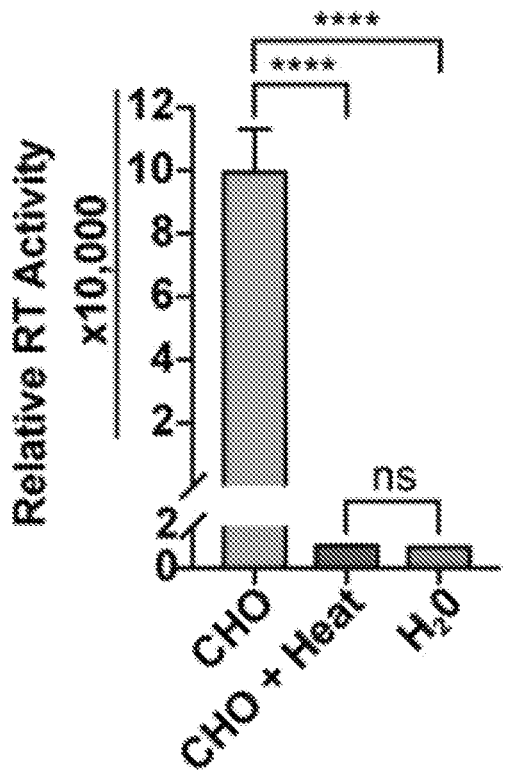
Figure 20G:
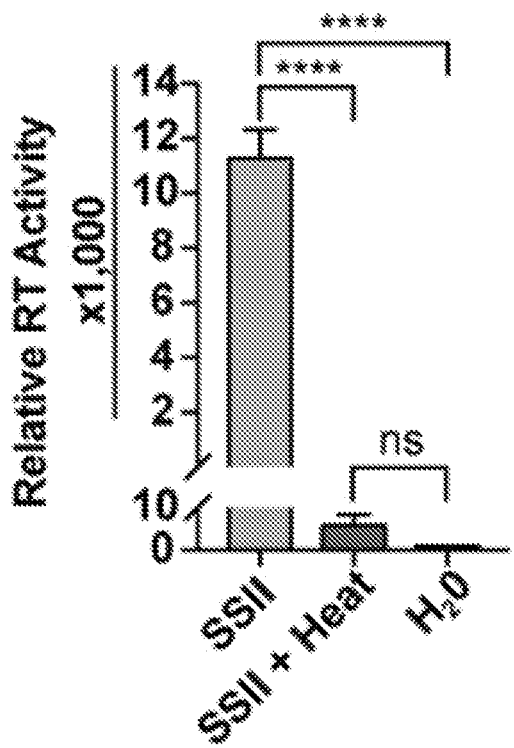
Figure 20H:
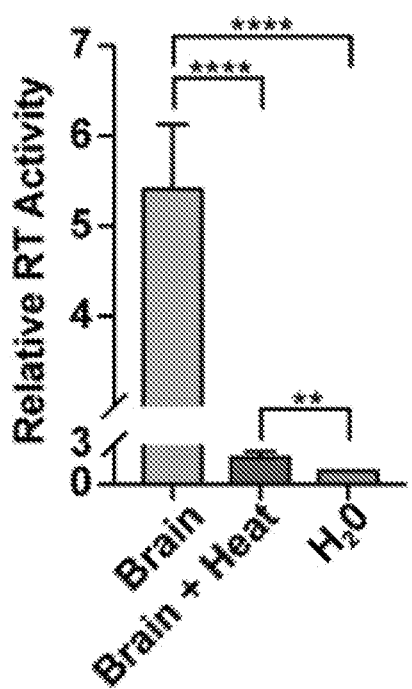
Figure 20I:
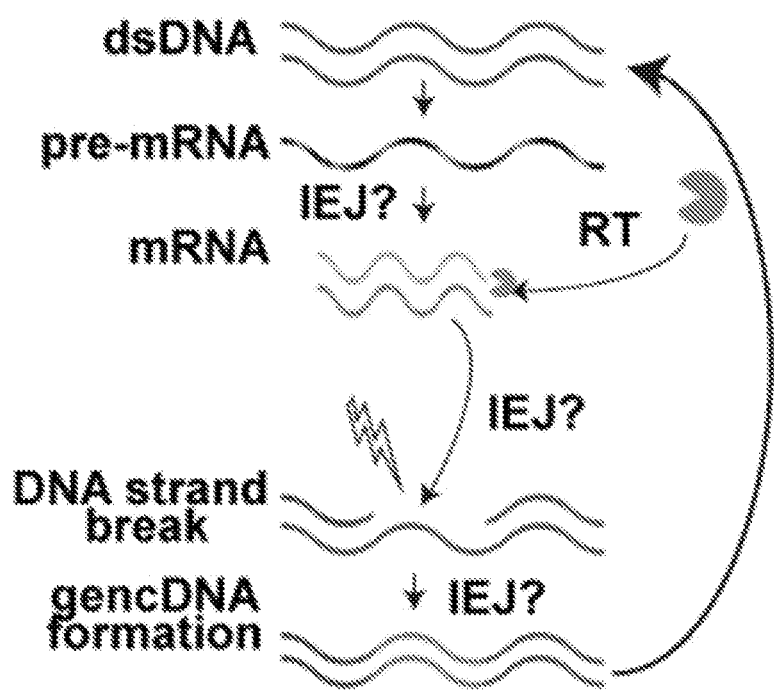
FIG. 20I illustrates a schematic of a model of reverse transcriptase activity in the formation of gencDNAs.

Introduction of DNA strand breaks by hydrogen peroxide treatment resulted in multiple bands (FIG. 20B) that upon Sanger sequencing, identified 4 new APP gencDNAs with different IEJs (FIG. 20C). In addition to DNA strand breaks, endogenous reverse transcriptase activity that was identified by in vitro assays (FIGS. 20D-20F), was also required to produce gencDNAs, based on results using the nucleoside reverse transcriptase inhibitors (NRTIs) abacavir (ABC) and azidothymidine (AZT) (FIG. 20B). Endogenous RT activity was also identified in postmortem human prefrontal cortex (FIGS. 20G-20H and FIG. 20F); further consistent with the hypothesis that gencDNAs are derived from RNAs via reverse transcription (FIG. 20I).

Figure 20J:
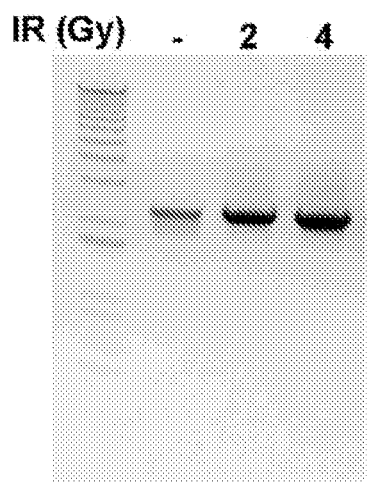
FIG. 20J illustrates a gel electrophoresis of APP non-classical variant induction by gamma-radiation and inhibition by reverse transcriptase inhibitors.

APP cDNA was transfected into CHO cells and were irradiated by gamma-radiation and recovered after 24 hours. DNA was extracted followed by PCR amplification using APP exon 1 and exon 18 primers. PCR products were then analyzed by gel electrophoresis. FIG. 20J shows APP non-classical variant induction by gamma-radiation and inhibition by reverse transcriptase inhibitors. The absence of induced bands confirms gamma irradiation doesn't induce AAP gencDNA with Intron-Exon Junctions (IEJs).

Example 19: Characterization of Increased APP GencDNA of SAD Neurons Using DISH Relationships between identified gencDNA variants and SAD were assessed by comparing them to non-diseased controls by DISH.

Two gencDNA junctions, DISH16/17 and DISH3/16, were examined in neurons from clinically and neuropathologically verified SAD brains (Table 5) and compared to neurons from non-diseased brains (FIGS. 21A-21F). The number of red foci in SAD neurons was 3 to 5 fold higher than in non-diseased neurons and ranged from 0 to a maximum of 13 in SAD nuclei. Rare foci were observed in non-neuronal (NeuN negative) nuclei from the same brains but were not statistically significant between SAD and non-diseased (FIGS. 21A-21F).

Figure 21A:
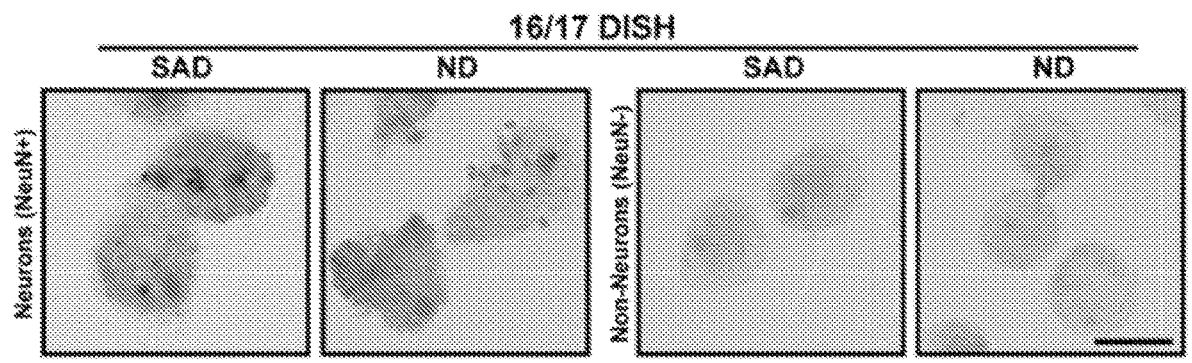
FIG. 21A illustrates DISH images (scale bars, 10 µm) of nuclei sorted from 6 SAD and 6 ND cortices analyzed by 16/17 DISH.
Figure 21B:
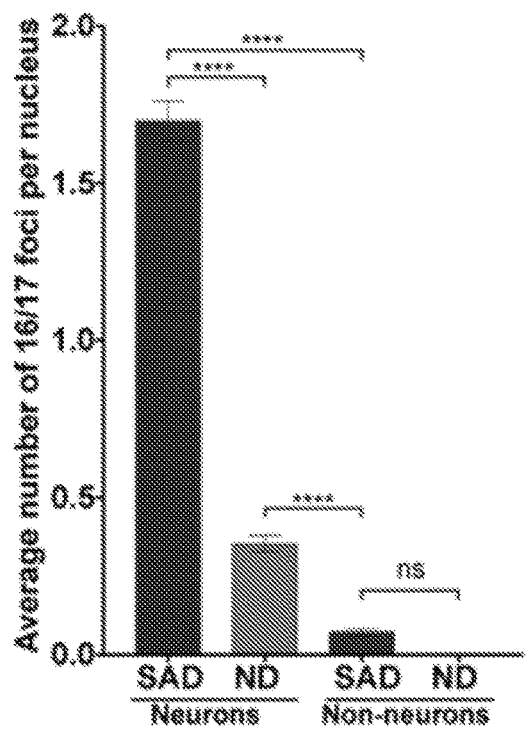
FIG. 21B illustrates a graph of average number of foci per nucleus from 6 SAD and 6 ND cortices analyzed by 16/17 DISH.
Figure 21C:
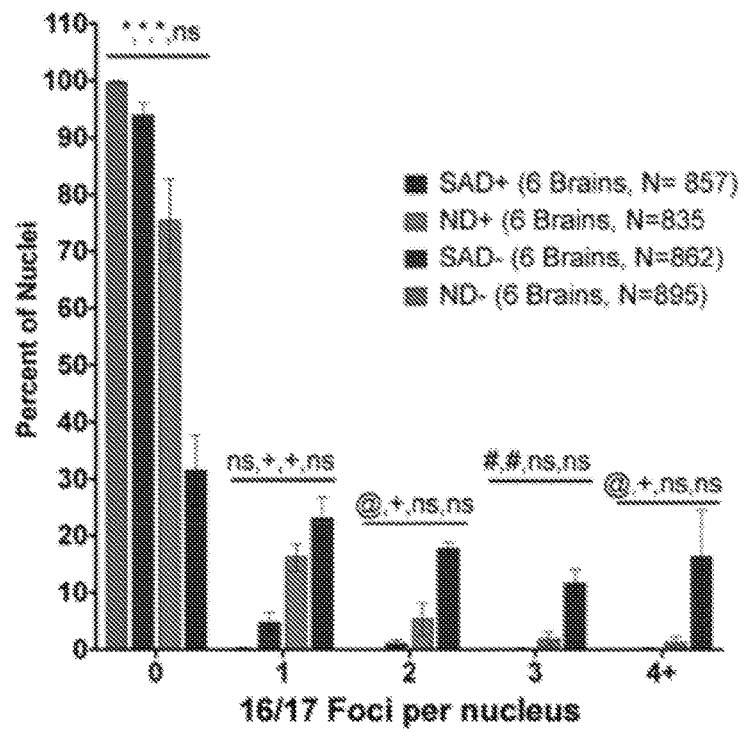
FIG. 21C illustrates a graph of frequency of distributions displaying percent of nuclei sorted from 6 SAD and 6 ND cortices analyzed by 16/17 DISH with 0, 1, 2, 3, and more than 3 (4+) foci. Statistical significance was calculated using two-way ANOVA with Fisher's LSD test for multiple comparisons (Significance is order by (SAD+vs ND+, SAD+vs SAD−, ND+vs ND−, SAD− vs ND+; #p<0.05, @ p<0.01, +p<0.001, *p<0.0001. n.s., not significant).
Figure 21D:
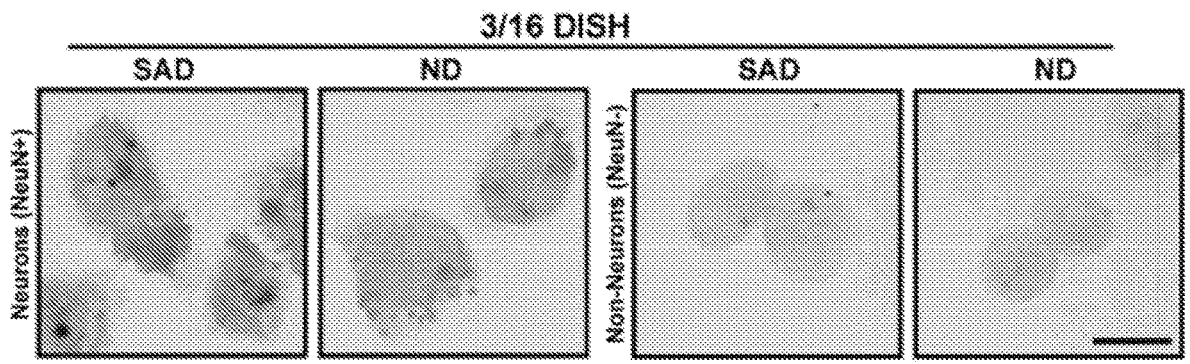
FIG. 21D illustrates DISH images (scale bars, 10 µm) of nuclei sorted from 6 SAD and 6 ND cortices analyzed by 3/16 DISH.
Figure 21E:
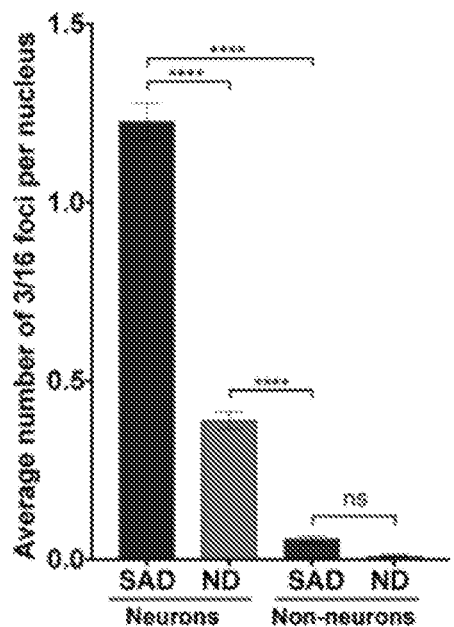
FIG. 21E illustrates a graph of average number of foci per nucleus from 6 SAD and 6 ND cortices analyzed by 3/16 DISH.
Figure 21F:
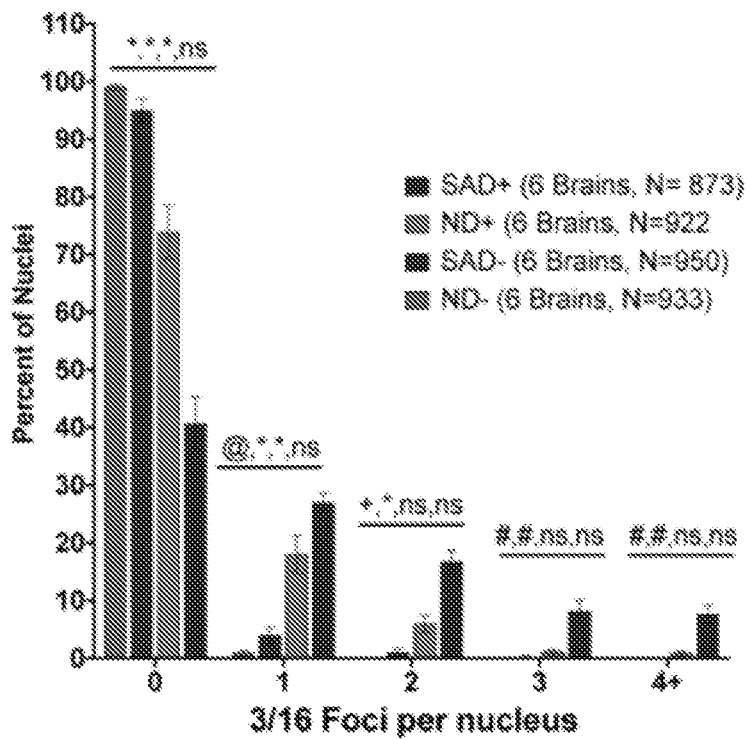
FIG. 21F illustrates a graph of frequency of distributions displaying percent of nuclei sorted from 6 SAD and 6 ND cortices analyzed by 3/16 DISH with 0, 1, 2, 3, and more than 3 (4+) foci. Statistical significance was calculated using two-way ANOVA with Fisher's LSD test for multiple comparisons (Significance is order by (SAD+vs ND+, SAD+vs SAD−, ND+vs ND−, SAD− vs ND+; #p<0.05, @ p<0.01, +p<0.001, *p<0.0001. n.s., not significant).
Figure 21G:
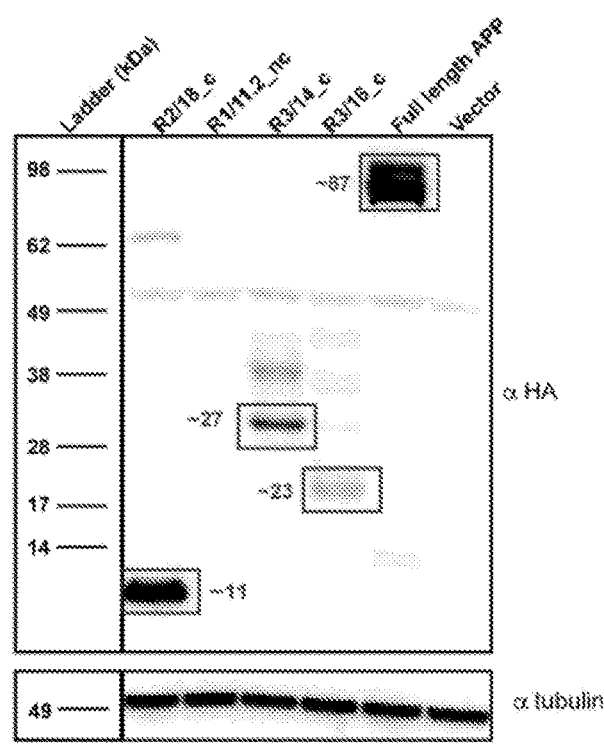
FIG. 21G illustrates a Western blot of three coding ("c") APP RNA variants, 1 non-coding ("nc") APP RNA variant, and APP 751 that were HA-tagged and transfected into HEK-293 cells.
Figure 21H:
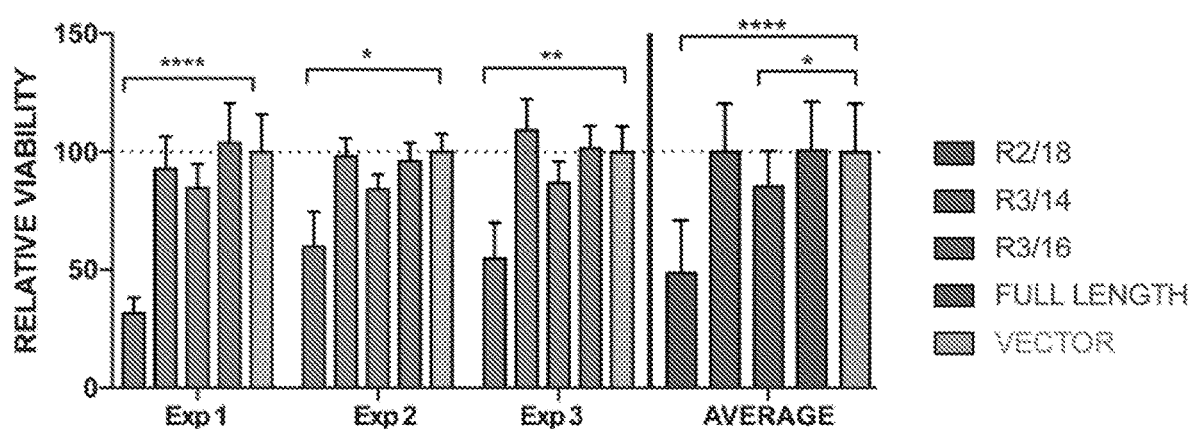
FIG. 21H illustrates a graph of three experiments (Exp 1, Exp 2, and Exp 3) and an average relative viability (y-axis) following transfection of three coding ("c") APP RNA variants, 1 non-coding ("nc") APP RNA variant, and APP 7516 in SH-SY5Y cells individually. The three experiments were analyzed in a single Two-way ANOVA with multiple comparisons and Fisher's LSD test. The combined average of the experiments was analyzed using a one-way ANOVA with multiple comparisons and Fisher's LSD test. $*p<0.05$, $ p<0.01$, $** p<0.0001$.

The cytotoxicity of protein products from 3 APP variants (R2/18_c, R3/14_c, and R3/16_c) was tested. The protein products could be translated and detected by western blot (FIG. 21G). Exposure of SH-SY5Y cells to variant proteins induced significant cell death in cell culture, depending on the variant (FIG. 21H).

Example 20: Reverse Transcriptase Inhibitors Inhibit Generation of GencDNA of a Mouse Model of Alzheimer's Disease Generation of gencDNAs is determined following treatment of reverse transcriptase inhibitors in a mouse model of Alzheimer's disease.

The J20 mouse model of Alzheimer's disease is used. The J20 transgenic mouse line expresses a mutated human APP (hAPP: K670N/M671L and V717F) under the control of the platelet-derived growth factor promoter. J20 mice and wild-type liter mate controls are administered orally either vehicle or the reverse transcriptase inhibitors azidothymidine and abacavir. J20 mice and wild-type mice at age 6-8 months are fed azidothymidine and abacavir for six weeks or vehicle and are analyzed for behavioral tests including the water maze task.

Following 6 weeks, the mice are sacrificed and biochemical and histopathological analyses are performed. Neurons are isolated and jgISH is performed on a set of samples to detect various intraexonic junctions (IEJ) including IEJ 3/16. A second of set samples is analyzed by PCR amplification using primers for APP exon 1 and exon 18 followed by gel electrophoresis.

Example 21: Treatment of Alzheimer's Disease Using Reverse Transcriptase Inhibitors Efficacy of reverse transcriptase inhibitors in inhibiting generation of gencDNAs and treating Alzheimer's disease is determined.

A total of 100 patients will be used for this study. Patient eligibility is listed in Table 12. Patients are administered the reverse transcriptase inhibitors Azidothymidine twice a day every 4 weeks for 76 weeks with an additional 4 weeks of assessments or placebo twice a day every 4 weeks for 76 weeks with an additional 4 weeks of assessments.

TABLE 12

| Patient Eligibility | |
|---|---|
| Age | 55 Years to 90 Years (Adult, Senior) |
| Sex | Male or Female |
| Inclusion Criteria | Meets National Institute of Neurological and Communicative Disorders and Stroke/Alzheimer's Disease and Related |

TABLE 12-continued

Patient Eligibility

| | |
|---|---|
| | Disorders Association (NINCDS/ADRDA) criteria for probable AD<br>Has a Modified Hachinski Ischemia Scale score of less than or equal to 4<br>Has a Mini-Mental State Examination (MMSE) score of 20 through 26 at Screening visit<br>Has a Geriatric Depression Scale score of less than or equal to 6 (on the staff-administered short form)<br>Has had a magnetic resonance imaging (MRI) or computerized tomography (CT) scan performed within the past 2 years that has confirmed no findings inconsistent with a diagnosis of AD<br>Has a florbetapir positron emission tomography (PET) scan or cerebrospinal fluid (CSF) result consistent with the presence of amyloid pathology at screening |
| Exclusion Criteria | Does not have a reliable caregiver who is in frequent contact with the participant (defined as at least 10 hours per week), will accompany the participant to the office and/or be available by telephone at designated times, and will monitor administration of prescribed medications<br>Meets National Institute of Neurological Disorders and Stroke/Association Internationale pour la Recherche et l'Enseignement en Neurosciences (NINDS/AIREN) criteria for vascular dementia<br>Has current serious or unstable illnesses including cardiovascular, hepatic, renal, gastroenterologic, respiratory, endocrinologic, neurologic (other than AD), psychiatric, immunologic, or hematologic disease and other conditions that, in the investigator's opinion, could interfere with the analyses of safety and efficacy in this study; or has a life expectancy of <2 years<br>Has had a history within the last 5 years of a serious infectious disease affecting the brain or head trauma resulting in protracted loss of consciousness<br>Has a history within the last 5 years of a primary or recurrent malignant disease with the exception of resected cutaneous squamous cell carcinoma in situ, basal cell carcinoma, cervical carcinoma in situ, or in situ prostate cancer with a normal prostate-specific antigen posttreatment<br>Has a known history of human immunodeficiency virus (HIV), clinically significant multiple or severe drug allergies, or severe posttreatment hypersensitivity reactions<br>Has received acetylcholinesterase inhibitor (AChEIs), memantine and/or other AD therapy for less than 4 months or has less than 2 months of stable therapy on these treatments<br>Has received medications that affect the central nervous system (CNS), except treatments for AD, for less than 4 weeks<br>Has a history of chronic alcohol or drug abuse/dependence within the past 5 years<br>Has a Visit 1 MRI with results showing >4 Amyloid-related Imaging Abnormality (ARIA), -hemorrhage/hemosiderin deposition (ARIA-H) or presence of ARIA-E (edema/effusions) |

After 76 weeks, the patients are analyzed for the outcome measurements listed in Table 13.

TABLE 13

Outcome Measurements

| | |
|---|---|
| Primary Outcome Measurements | Change From Baseline in Alzheimer's Disease Assessment Scale-Cognitive 14 Item Subscore (ADAS-Cog14) [Time Frame: Baseline, Week 80] |
| Secondary Outcome Measurements | Change From Baseline in Alzheimer's Disease Cooperative Study- Instrumental Activities of Daily Living (ADCS-iADL) [Time Frame: Baseline, Week 80]<br>The ADCS-ADL is a 23-item inventory developed as a rater-administered questionnaire answered by the participant's caregiver. The ADCS-ADL measures both basic and instrumental activities of daily living by participants. The total score ranges from 0 to 78, with lower scores indicating greater disease severity. LS Mean value is controlled for baseline value, baseline age, pooled investigator, treatment and visit. |

TABLE 13-continued

| Outcome Measurements |
|---|

Change From Baseline in Alzheimer's Disease Assessment Scale-Cognitive 11 Item Subscore (ADAS-Cog11) [Time Frame: Baseline, Week 80]
The cognitive subscale of ADAS (ADAS Cog11) consists of 11 items assessing areas of function most typically impaired in Alzheimer's disease (AD): orientation, verbal memory, language, and praxis. The scale ranges from 0 to 70, with higher scores indicating greater disease severity. LS Mean value is controlled for baseline value, baseline age, pooled investigator, treatment and visit.
Change From Baseline in Mini-Mental State Examination (MMSE) [Time Frame: Baseline, Week 80]
MMSE is a brief screening instrument used to assess cognitive function (orientation, memory, attention, ability to name objects, follow verbal/written commands, write a sentence, and copy figures) in elderly participants. Total score ranges from 0 to 30; lower score indicates greater disease severity. LS Mean value is controlled for baseline value, baseline age, pooled investigator, treatment and visit.
Change From Baseline in Alzheimer's Disease Cooperative Study Activities of Daily Living Inventory (ADCS-ADL) [Time Frame: Baseline, Week 80]
The ADCS-ADL is a 23-item inventory developed as a rater-administered questionnaire answered by the participant's caregiver. The ADCS-ADL measures both basic and instrumental activities of daily living by participants. The total score ranges from 0 to 78, with lower scores indicating greater disease severity. LS Mean value is controlled for baseline value, baseline age, pooled investigator, treatment and visit.
Change From Baseline in Functional Activities Questionnaire (FAQ) [Time Frame: Baseline, Week 80]
FAQ is a 10-item, caregiver-based questionnaire and is administered to the study partner who is asked to rate the participant's ability to perform a variety of activities ranging from financial management, shopping, playing games, food preparation, traveling, keeping appointments, keeping track of current events, and understanding media. FAQ total score is calculated by adding the scores from each of the 10 items. A negative change indicates an improvement from baseline.
FAQ Total Score is the sum of 10 items, ranging from 0 (best possible outcome) to 100 (worst possible outcome). LS Mean value is controlled for baseline value, baseline age, pooled investigator, treatment and visit.
Change From Baseline in Clinical Dementia Rating-Sum of Boxes (CDR-SB) [Time Frame: Baseline, Week 80]
CDR-SB is a semi-structured interview of participants and their caregivers. Participant's cognitive status is rated across 6 domains of functioning, including memory, orientation, judgment/problem solving, community affairs, home/hobbies, and personal care. Severity score is assigned for each of 6 domains; total score (SB) ranges from 0 to 18. Higher scores indicate greater disease severity. LS Mean value is controlled for baseline value, baseline age, pooled investigator, treatment and visit.
Change From Baseline in Neuropsychiatric Inventory (NPI) [Time Frame: Baseline, Week 80]
NPI assesses psychopathology in participants with dementia and other neurologic disorders. Information is obtained from a caregiver familiar with the participant's behavior. Total score ranges from 12 to 144; Higher scores indicate greater disease severity. LS Mean value is controlled for baseline value, baseline age, pooled investigator, treatment and visit.
Change From Baseline in Resource Utilization in Dementia-Lite (RUD-Lite) [Time Frame: Baseline, Week 80]
Assesses healthcare resource utilization (formal and informal care). Information gathered on both caregivers (care-giving time, work status) and participants (accommodation and healthcare resource utilization) is gathered from baseline and follow-up interviews. Report number of hospitalizations per participant up to 76 weeks. LS Mean value is controlled for baseline value, baseline age, pooled investigator, treatment and visit.
Change From Baseline in Quality of Life in Alzheimer's Disease (QoL-AD) [Time Frame: Baseline, Week 80]
Assesses QOL for AD: participant rates mood, relationships, memory, finances, physical condition, and overall QOL assessment. Each of 13 items, rated on a 4-point scale. Sum of items=total score (range: 13 to 52). Higher scores indicate TABLE 13-continued

| Outcome Measurements |
|---| greater QoL. Participant's primary caregiver is asked to complete same measure. LS Mean value is controlled for baseline value, baseline age, pooled investigator, treatment and visit.
Change From Baseline in 5-Dimensional EuroQol Quality of Life Scale Proxy Version (EQ-5D Proxy)
[Time Frame: Baseline, Week 80]
EQ-5D (proxy version) measures mobility, self-care, usual activities, pain/discomfort, anxiety/depression. 3 severity levels: no, some, severe problems. Visual analog scale (VAS) assesses caregiver's impression of participant's health state; score ranges: 0 to 100 millimeter (mm). Lower scores=greater disease severity LS Mean value is controlled for baseline value, baseline age, pooled investigator, treatment and visit.
Change From Baseline in Integrated Alzheimer's Disease Rating Scale (iADRS) [Time Frame: Baseline, Week 80]
Integrated Alzheimer's Disease Rating Scale is used to assess that Azidothymidine slows down the cognitive and functional decline associated with AD compared with placebo. iADRS is a simple linear combination of ADAS-Cog 13 or 14 and the ADCS-iADL. The scale ranges from 0 to 146, where lower scores indicate worse performance. LS Mean value is controlled for baseline value, baseline age, pooled investigator, treatment and visit.
Percentage of Participants of Cognitive and Functional Responders [Time Frame: Baseline through Week 80]
Assess the proportion of participants who reach certain levels of cognitive and functional decline. Decline in cognition is defined as worsening from baseline by at least 6 or 9 points on the ADAS Cog14. If there is a cognitive decline of a specified cut-off or more at any time then the participant is considered a nonresponder. Functional nonresponders are participants who have not had any of the following at any time point: Clinically evident decline in ability to perform one or more basic ADL present at baseline; A clinically evident decline in ability to perform 20% or more of the instrumental ADL present at baseline; An increase in global CDR score of 1 point or more compared with baseline. A decline from no impairment to mild impairment (bADL, iADL is not considered clinically significant, but other declines of 1 or more points and any participant discontinuation within the first 6 months will be considered a non-responder.
Change From Baseline in Plasma Amyloid-Beta (Aβ) Species [Time Frame: Baseline, Week 80]
Concentration of amino acid peptide known as Aβ 1-42 in plasma. The change in plasma Aβ analytes after treatment is assessed separately for each plasma Aβ parameter. LS Mean value is controlled for baseline value, baseline age, pooled investigator, treatment and visit.
Change From Baseline in Volumetric Magnetic Resonance Imaging (vMRI) [Time Frame: Baseline, Week 80]
The vMRI assessment of right and left hippocampal atrophy, is reported. LS Mean value is controlled for baseline value, baseline age, pooled investigator, treatment and visit.
Pharmacokinetics (PK): Area Under the Concentration Time Curve (AUC) of Azidothymidine [ Time Frame: Visit 2 (Post-dose), Visit 5, 9, 15 (Pre-dose, Post-dose) and Visit 22 (Pre-dose): Pre-dose before administration, Post-dose 30 minutes End of administration]
Area Under the Concentration versus Time Curve is evaluated for Azidothymidine.
Change From Baseline in Florbetapir Positron Emission Tomography (PET) Scan [Time Frame: Baseline, Week 80]
Florbetapir PET imaging is used to confirm the presence of amyloid pathology consistent with AD. Change from baseline is done to test the hypothesis that amyloid burden is reduced in participants in the treatment group. The change from baseline to the postbaseline visit of the composite summary standard uptake value ratio of florbetapir F18 is calculated. LS Mean value is controlled for baseline value, baseline age, pooled investigator, treatment and visit. The composite summary measure is an unweighted average of the 6 smaller regions TABLE 13-continued

| Outcome Measurements |
|---|
| (anterior cingulate, frontal medial orbital, parietal, posterior cingulate, precuneus, and temporal) normalized to whole cerebellum or subject-specific white matter. Change From Baseline in Cerebrospinal Fluid (CSF) Aβ Levels [Time Frame: Baseline, Week 80] Concentration of CSF parameters includes amino acid peptide known as Aβ 1-42 and Aβ 1-42. Analyses of these CSF biomarkers are conducted in a subset of participants (as an addendum to the protocol). The dependent variable for each CSF parameter is its change from baseline to endpoint. LS Mean value is controlled for baseline value, baseline age, pooled investigator, treatment and visit. |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of inhibiting generation of one or more non-classical variants of an amyloid precursor protein (APP) gene in an individual in need thereof, the method comprising: administering to the individual a nucleoside reverse transcriptase inhibitor or a salt thereof, wherein the individual is a human and has one or more non-classical variants of an amyloid precursor protein (APP) gene; wherein the one or more non-classical variants comprise a portion or all of exon 1, 2, 3, 4, 5, 6, 7, 8, 9, 10, 11, 12, 13, 14, 15, 16, 17, 18, or any combination thereof of the APP gene, thereby inhibiting generation of the one or more non-classical variants of the APP gene in the individual; and wherein the nucleoside reverse transcriptase inhibitor is selected from the group consisting of azidothymidine and abacavir.

2. The method of claim 1, wherein the individual does not have human immunodeficiency virus (HIV) or Hepatitis-B.

3. The method of claim 1, wherein the individual has Alzheimer's disease.

4. The method of claim 3, wherein the Alzheimer's disease is familial Alzheimer's disease (FAD) or sporadic Alzheimer's disease.

5. The method of claim 1, wherein the nucleoside reverse transcriptase inhibitor is abacavir.

6. The method of claim 1, wherein the one or more non-classical variants comprise a portion or all of exon 1, 2, 3, 4, 5, 6, 7, 8, 9, 10, 11, 12, 13, 14, 15, 16, 17 or any combination thereof of the APP gene.

7. The method of claim 1, wherein one or more exons in the one or more non-classical variants are rearranged as compared to a control.

8. The method of claim 1, wherein the one or more non-classical variants comprise one or more single nucleotide variations (SNV) in the APP gene.

9. The method of claim 8, wherein the SNV in the APP gene translates to an amino acid substitution in a protein expressed by the APP gene, wherein the amino acid substitution is selected from the group consisting of P620L, A673V, D678N, T714I, V715M, V715A, I716V, V717I, V717F, T719P, and L723P.

10. The method of claim 1, wherein the one or more non-classical variants comprise a sequence as set forth in SEQ ID NO: 1, 2, 3, 4, 5, 6, 7, 8, 9, 10, 11, 12, 13, 14, 15, or 16.

11. A method of treating or preventing Alzheimer's disease in an individual in need thereof, comprising: administering to the individual a nucleoside reverse transcriptase inhibitor or a salt thereof, wherein the individual does not have HIV or Hepatitis-B, wherein the individual is a human and has one or more non-classical variants of an amyloid precursor protein (APP) gene; and wherein the one or more non-classical variants comprise a portion or all of exon 1, 2, 3, 4, 5, 6, 7, 8, 9, 10, 11, 12, 13, 14, 15, 16, 17, 18, or any combination thereof of the APP gene; and wherein the nucleoside reverse transcriptase inhibitor is selected from the group consisting of azidothymidine and abacavir.

12. The method of claim 11, wherein the Alzheimer's disease is early onset Alzheimer's disease.

13. The method of claim 12, wherein the Alzheimer's disease is familial Alzheimer's disease or sporadic Alzheimer's disease.

14. The method of claim 11, wherein the nucleoside reverse transcriptase inhibitor is abacavir.

15. A method of diagnosing and treating a disease or disorder in an individual characterized by accumulation of amyloid beta protein in an individual in need thereof, comprising:
   (a) identifying the individual as having the disease or disorder characterized by unwanted accumulation of amyloid beta protein by comparing an expression profile or an activity profile of one or more non-classical variants of an APP gene to a reference expression profile of the one or more non-classical variants derived from a cohort of control individuals,
   wherein the expression profile or the activity profile of the one or more non-classical variants is measured by a method comprising long-read sequencing of a biological sample from the individual or binding of one or more probes to the biological sample from the individual; and
   wherein the expression profile or the activity profile of the one or more non-classical variants is associated with the neurological disease or disorder; and
   (b) administering to the individual having an expression profile or an activity profile of the one or more non-classical variants a nucleoside reverse transcriptase inhibitor or salt thereof, wherein the individual is a human and the one or more non-classical variants comprise a portion or all of exon 1, 2, 3, 4, 5, 6, 7, 8, 9, 10, 11, 12, 13, 14, 15, 16, 17, 18, or any combination thereof of the APP gene, and wherein the nucleoside reverse transcriptase inhibitor is selected from the group consisting of azidothymidine and abacavir.

16. The method of claim 15, wherein the reverse transcriptase inhibitor is abacavir.

17. The method of claim 15, wherein the reverse transcriptase inhibitor is azidothymidine.

* * * * *

SEQUENCE LISTING

<160> NUMBER OF SEQ ID NOS: 58

<210> SEQ ID NO 1
<211> LENGTH: 555
<212> TYPE: DNA
<213> ORGANISM: Homo sapiens

<400> SEQUENCE: 1

```
atgctgcccg gtttggcact gctcctgctg gccgcctgga cggctcgggc gctggaggta      60
cccactgatg gtaatgctgg cctgctggct gaacccaga ttgccatgtt ctgtggcaga      120
ctgaacatgc acatgaatgt ccagaatggg aagtgggatt cagatccatc agggaccaaa    180
acctgcattg ataccaagga aggcatcctg cagtattgcc aagaagtcta ccctgaactg    240
cagatcacca agatggatgc agaattccga catgactcag gatatgaagt tcatcatcaa    300
aaattggtgt tctttgcaga agatgtgggt tcaaacaaag gtgcaatcat tggactcatg    360
gtgggcggtg ttgtcatagc gacagtgatc gtcatcacct tggtgatgct gaagaagaaa    420
cagtacacat ccattcatca tggtgtggtg gaggttgacg ccgctgtcac cccagaggag    480
cgccacctgt ccaagatgca gcagaacggc tacgaaaatc caacctacaa gttctttgag    540
cagatgcaga actag                                                       555
```

<210> SEQ ID NO 2
<211> LENGTH: 555
<212> TYPE: DNA
<213> ORGANISM: Homo sapiens

<400> SEQUENCE: 2

```
atgctgcccg gtttggcact gctcctgctg gccgcctgga cggctcgggc gctggaggta      60
cccactgatg gtaatgctgg cctgctggct gaacccaga ttgccatgtt ctgtggcaga      120
ctgaacatgc acatgaatgt ccagaatggg aagtgggatt cagatccatc agggaccaaa    180
acctgcattg ataccaagga aggcatcctg cagtattgcc aagaagtcta ccctgaactg    240
cagatcacca agatggatgc agaattccga catgactcag gatatgaagt tcatcatcaa    300
aaattggtgt tctttgcaga agatgtgggt tcaaacaaag gtgcaatcat tggactcata    360
gtgggcggtg ttgtcatagc gacagtgatc gtcatcacct tggtgatgct gaagaagaaa    420
```

```
cagtacacat ccattcatca tggtgtggtg gaggttgacg ccgctgtcac cccagaggag    480
cgccacctgt ccaagatgca gcagaacggc tacgaaaatc caacctacaa gttctttgag    540
cagatgcaga actag                                                     555
```

```
<210> SEQ ID NO 3
<211> LENGTH: 258
<212> TYPE: DNA
<213> ORGANISM: Homo sapiens

<400> SEQUENCE: 3
atgctgcccg gtttggcact gctcctgctg gccgcctgga cggctcgggc gctggaggta     60
cccactgatg gtaatgctgg cctgctggct gaaccccaga ttgccatgtt ctgtggcaga    120
ctgaacatgc acatgaatgt ccagaatggg aagtgggatt cagatccatc agggaccaaa    180
acctgcattg ataccaagga aggcatcctg cgctacgaaa atccaaccta caagttcttt    240
gagcagatgc agaactag                                                  258
```

```
<210> SEQ ID NO 4
<211> LENGTH: 816
<212> TYPE: DNA
<213> ORGANISM: Homo sapiens

<400> SEQUENCE: 4
atgctgcccg gtttggcact gctcctgctg gccgcctgga cggctcgggc gctggaggta     60
cccactgatg gtaatgctgg cctgctggct gaaccccaga ttgccatgtt ctgtggcaga    120
ctgaacatgc acatgaatgt ccagaatggg aagtgggatt cagatccatc agggaccaaa    180
acctgcattg ataccaagga aggcatcctg cagtattgcc aagaagtcta ccctgaactg    240
cagatcacca atgtggtaga agccaaccaa ccagtgacca tccagaactg gtgcaagcgg    300
ggccgcaagc agtgcaagac ccatccccac tttgtgattc cctaccgctg cttagttggt    360
gagtttgtaa gtgatgccct tctcgttcct gacaagtgca aattcttaca ccaggagagg    420
atggatgttt gcgaaactca tcttcactgg cacaccgtcg ccaaagagac atgcagtgag    480
aagagtacca acttgcatga ctacggcatg ttgctgccct gcggaattga caagttccga    540
ggggtagagt ttgtgtgttg cccactggct gaagaaagtg acaatgtgga ttctgctgat    600
gcggaggagg atgactcgga tgtctggtgg ggcgagcag acacagacta tgcagatggg    660
agtgaagaca agtagtaga agtagcagag gaggaagaag tggctgaggt ggaagaagaa    720
gaagccgatg atgacgagga cgccacctg tccaagatgc agcagagcgg ctacgaaaat    780
ccaacctaca gttctttga gcagatgcag aactag                              816
```

```
<210> SEQ ID NO 5
<211> LENGTH: 684
<212> TYPE: DNA
<213> ORGANISM: Homo sapiens

<400> SEQUENCE: 5
atgctgcccg gtttggcact gctcctgctg gccgcctgga cggctcgggc gctggaggta     60
cccactgatg gtaatgctgg cctgctggct gaaccccaga ttgccatgtt ctgtggcaga    120
ctgaacatgc acatgaatgt ccagaatggg aagtgggatt cagatccatc agggaccaaa    180
acctgcattg ataccaagga aggcatcctg cagtattgcc aagaagtcta ccctgaactg    240
cagatcacca atgtggtaga agccaacaca gaaaacgaag ttgagcctgt tgatgcccgc    300
```

```
cctgctgccg accgaggact gaccactcga ccaggttctg ggttgacaaa tatcaagacg        360
gaggagatct ctgaagtgaa gatggatgca gaattccgac atgactcagg atatgaagtt        420
catcatcaaa aattggtgtt ctttacagaa gatgtgggtt caaacaaagg tgcaatcatt        480
ggactcatgg tgggcggtgt tgtcatagcg acagtgatcg tcatcacctt ggtgatgctg        540
aagaagaaac agtacacatc cattcatcat ggtgtggtgg aggttgacgc cgctgtcacc        600
ccagaggagc gccacctgtc caagatgcag cagaacggct acgaaaatcc aacctacaag        660
ttctttgagc agatgcagaa ctag                                                684

<210> SEQ ID NO 6
<211> LENGTH: 499
<212> TYPE: DNA
<213> ORGANISM: Homo sapiens

<400> SEQUENCE: 6
atgctgcccg gtttggcact gctcctgctg gccgcctgga cggctcgggc gctggagata         60
cccactgatg gtaatgctgg cctgctggct gaaccccaga ttgccatgtt ctgtggcaga        120
ctgaacatgc acatgaatgt ccagaatggg aagtgggact cagatccatc agggaccaaa        180
acctgcattg ataccaagga aggcatcctg cagtattgcc aagaagtcta ccctgaactg        240
cagatcacca atgtggtaga agccaaccaa ccagtgacca tccagaactg gtgcaagcgg        300
ggccgcaagc agtgttgtca tagcgacagt gatcgtcatc accttggtga tgctgaagaa        360
gaaacagtac acatccattc atcatggtgt ggtggaggtt gacgccgctg tcacccagag        420
ggagcgccac ctgtccaaga tgcagcagaa cggctacgaa aatccaacct acaagttctt        480
tgagcagatg cagaactag                                                    499

<210> SEQ ID NO 7
<211> LENGTH: 898
<212> TYPE: DNA
<213> ORGANISM: Homo sapiens

<400> SEQUENCE: 7
atgctgcccg gtttggcact gctcctgctg gccgcctgga cggcctcgtc acgtgttcaa         60
tatgctaaag aagtatgtcc gcgcagaaca gaaggacaga cagcacaccc taaagcattt        120
cgagcatgtg cgcatggtgg atcccaagaa agccgctcag atccggtccc aggttatgac        180
acacctccgt gtgatttatg agcgcatgaa tcagtctctc tccctgctct acaacgtgcc        240
tgcagtggcc gaggagattc aggatgaagt tgatgagctg cttcagaaag gcaaaaacta        300
ttcagatgac gtcttggcca acatgattag tgaaccaagg atcagttacg aaacgatgc        360 tctcatgcca tctttgaccg aaacgaaaac caccgtggag ctccttcccg tgaatggaga        420
gttcagcctg gacgatctcc agccgtggca ttcttttggg gctgactctg tgccagccaa        480
cacagaaaac gaagttgagc ctgttgatgc ccgccctgct gccgaccgag gactgaccac        540
tcgaccaggt tctggggttga caaatatcaa gacggaggag atctctgaag tgaagatgga        600
tgcagaattc cgacatgact caggatatga agttcatcat caaaaattgg tgttctttgc        660
agaagatgtg ggttcaaaca aaggtgcaat cattggactc atggtgggtg tgttgtcat        720 agcgacagtg atcgtcatca ccttggtgat gctgaagaag aaacagtaca catccattca        780
tcatggtgtg gtggaggttg acgccgctgt cacccagag gagcgccacc tgtccaagat        840
gcagcagaac ggctacgaaa atccaaccta caagttcttt gagcagatgc agaactag         898
```

<210> SEQ ID NO 8
<211> LENGTH: 680
<212> TYPE: DNA
<213> ORGANISM: Homo sapiens

<400> SEQUENCE: 8

```
atgctgcccg gtttggcact gctcctgcag tgggaggaga ttcaggatga agttgatgaa      60
ctgcttcaga aagagcaaaa ctattcagat gacgtcttgg ccaacatgat tagtgaacca     120
aggatcagtt acggaaacga tgctctcatg ccatctttga ccgaaacgaa aaccaccgtg     180
gagctccttc ccgtgaatgg agagttcagc ctggacgatc tccagccgtg gcattctttt     240
ggggctgact ctgtgccagc caacacagaa aacgaagttg agcctgttga tgcccgccct     300
gctgccgacc gaggactgac cactcgacca ggttctgggt tgacaaatat caagacggag     360
gagatctctg aagtgaagat ggatgcagaa ttccgacatg actcaggata tgaagttcat     420
catcaaaaat tggtgttctt tgcagaagat gtgggttcaa acaaaggtgc aatcattgga     480
ctcatggtgg cggtgttgtc atagcgacag tgatcgtcat caccttggtg atgctgaaga     540
agaaacagta cacatccatt catcatggtg tggtggaggt tgacgccgct gtcacccag      600
aggagcgcca cctgtccaag atgtggcaga acggctacga aaatccaacc tacaagttct     660
ttgagcagat gcagaactag                                                 680
```

<210> SEQ ID NO 9
<211> LENGTH: 899
<212> TYPE: DNA
<213> ORGANISM: Homo sapiens

<400> SEQUENCE: 9

```
atgctgcccg gtttggcact gctctgcagg ctgttcctcc tcggcctcgt cacgtgttca      60
atatgctaaa gaagtatgtc cgcgcagaac agaaggacag acagcacacc ctaaagcatt     120
tcgagcatgt gcgcatggtg atcccaaga aagccgctca gatccggtcc caggttatga     180
cacacctccg tgtgatttat gagcgcatga atcagtctct ctccctgctc tacaacgtgc     240
ctgcagtggc cgaggagatt caggatgaag ttgatgagct gcttcagaaa gagcaaaact     300
attcagatga cgtcttggcc aacatgatta gtgaaccaag gatcagttac ggaaacgatg     360
ctctcatgcc atctttgacc gaaacgaaaa ccaccgtgga gctccttccc gtgaatggag     420
agttcagcct ggacgatctc cagccgtggc attcttttgg ggctgactct gtgccagcca     480
acacagaaaa cgaagttgag cctgttgatg cccgccctgc tgccgaccga ggactgacca     540
ctcgaccagg ttctgggttg acaaatatca agacggagga gatctctgaa gtgaagatgg     600
atgcagaatt ccgacatgac tcaggatatg aagttcatca tcaaaaattg gtgttctttg     660
cagaagatgt gggttcaaac aaaggtgcaa tcattggact catggtgggc ggtgttgtca     720
tagcgacagt gatcgtcatc accttggtga tgctgaagaa gaaacagtac acatccattc     780
atcatggtgt ggtggaggtt gacgccgctg tcacccagag ggagcgccac ctgtccaaga     840
tgcagcagaa cggctacgaa aatccaacct acaagttctt tgagcagatg cagaactag      899
```

<210> SEQ ID NO 10
<211> LENGTH: 541
<212> TYPE: DNA
<213> ORGANISM: Homo sapiens

<400> SEQUENCE: 10

```
atgctgcccg gtttggcact gctcctgctg gccgcctgga cagctccttc ccgtgaatgg      60
```

```
agagttcagc ctggacgatc tccagccgtg gcattctttt ggggctgact ctgtgccagc    120
caacacagaa aacgaagttg agcctgttga tgcccgccct gctgccgacc gaggactgac    180
cactcgacca ggttctgggt tgacaaatat caagacggag gagatctctg aagtgaagat    240
ggatgcagaa ttccgacatg actcaggata tgaagttcat catcaaaaat tggtgttctt    300
tgcagaagat gtgggttcaa acaaaggtgc aatcattgga ctcatggtgg cggtgttgt     360 catagcgaca gtgatcgtca tcaccttggt gatgctgaag aagaaacagt acacatccat    420
tcatcatggt gtggtggagg ttgacgccgc tgtcacccca gaggagcgcc acctgtccaa    480
gatgcagcag aacggctacg aaaatccaac ctacaagttc tttgagcaga tgcagaacta    540
g                                                                    541

<210> SEQ ID NO 11
<211> LENGTH: 274
<212> TYPE: DNA
<213> ORGANISM: Homo sapiens

<400> SEQUENCE: 11
atgctgcccg ttttggcact gctcctgctg gccgcctgga cggctcgggc gctggaggta     60
cccaatcatt ggactcatgg tgggcggtgt tgtcatagcg acagtgatcg tcatcacctt    120
ggtgatgctg aagaagaaac agtacacatc cattcatcat ggtgtggtgg aggttgacgc    180
cgctgtcacc ccagaggagc gccacctgtc caagatgcag cagaacggct acgaaaatcc    240
aacctacaag ttctttgagc agatgcagaa ctag                                274

<210> SEQ ID NO 12
<211> LENGTH: 515
<212> TYPE: DNA
<213> ORGANISM: Homo sapiens

<400> SEQUENCE: 12
atgctgcccg ttttggcact gctcctgctg gccgcctgga cggctcgggc gctggaggta     60
cccactgatg gtaatgctgg cctgctggct gaaccccaga ttgccatgtt ctgtggcaga    120
ctgaacatgc acatgaatgt ccagaatggg aagtgggatt cagatccatc agggaccaaa    180
acctgcattg ataccaagga aggcatcctg cagtatatgc agaattccga catgactcag    240
gatatgaagt tcatcatcaa aaattggtgt tctttgcaga gatgtgggt tcaaacaaag     300 gtgcaatcat tggactcatg gtgggcggtg ttgtcatagc gacagtgatc gtcatcacct    360
tggtgatgct gaagaagaaa cagtacacat ccattcatca tggtgtggtg gaggttgacg    420
ccgctgtcac cccagaggag cgccacctgt ccaagatgca gcagaacggc tacgaaaatc    480
caacctacaa gttctttgag cagatgcaga actag                               515

<210> SEQ ID NO 13
<211> LENGTH: 888
<212> TYPE: DNA
<213> ORGANISM: Homo sapiens

<400> SEQUENCE: 13
atgctgcccg ttttggcact gctcctgctg gccgcctgga cggctcgggc gctggaggta     60
cccactgatg gtaatgctgg cctgctggct gaaccccaga ttgccatgtt ctgtggcaga    120
ctgaacatgc acatgaatgt ccagaatggg aagtgggatt cagatccatc agggaccaaa    180
acctgcattg ataccaagga aggcatcctg cagtattgcc aagaagtcta ccctgaactg    240
cagatcacca atgtggtaga agccaaccaa ccagtgacca tccagaactg gtgcaagcgg    300
```

```
ggccgcaagc agtgcaagac ccatccccac tttgtgattc cctaccgctg cttagttggt    360
gagtttgtaa gtgatgccct tctcgttcct gacaagtgca aattcttaca ccaggagagg    420
atggatgttt gcgaaactca tcttcactgg cacaccgtcg ccaaagagac atgcagtgag    480
aagagtacca acttgcatga ctacggcatg ttgctgccct gcggaattga caagttccga    540
ggggtagagt ttgtgtgttg cccactggct gaagaaagtg acaatgtgga ttctgctgat    600
gcggaggagg atgactcgga tgtctggtgg ggcggagcag acacagacta tgcagatggg    660
agtgaagaca aaggtgcaat cattggactc atggtgggcg tgttgtcat agcgacagtg     720 atcgtcatca ccttggtgat gctgaagaag aaacagtaca catccattca tcatggtgtg    780
gtggaggttg acgccgctgt caccccagag gagcgccacc tgtccaagat gcagcagaac    840
ggctacgaaa atccaaccta caagttcttt gagcagatgc agaactag                 888

<210> SEQ ID NO 14
<211> LENGTH: 757
<212> TYPE: DNA
<213> ORGANISM: Homo sapiens

<400> SEQUENCE: 14
atgctgcccg gtttggcact gctcctgctg gccgcctgga cggctcgggc gctggaggta     60
cccactgatg gtaatgctgg cctgctggct gaacccagat tgccatgtt ctgtggcaga    120 ctgaacatgc acatgaatgt ccagaatggg aagtgggatt cagatccatc agggaccaaa    180
acctgcattg ataccaagga tcagttacgg aaacgatgct ctcatgccat ctttgaccga    240
aacgaaaacc accgtggagc tccttcccgt gaatggagag ttcagcctgg acgatctcca    300
gccgtggcat tcttttgggg ctgactctgt gccagccaac acagaaaacg aagttgagcc    360
tgttgatgcc cgccctgctg ccgaccgagg actgaccact cgaccaggtt ctgggttgac    420
aaatatcaag acggaggaga tctctgaagt gaagatggat gcagaattcc gacatgactc    480
aggatatgaa gttcatcatc aaaaattggt gttctttgca gaagatgtgg gttcaaacaa    540
aggtgcaatc attggactca tgtgggcggt gttgtcata gcgacagtga tcgtcatcac    600
cttggtgatg ctgaagaaga aacagtacac atccattcat catggtgtgg tggaggttga    660
cgccgctgtc accccagagg agcgccacct gtccaagatg cagcagaacg ctacgaaaa     720 tccaacctac aagttctttg agcagatgca gaactag                             757

<210> SEQ ID NO 15
<211> LENGTH: 1879
<212> TYPE: DNA
<213> ORGANISM: Homo sapiens

<400> SEQUENCE: 15
atgctgcccg gtttggcact gctcctgctg gccgcctgga cggctcgggc gctggaggta     60
cccactgatg gtaatgctgg cctgctggct gaacccagat tgccatgtt ctgtggcaga    120 ctgaacatgc acatgaatgt ccagaatggg aagtgggatt cagatccatc agggaccaaa    180
acctgcattg ataccaagga aggcatcctg cagtattgcc aagaagtcta ccctgaactg    240
cagatcacca atgtggtaga agccaaccaa ccagtgacca tccagaactg gtgcaagcgg    300
ggccgcaagc agtgcaagac ccatccccac tttgtgattc cctaccgctg cttagttggt    360
gagtttgtaa gtgatgccct tctcgttcct gacaagtgca aattcttaca ccaggagagg    420
atggatgttt gcgaaactca tcttcactgg cacaccgtcg ccaaagagac atgcagtgag    480
```

```
aagagtacca acttgcatga ctacggcatg ttgctgccct gcggaattga caagttccga    540
ggggtagagt ttgtgtgttg cccactggct gaagaaagtg acaatgtgga ttctgctgat    600
gcggaggagg atgactcgga tgtctggtgg ggcggagcag acacagacta tgcagatggg    660
agtgaagaca aagtagtaga agtagcagag gaggaagaag tggctgaggt ggaagaagaa    720
gaagccgatg atgacgagga cgatgaggat ggtgatgagg tagaggaaga ggctgaggaa    780
ccctacgaag aagccacaga gagaaccacc agcattgcca ccaccaccac caccaccaca    840
gagtctgtgg aagaggtggt tcgagaggtg tgctctgaac aagccgagac ggggccgtgc    900
cgagcaatga tctcccgctg gtactttgat gtgactgaag ggaagtgtgc cccattcttt    960
tacggcggat gtggcggcaa ccggaacaac tttgacacag aagagtactg catggccgtg   1020
tgtggcagcg ccattcctac aacagcagcc agtacccctg atgccgttga caagtatctc   1080
gagacacctg gggatgagaa tgaacatgcc catttccaga aagccaaaga gaggcttgag   1140
gccaagcacc gagagagaat gtcccaggtc atgagagaat gggaagaggc agaacgtcaa   1200
gcaaagaact tgcctaaagc tgataagaag gcagttatcc agcatttcca ggagaaagtg   1260
gaatctttgg aacaggaagc agccaacgag agacagcagc tggtggagac acacatggcc   1320
agagtggaag ccatgctcaa tgaccgccgc cgcctggccc tggagaacta catcaccgct   1380
ctgcaggctg ttcctcctcg gcctcgtcac gtgttcaata tgctaaagaa gtatgtacgc   1440
gcagaacaga aggacagaca gcacacccta aagcatttcg agcatgtgcg catggtggat   1500
cccaagaaag ccgctcagat ccggtcccag gttatgacac tcctccgtgt gatttatgag   1560
cgcatgaatc agtctctctc cctgctctac aacgtgcctg cagtggccga ggagattcag   1620
gatgaagttg gtgttctttg cagaagatgt gggttcaaac aaaggtgcaa tcattggact   1680
catggtgggc ggtgttgtca tagcgacagt gatcgtcatc accttggtga tgctgaagaa   1740
gaaacagtac acatccattc atcatggtgt ggtggaggtt gacgccgctg tcaccccaga   1800
ggagcgccac ctgtccaaga tgcagcagaa cggctacgaa aatccaacct acaagttctt   1860
tgagcagatg cagaactag                                                1879

<210> SEQ ID NO 16
<211> LENGTH: 144
<212> TYPE: DNA
<213> ORGANISM: Homo sapiens

<400> SEQUENCE: 16
atgctgcccg gtttggcact gctcctgctg gccgcctgga cggctcgggc gctggaggta     60
cccactgatg gtaatgctgg cctgctggct gaaccccaga ttgccatgtt ctgtggcaga    120
aagttctttg agcagatgca gaac                                           144

<210> SEQ ID NO 17
<211> LENGTH: 770
<212> TYPE: PRT
<213> ORGANISM: Homo sapiens

<400> SEQUENCE: 17

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45
```

```
Asn Gly Lys Trp Asp Ser Asp Pro Ser Gly Thr Lys Thr Cys Ile Asp
     50                  55                  60
Thr Lys Glu Gly Ile Leu Gln Tyr Cys Gln Glu Val Tyr Pro Glu Leu
 65                  70                  75                  80
Gln Ile Thr Asn Val Val Glu Ala Asn Gln Pro Val Thr Ile Gln Asn
                 85                  90                  95
Trp Cys Lys Arg Gly Arg Lys Gln Cys Lys Thr His Pro His Phe Val
            100                 105                 110
Ile Pro Tyr Arg Cys Leu Val Gly Glu Phe Val Ser Asp Ala Leu Leu
            115                 120                 125
Val Pro Asp Lys Cys Lys Phe Leu His Gln Glu Arg Met Asp Val Cys
130                 135                 140
Glu Thr His Leu His Trp His Thr Val Ala Lys Glu Thr Cys Ser Glu
145                 150                 155                 160
Lys Ser Thr Asn Leu His Asp Tyr Gly Met Leu Leu Pro Cys Gly Ile
                165                 170                 175
Asp Lys Phe Arg Gly Val Glu Phe Val Cys Cys Pro Leu Ala Glu Glu
            180                 185                 190
Ser Asp Asn Val Asp Ser Ala Asp Ala Glu Glu Asp Asp Ser Asp Val
            195                 200                 205
Trp Trp Gly Gly Ala Asp Thr Asp Tyr Ala Asp Gly Ser Glu Asp Lys
210                 215                 220
Val Val Glu Val Ala Glu Glu Glu Val Ala Glu Val Glu Glu Glu Glu
225                 230                 235                 240
Glu Ala Asp Asp Asp Glu Asp Asp Glu Asp Gly Asp Glu Val Glu Glu
                245                 250                 255
Glu Ala Glu Glu Pro Tyr Glu Glu Ala Thr Glu Arg Thr Thr Ser Ile
            260                 265                 270
Ala Thr Thr Thr Thr Thr Thr Glu Ser Val Glu Glu Val Val Arg
            275                 280                 285
Glu Val Cys Ser Glu Gln Ala Glu Thr Gly Pro Cys Arg Ala Met Ile
            290                 295                 300
Ser Arg Trp Tyr Phe Asp Val Thr Glu Gly Lys Cys Ala Pro Phe Phe
305                 310                 315                 320
Tyr Gly Gly Cys Gly Gly Asn Arg Asn Asn Phe Asp Thr Glu Glu Tyr
                325                 330                 335
Cys Met Ala Val Cys Gly Ser Ala Met Ser Gln Ser Leu Leu Lys Thr
            340                 345                 350
Thr Gln Glu Pro Leu Ala Arg Asp Pro Val Lys Leu Pro Thr Thr Ala
            355                 360                 365
Ala Ser Thr Pro Asp Ala Val Asp Lys Tyr Leu Glu Thr Pro Gly Asp
            370                 375                 380
Glu Asn Glu His Ala His Phe Gln Lys Ala Lys Glu Arg Leu Glu Ala
385                 390                 395                 400
Lys His Arg Glu Arg Met Ser Gln Val Met Arg Glu Trp Glu Glu Ala
                405                 410                 415
Glu Arg Gln Ala Lys Asn Leu Pro Lys Ala Asp Lys Lys Ala Val Ile
            420                 425                 430
Gln His Phe Gln Glu Lys Val Glu Ser Leu Glu Gln Glu Ala Ala Asn
            435                 440                 445
Glu Arg Gln Gln Leu Val Glu Thr His Met Ala Arg Val Glu Ala Met
450                 455                 460
Leu Asn Asp Arg Arg Arg Leu Ala Leu Glu Asn Tyr Ile Thr Ala Leu
```

-continued

```
            465                 470                 475                 480
        Gln Ala Val Pro Pro Arg Pro Arg His Val Phe Asn Met Leu Lys Lys
                            485                 490                 495

Tyr Val Arg Ala Glu Gln Lys Asp Arg Gln His Thr Leu Lys His Phe
                        500                 505                 510

Glu His Val Arg Met Val Asp Pro Lys Lys Ala Ala Gln Ile Arg Ser
                    515                 520                 525

Gln Val Met Thr His Leu Arg Val Ile Tyr Glu Arg Met Asn Gln Ser
        530                 535                 540

Leu Ser Leu Leu Tyr Asn Val Pro Ala Ala Glu Glu Ile Gln Asp
        545                 550                 555                 560

Glu Val Asp Glu Leu Leu Gln Lys Glu Gln Asn Tyr Ser Asp Asp Val
                        565                 570                 575

Leu Ala Asn Met Ile Ser Glu Pro Arg Ile Ser Tyr Gly Asn Asp Ala
                    580                 585                 590

Leu Met Pro Ser Leu Thr Glu Thr Lys Thr Thr Val Glu Leu Leu Pro
                595                 600                 605

Val Asn Gly Glu Phe Ser Leu Asp Asp Leu Gln Pro Trp His Ser Phe
        610                 615                 620

Gly Ala Asp Ser Val Pro Ala Asn Thr Glu Asn Glu Val Glu Pro Val
        625                 630                 635                 640

Asp Ala Arg Pro Ala Ala Asp Arg Gly Leu Thr Thr Arg Pro Gly Ser
                        645                 650                 655

Gly Leu Thr Asn Ile Lys Thr Glu Gly Ile Ser Glu Val Lys Met Asp
                    660                 665                 670

Ala Glu Phe Arg His Asp Ser Gly Tyr Glu Val His His Gln Lys Leu
                675                 680                 685

Val Phe Phe Ala Glu Asp Val Gly Ser Asn Lys Gly Ala Ile Ile Gly
        690                 695                 700

Leu Met Val Gly Gly Val Val Ile Ala Thr Val Ile Val Ile Thr Leu
        705                 710                 715                 720

Val Met Leu Lys Lys Lys Gln Tyr Thr Ser Ile His His Gly Val Val
                        725                 730                 735

Glu Val Asp Ala Ala Val Thr Pro Glu Glu Arg His Leu Ser Lys Met
                    740                 745                 750

Gln Gln Asn Gly Tyr Glu Asn Pro Thr Tyr Lys Phe Phe Glu Gln Met
                755                 760                 765

Gln Asn
        770

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ctagttctgc atctgctcaa agaacttg                                           28

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 19
atgctgcccg gtttggca                                                   18

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctagttctgc atctgctcaa agaacttg                                         28

<210> SEQ ID NO 21
<211> LENGTH: 2211
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
actgctcctg ctggccgcct ggacggctcg ggcgctggag gtacccactg atggtaatgc      60
tggcctgctg gctgaacccc agattgccat gttctgtggc agactgaaca tgcacatgaa     120
tgtccagaat gggaagtggg attcagatcc atcagggacc aaaacctgca ttgataccaa     180
ggaaggcatc ctgcagtatt gccaagaagt ctaccctgaa ctgcagatca ccaatgtggt     240
agaagccaac caaccagtga ccatccagaa ctggtgcaag cggggccgca agcagtgcaa     300
gacccatccc cactttgtga ttccctaccg ctgcttagtt ggtgagtttg taagtgatgc     360
ccttctcgtt cctgacaagt gcaaattctt acaccaggag aggatggatg tttgcgaaac     420
tcatcttcac tggcacaccg tcgccaaaga gacatgcagt gagaagagta ccaacttgca     480
tgactacggc atgttgctgc cctgcggaat tgacaagttc cgaggggtag agtttgtgtg     540
ttgcccactg gctgaagaaa gtgacaatgt ggattctgct gatgcggagg aggatgactc     600
ggatgtctgg tggggcggag cagacacaga ctatgcagat gggagtgaag acaaagtagt     660
agaagtagca gaggaggaag aagtggctga ggtggaagaa gaagaagccg atgatgacga     720
ggacgatgag gatggtgatg aggtagagga agaggctgag gaaccctacg aagaagccac     780
agagagaacc accagcattg ccaccaccac caccaccacc acagagtctg tggaagaggt     840
ggttcgagag gtgtgctctg aacaagccga gacggggccg tgccgagcaa tgatctcccg     900
ctggtacttt gatgtgactg aagggaagtg tgccccattc ttttacggcg gatgtggcgg     960
caaccggaac aactttgaca cagaagagta ctgcatggcc gtgtgtggca gcgccattcc    1020
tacaacagca gccagtaccc ctgatgccgt tgacaagtat ctcgagacac tggggatga    1080
gaatgaacat gcccatttcc agaaagccaa agagaggctt gaggccaagc accgagagag    1140
aatgtcccag gtcatgagag aatgggaaga ggcagaacgt caagcaaaga acttgcctaa    1200
agctgataag aaggcagtta tccagcattt ccaggagaaa gtggaatctt tggaacagga    1260
agcagccaac gagagacagc agctggtgga gacacacatg gccagagtgg aagccatgct    1320
caatgaccgc cgccgcctgg ccctggagaa ctacatcacc gctctgcagg ctgttcctcc    1380
tcggcctcgt cacgtgttca atatgctaaa gaagtatgtc cgcgcagaac agaaggacag    1440
acagcacacc ctaaagcatt tcgagcatgt gcgcatggtg gatcccaaga agccgctca    1500

```
gatccggtcc caggttatga cacacctccg tgtgatttat gagcgcatga atcagtctct    1560
ctccctgctc tacaacgtgc ctgcagtggc cgaggagatt caggatgaag ttgatgagct    1620
gcttcagaaa gagcaaaact attcagatga cgtcttggcc aacatgatta gtgaaccaag    1680
gatcagttac ggaaacgatg ctctcatgcc atctttgacc gaaacgaaaa ccaccgtgga    1740
gctccttccc gtgaatggag agttcagcct ggacgatctc cagccgtggc attcttttgg    1800
ggctgactct gtgccagcca acacagaaaa cgaagttgag cctgttgatg cccgccctgc    1860
tgccgaccga ggactgacca ctcgaccagg ttctgggttg acaaatatca agacggagga    1920
gatctctgaa gtgaagatgg atgcagaatt ccgacatgac tcaggatatg aagttcatca    1980
tcaaaaattg gtgttctttg cagaagatgt gggttcaaac aaaggtgcaa tcattggact    2040
catggtgggc ggtgttgtca tagcgacagt gatcgtcatc accttggtga tgctgaagaa    2100
gaaacagtac acatccattc atcatggtgt ggtggaggtt gacgccgctg tcaccccaga    2160
ggagcgccac ctgtccaaga tgcagcagaa cggctacgaa aatccaacct a             2211

<210> SEQ ID NO 22
<211> LENGTH: 126
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
gatgcagaat tccgacatga ctcaggatat gaagttcatc atcaaaaatt ggtgttcttt     60
gcagaagatg tgggttcaaa caaaggtgca atcattggac tcatggtggg cggtgttgtc    120
atagcg                                                               126

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atgctgcccg gtttggca                                                   18

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctagttctgc atctgctcaa agaacttg                                        28

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
```
atgctgcccg gtttggca                                                        18

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctagttctgc atctgctcaa agaacttg                                             28

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atgacagagt tacctgcacc                                                      20

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ctagatataa aattgatgga a                                                    21

<210> SEQ ID NO 29
<211> LENGTH: 49
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
acatgactca ggatatgaag ttcatcatca aaaattggtg ttctttgca                      49

<210> SEQ ID NO 30
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
tgccaagaag tctaccctga actgcagatc accaagatgg atgc                           44

<210> SEQ ID NO 31
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gatccacatg actcaggata tgaagttcat catcaaaaat tggtgttctt tgcaa              55

```
<210> SEQ ID NO 32
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gatcttgcaa agaacaccaa tttttgatga tgaacttcat atcctgagtc atgtg          55

<210> SEQ ID NO 33
<211> LENGTH: 12
<212> TYPE: DNA
<213> ORGANISM: Homo sapiens

<400> SEQUENCE: 33
gacagtcagt ct                                                         12

<210> SEQ ID NO 34
<211> LENGTH: 10
<212> TYPE: DNA
<213> ORGANISM: Homo sapiens

<400> SEQUENCE: 34
ggcactgctc                                                            10

<210> SEQ ID NO 35
<211> LENGTH: 10
<212> TYPE: DNA
<213> ORGANISM: Homo sapiens

<400> SEQUENCE: 35
caccgctctg                                                            10

<210> SEQ ID NO 36
<211> LENGTH: 10
<212> TYPE: DNA
<213> ORGANISM: Homo sapiens

<400> SEQUENCE: 36
ataccaagga                                                            10

<210> SEQ ID NO 37
<211> LENGTH: 10
<212> TYPE: DNA
<213> ORGANISM: Homo sapiens

<400> SEQUENCE: 37
accaaggatc                                                            10

<210> SEQ ID NO 38
<211> LENGTH: 11
<212> TYPE: DNA
<213> ORGANISM: Homo sapiens

<400> SEQUENCE: 38
cctgcagtat t                                                          11

<210> SEQ ID NO 39
<211> LENGTH: 11
<212> TYPE: DNA
<213> ORGANISM: Homo sapiens
```

<400> SEQUENCE: 39
tgcagaattc c					11

<210> SEQ ID NO 40
<211> LENGTH: 22
<212> TYPE: DNA
<213> ORGANISM: Homo sapiens

<400> SEQUENCE: 40
gcagatggga gtgaagacaa ag				22

<210> SEQ ID NO 41
<211> LENGTH: 20
<212> TYPE: DNA
<213> ORGANISM: Homo sapiens

<400> SEQUENCE: 41
agatgggagt gaagacaaag				20

<210> SEQ ID NO 42
<211> LENGTH: 22
<212> TYPE: DNA
<213> ORGANISM: Homo sapiens

<400> SEQUENCE: 42
agatgtgggt tcaaacaaag gt				22

<210> SEQ ID NO 43
<211> LENGTH: 15
<212> TYPE: DNA
<213> ORGANISM: Homo sapiens

<400> SEQUENCE: 43
cactgctctg caggc					15

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gccttagcag tgccctgtct				20

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
aacatgctcg agggcctta				19

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 46
cttgaaccca ctaggtatag tg                                              22

<210> SEQ ID NO 47
<211> LENGTH: 18
<212> TYPE: DNA
<213> ORGANISM: Homo sapiens

<400> SEQUENCE: 47
ggcactgctc ctgctggc                                                   18

<210> SEQ ID NO 48
<211> LENGTH: 17
<212> TYPE: DNA
<213> ORGANISM: Homo sapiens

<400> SEQUENCE: 48
caccgctctg caggctg                                                    17

<210> SEQ ID NO 49
<211> LENGTH: 12
<212> TYPE: DNA
<213> ORGANISM: Homo sapiens

<400> SEQUENCE: 49
tgataccaag ga                                                         12

<210> SEQ ID NO 50
<211> LENGTH: 12
<212> TYPE: DNA
<213> ORGANISM: Homo sapiens

<400> SEQUENCE: 50
accaaggatc ag                                                         12

<210> SEQ ID NO 51
<211> LENGTH: 11
<212> TYPE: DNA
<213> ORGANISM: Homo sapiens

<400> SEQUENCE: 51
tagaagccaa c                                                          11

<210> SEQ ID NO 52
<211> LENGTH: 11
<212> TYPE: DNA
<213> ORGANISM: Homo sapiens

<400> SEQUENCE: 52
agccaacaca g                                                          11

<210> SEQ ID NO 53
<211> LENGTH: 10
<212> TYPE: DNA
<213> ORGANISM: Homo sapiens

<400> SEQUENCE: 53
gcaagcagtg                                                            10

<210> SEQ ID NO 54
<211> LENGTH: 10
<212> TYPE: DNA
```

```
<213> ORGANISM: Homo sapiens

<400> SEQUENCE: 54
gcggtgttgt                                                              10

<210> SEQ ID NO 55
<211> LENGTH: 24
<212> TYPE: DNA
<213> ORGANISM: Homo sapiens

<400> SEQUENCE: 55
atgcagatgg gagtgaagac aaag                                              24

<210> SEQ ID NO 56
<211> LENGTH: 24
<212> TYPE: DNA
<213> ORGANISM: Homo sapiens

<400> SEQUENCE: 56
agatgtgggt tcaaacaaag gtgc                                              24

<210> SEQ ID NO 57
<211> LENGTH: 11
<212> TYPE: DNA
<213> ORGANISM: Homo sapiens

<400> SEQUENCE: 57
agaattccga c                                                            11

<210> SEQ ID NO 58
<211> LENGTH: 11
<212> TYPE: DNA
<213> ORGANISM: Homo sapiens

<400> SEQUENCE: 58
aaatccaacc t                                                            11
```